United States Patent [19]

Splawski et al.

[11] Patent Number: 6,150,104
[45] Date of Patent: Nov. 21, 2000

[54] HOMOZYGOUS MUTATION IN KVLQT1 WHICH CAUSES JERVELL AND LANGE NIELSEN SYNDROME

[75] Inventors: Igor Splawski; Mark T. Keating, both of Salt Lake City, Utah

[73] Assignee: University of Utah Research Foundation, Salt Lake City, Utah

[21] Appl. No.: 09/135,021

[22] Filed: Aug. 17, 1998

Related U.S. Application Data

[63] Continuation-in-part of application No. 08/874,655, Jun. 13, 1997, abandoned
[60] Provisional application No. 60/094,477, Jul. 29, 1998.

[51] Int. Cl.⁷ .............................. C12Q 1/68; C12P 19/34; C12N 1/20; C07H 21/04
[52] U.S. Cl. ......................... 435/6; 435/91.2; 435/252.1; 536/23.1; 536/24.3
[58] Field of Search .......................... 435/6, 91.2, 252.1; 536/23.1, 24.3

[56] References Cited

PUBLICATIONS

Chouabe et al, The EMBO Journal, vol. 16, pp. 5472–5479 1997.
Ruano et al. Nuc. Acids Res. vol. 17, p. 8392 1989.
Levitan, Max. The Textbook of Human Genetics, 3rd ed., Oxford University Press, New YOurk 1988.
Ackerman, M.D., PhD., Michael J., "The Long QT Syndrome: Ion Channel Diseases of the Heart", *Mayo Clin Proc.* 1998:73:250–269.
Rakaf, M. Al, et al., "Jervell and Lange–Nielson QT syndrome: a case report from Saudi Arabia", *International Journal of Pediatric Otorthinolaryngology,* 39 (1997) 163–168.
Ben–Efraim, Iris, et al., "Spectroscopic and Functional Characterization of the Putative Transmembrane Segment of the minK Potassium Channel", *Biochemistry,* 1993, 32, 2371–2377.
Attali, Bernard, "A new wave for heart rhythms", *Nature,* vol. 384, Nov. 7, 1996, pp. 24–25.
Ben–Efraim, Iris, et al., "Secondary Structure and Membrane Localization of Synthetic Segments and a Truncated Form of the IsK (minK) Protein", *Biochemistry,* 1994, 33, 6966–6973.
Blumenthal, Edward M. and Kaczmarke, Leonard K., "Modulation by cAMP of a Slowly Activating Potassium Channel Expressed in Xenopus Oocytes", *The Journal of Neuroscience,* Jan. 1992, 12(1): 290–296.
Blumenthal, Edward M. and Kaczmarek, Leonard K., "The MinK Potassium Channel Exists in Functional and Nonfunctional Forms When Expressed in the Plasma Membrane of Xenopus Oocytes", *The Journal of Neuroscience,* May 1994, 14(5): 3097–3105.
Blumenthal, Edward M. and Kaczmarek, Leonard K., "Inward Rectification of the MinK Potassium Channel", *J. Membrane Biol.*, 136, 23–29 (1993).

Blumenthal, Edward M. and Kaczmarek, Leonard K., "Structure and Regulation of the MinK Potassium Channel", *Neurochemical Research,* vol. 17, No. 9, 1992, pp. 869–876.
Brahmajothi, Mulugu V., et al., "In Situ Hybridization Reveals Extensive Diversity of K⁺Channel mRNA in Isolated Ferret Cardiac Myocytes", *Circulation Research,* vol. 78, No. 6, Jun. 1996, pp. 1083–1089.
Busch, Andreas E., and Lang, Florian, "Time Dependent Changes in Biophysical Properties of minK Channels Expressed in Xenopus Oocytes", *Biochemical and Biophysical Research Communications,* vol. 197, No. 2, 1993, pp. 473–477.
Busch, Andreas E., and Suessbrich, Hartnut, "Role of the $I_{SK}$ protein in the $I_{minK}$ channel complex", *TIPS,* Jan. 1997 (vol. 18), pp. 26–29.
Chouabe, Christophe, et al., "Properties of KvLQT1 K⁺ channel mutations in Romano–Ward and Jervell and Lange–Nielsen inherited cardiac arrythmias", *The EMBO Journal,* vol. 16, No. 17, pp. 5472–5479, 1997.
Curran, Mark, et al., "Locus Heterogeneity of Autosomal Dominant Long QT Syndrome", *J. Clin. Invest.*, vol. 92, Aug. 1993, 799–803.
Curran, Mark E., et al., "A Molecular Basis for Cardiac Arrhythmia: Herg Mutations Cause Long QT Syndrome", *Cell,* vol. 80, 795–803, Mar. 10, 1995.
Duggal, Priya, et al., "Mutation of the Gene for IsK Associated With Both Jervell and Lange–Nielsen and Romano–Ward Forms of Long–QT Syndrome", *American Heart Association, Inc.*, pp. 142–146, 1998.
Freeman, Lisa C., and Kass, Robert S., "Expression of a Minimal K⁺ Channel Protein in Mammalian Cells and immunolocalization in Guinea Pig Heart", *Circulation Research,* vol. 73, No. 5, pp. 968–973, Nov. 1993.
Gellens, Mary E., et al., Primary structure and functional expression of the human cardiac tetrodotoxin–insensitive voltage–dependent sodium channel, *Proc. Natl. Acad. Sci. USA 89*, pp. 554–558, Jan. 1992.
George, Jr., A.L., et al., "Assignment of the human heart tetrodotoxin–resistant voltage–gated Na⁺ channel α–subunit gene (SCN5A) to band 3p21", *Cytogenet Cell Genet,* vol. 68, pp. 67–70, 1995.
Hoffman, PhD., Eric P., and Gardner, M.D., Kathy, "Ion Channels—Molecular Divining Rods Hit Their Clinical Mark", *New England Journal of Medicine,* vol. 336, pp. 1599–1600, May 29, 1997.

(List continued on next page.)

*Primary Examiner*—W. Gary Jones
*Assistant Examiner*—Jehanne Souaya
*Attorney, Agent, or Firm*—Rothwell, Figg, Ernst & Manbeck, P.C.

[57] ABSTRACT

Jervell and Lange-Nielsen syndrome (JLN) is an autosomal recessive form of long QT syndrome. In addition to QT interval prolongation, this disorder is associated with congenital deafness. JLN is rare, but affected individuals are susceptible to cardiac arrhythmias with a high incidence of sudden death and short life expectancy. A homozygous mutation in KVLQT1, the potassium channel gene responsible for chromosome 11-linked long QT syndrome, is shown to be a cause of JLN.

34 Claims, 5 Drawing Sheets

OTHER PUBLICATIONS

Jiang, Changan, et al. "Two Long QT syndrome loci map to chromosomes 3 and 7 with evidence for further heterogeneity", *Nature Genetics*, vol. 8, pp. 141–147, Oct. 1994.

Kaczmarek, Leonard K., "Voltage–Dependent Potassium Channels: minK and Shaker Families", *The New Biologist*, vol. 3, No. 4, pp. 315–323, Apr. 1991.

Keating, Mark, et al, "Linkage of a Cardiac Arrhythmia, the Long QT Syndrome, and the Harvey ras–1 Gene", *Science*, vol. 252, pp. 704–706, Mar. 1991.

Benhorin, Jesaia, et al., "Evidence of Genetic Heterogeneity in the Long QT Syndrome", *Science*, vol. 260, pp. 1960–1962, Jun. 1993.

Keating, M.D., Mark, "Linkage Analysis and Long QT Syndrome Using Genetics to Study Cardiovascular Disease", *Circulation*, vol. 85, No. 6, pp. 1973–1986, Jun. 1992.

Keating, M.D., Mark, et al, "Consistent Linkage of the Long–QT Syndrome to the Harvey Ras–1 Locus on Chromosome II", *Am. J. Hum. Genet*, 49:1335–1339, 1991.

Komsuoğlu, Baki, et al., "The Jervell and Lange–Nielsen syndrome", *International Journal of Cardiology* 47 (1994) 189–192.

Kukuljan, Manuel, et al., "Molecular determinants of ion conduction and inactivation in $K^+$ channels", *American Physiological Society*, C535–C556, 1995.

Lai, Ling–Ping, et al., "Polymorphism of the gene encoding a human minimal potassium ion channel (minK)", *Gene*, 151(1994) 339–340.

Lee, Maxwell, P., et al., "Human KVLQT1 gene shows tissue–specific imprinting and encompasses Beckwith––Wiedemann syndrome chromosomal rearrangements", *Nature Genetics*, vol. 15, pp. 181–185, Feb. 1997.

LoTurco, Joseph J., et al., "GABA and Glutamate Depolarize Cortical Progenitor Cells and Inhibit DNA Synthesis", *Neuron*, vol. 15, pp. 1287–1298, Dec. 1995.

Mannens, Marcel and Wilde, Arthur, "KVLQT1, the rhythm of imprinting", *Nature Genetics*, vol. 15, pp. 113–115, Feb. 1997.

Neyroud, Nathalie, "A novel mutation in the potassium channel gene KVLQT1 causes the Jervell and Lange–Nielsen cardioauditory syndrome", *Nature Genetics*, vol. 15, pp. 186–189, Feb. 1997.

Marx, Jean, "Rare Heart Disease Linked to Oncogene", *Research News*, p. 647, May 1991.

Neyroud, Nathalie, et al., "A novel mutation in the potassium channel gene KVLQT1 causes the Jervell and Lange–Nielsen cardioauditory syndrome", *Nature Genetics*, vol. 15, pp. 186–189, Feb. 1997.

Ptáček, Louis, J., et al., "Identification of a Mutation in the Gene Causing Hyperkalemic Periodic Paralysis", *Cell*, vol. 67, pp. 1021–1027, Nov. 1991.

Russell, Mark W., et al., "KVLQT 1 mutations in three families with familial or sporadic long QT syndrome", *Human Molecular Genetics*, vol. 5, No. 9, pp. 1319–1324, 1996.

Sanguinetti, M.C., et al., "Coassembly of $K_vLQT1$ and minK (IsK) proteins to form cardiac $I_{Ks}$ potassium channel", *Nature*, vol. 384, pp. 80–83, Nov. 1996.

Schulze–Bahr, E., et al., "KCNE1 mutations cause Jervell and Lange–Nielsen syndrome", *Nature Genetics*, vol. 17, pp. 267–268, Nov. 1997.

Schulze–Bahr, E., et al., "Autosomal recessive long–QT syndrome (Jervell Lange–Nielsen syndrome) is genetically heterogeneous", *Hum Genet*, (1997) 100:573–576.

Shiga, Nobuyuki, and Wangermann, Philine, "Ion selectivity of volume regulatory mechanism present during a hypoosmotic challenge in vestibular dark cells", *Biochimica et Biophysica Acta*, 1240, (1995) 48–54.

Splawski, Igor, et al., "Molecular Basis of the Long–QT Syndrome Associated with Deafness", *The New England Journal of Medicine*, vol. 336, No. 22, pp. 1562–1567, May 1997.

Tanaka, Toshihiro, et al., "Four Novel KVLQT1 and Four Novel HERG Mutations in Familial Long–QT Syndrome", vol. 95, No. 3, pp. 565–567, Feb. 1997.

Tesson, Frédérique, et al., "Exclusion of KCNE1 (IsK) as a Candidate Gene for Jervell and Lang–Nielsen Syndrome", *J. Mol. Cell. Cardiol.*, 28.2051–2055, 1996.

Towbin, Jeffrey A., et al., "Evidence of Genetic Heterogeneity in Romano–Ward Long QT Syndrome", *Circulation*, vol. 90, No. 6, pp. 2635–2644, Dec. 1994.

Tyson, Jessica, et al., "IsK and KvLQT1: mutation in either of the two subunits of the slow component of the delayed rectifier potassium channel can cause Jervell and Lange–Nielsen syndrome", *Human Molecular Genetics*, vol. 6, No. 12, pp. 2179–2185, 1997.

Vincent, G. Michael, "Genetics and Molecular Biology of the Inherited Long QT Syndrome", *Annals of Medicine 26*, pp. 419–425, 1994.

Wang, Ke–Wei, et al., "MinK Residues Line a Potassium Channel Pore", *Neuron*, vol. 16, pp. 571–577, Mar. 1996.

Wang, Ke–Wei, and Goldstein, Steve A..N., "Subunit Composition of MinK Potassium Channels", *Neuron*, vol. 14, pp. 1303–1309, Jun. 1995.

Wang, Qing, et al., "SCN5A Mutations Associated with an Inherited Cardiac Arrhythmia, Long QT Syndrome", *Cell*, vol. 80, pp. 805–811, Mar. 1995.

Wang, Q., et al., "Positional cloning of a novel potassium channel gene: KVLQT1 mutations cause cardiac arrhythmias", *Nature Genetics*, vol. 12, pp. 17–23, Jan. 1996.

Wollnik, Bernd, et al., "Pathophysiological mechanisms of dominant and recessive KLVQT1 $K^+$ channel mutations found in inherited cardiac arrhythmias", *Human Molecular Genetics*, vol. 6, No. 11, pp. 1943–1949, 1997.

Yang, Tao, "$K^+$ Currents and $K^+$ Channel mRNA in Cultured Atrial Cardiac Myocytes (AT–1 Cells)", *Circulation Research*, vol. 75, No. 5, pp. 870–878, Nov. 1994.

Yang, Tao, et al., "Anti–minK Antisense Decreases the Amplitude of the Rapidly Activating Cardiac Delayed Rectifier $K^+$ Current", *Circulation Research*, vol. 77, No. 6, pp. 1246–1253, Dec. 1995.

Yang, Wen–Pin, et al., "KvLQT1, a voltage–gated potassium channel responsible for human cardiac arrhythmias", *Proc. Natl. Acad. Sci. USA*, vol. 94, pp. 4017–4021, Apr. 1997.

```
CTGCCCCCTCCGGCCCCGCCCCGAGCGCCCGGGCTGGCCGGCAGCGGCCCCCGCGGCGGGGCTGGCAGCAGTGGCTGCC-81
CGCACTGCGCCCGGGCGCTCGCCTTCGCTGCAGCTCCCGGTGCCGCCGCTCGGGCCGGCCCCCCGGCAGGCCCTCCTCGTT-162
ATGGCCGCGGCCTCCTCCCCGCCCAGGGCCGAGAGGAAGCGCTGGGGTTGGGGCCGCCTGCCAGGCGCCCGGCGGGGCAGC-243
 M  A  A  A  S  S  P  P  R  A  E  R  K  R  W  G  W  G  R  L  P  G  A  R  R  G  S -27
GCGGGCCTGGCCAAGAAGTGCCCCTTCTCGCTGGAGCTGGCGGAGGGCGGCCCGGCGGGCGGCGCGCTCTACGCGCCCATC-324
 A  G  L  A  K  K  C  P  F  S  L  E  L  A  E  G  G  P  A  G  G  A  L  Y  A  P  I -54
GCGCCCGGCGCCCCAGGTCCCGCGCCCCCTGCGTCCCCGGCCGCGCCCGCCGCGCCCCAGTTGCCTCCGACCTTGGCCCG-405
 A  P  G  A  P  G  P  A  P  P  A  S  P  A  A  P  A  A  P  P  V  A  S  D  L  G  P -81
CGGCCGCCGGTGAGCCTAGACCCGCGCGTCTCCATCTACAGCACGCGCCGCCCGGTGTTGGCGCGCACCCACGTCCAGGGC-486
 R  P  P  V  S  L  D  P  R  V  S  I  Y  S  T  R  R  P  V  L  A  R  T  H  V  Q  G -108
CGCGTCTACAACTTCCTCGAGCGTCCCACCGGCTGGAAATGCTTCGTTTACCACTTCGCCGTCTTCCTCATCGTCCTGGTC-567
 R  V  Y  N  F  L  E  R  P  T  G  W  K  C  F  V  Y  H  F  A  V  F  L  I  V  L  V -135
                                            ▼ S1
TGCCTCATCTTCAGCGTGCTGTCCACCATCGAGCAGTATGCCGCCCTGGCCACGGGGACTCTCTTCTGGATGGAGATCGTG-648
 C  L  I  F  S  V  L  S  T  I  E  Q  Y  A  A  L  A  T  G  T  L  F  W  M  E  I  V -162
                              S2
CTGGTGGTGTTCTTCGGGACGGAGTACGTGGTCCGCCTCTGGTCCGCCGGCTGCCGCAGCAAGTACGTGGGCCTCTGGGGG-729
 L  V  V  F  F  G  T  E  Y  V  V  R  L  W  S  A  G  C  R  S  K  Y  V  G  L  W  G -189
                               ▼
CGGCTGCGCTTTGCCCGGAAGCCCATTTCCATCATCGACCTCATCGTGGTCGTGGCCTCCATGGTGGTCCTCTGCGTGGGC-810
 R  L  R  F  A  R  K  P  I  S  I  I  D  L  I  V  V  V  A  S  M  V  V  L  C  V  G -216
                              ▼   S3
TCCAAGGGGCAGGTGTTTGCCACGTCGGCCATCAGGGGCATCCGCTTCCTGCAGATCCTGAGGATGCTACACGTCGACCGC-891
 S  K  G  Q  V  F  A  T  S  A  I  R  G  I  R  F  L  Q  I  L  R  M  L  H  V  D  R -243
            S4                    ▼
CAGGGAGGCACCTGGAGGCTCCTGGGCTCCGTGGTCTTCATCCACCGCCAGGAGCTGATAACCACCCTGTACATCGGCTTC-972
 Q  G  G  T  W  R  L  L  G  S  V  V  F  I  H  R  Q  E  L  I  T  T  L  Y  I  G  F -270
CTGGGCCTCATCTTCTCCTCGTACTTTGTGTACCTGGCTGAGAAGGACGCGGTGAACGAGTCAGGCCGCGTGGAGTTCGGC-1053
 L  G  L  I  F  S  S  Y  F  V  Y  L  A  E  K  D  A  V  N  E  S  G  R  V  E  F  G -297
         S5                ▼
AGCTACGCAGATGCGCTGTGGTGGGGGGTGGTCACAGTCACCACCATCGGCTATGGGGACAAGGTGCCCCAGACGTGGGTC-1134
 S  Y  A  D  A  L  W  W  G  V  V  T  V  T  T  I  G  Y  G  D  K  V  P  Q  T  W  V -324
                        Pore                              ▼
GGGAAGACCATCGCCTCCTGCTTCTCTGTCTTTGCCATCTCCTTCTTTGCGCTCCCAGCGGGGATTCTTGGCTCGGGGTTT-1215
 G  K  T  I  A  S  C  F  S  V  F  A  I  S  F  F  A  L  P  A  G  I  L  G  S  G  F -351
                                S6                                              ▼
GCCCTGAAGGTGCAGCAGAAGCAGAGGCAGAAGCACTTCAACCGGCAGATCCCGGCGGCAGCCTCACTCATTCAGACCGCA-1296
 A  L  K  V  Q  Q  K  Q  R  Q  K  H  F  N  R  Q  I  P  A  A  A  S  L  I  Q  T  A -378
TGGAGGTGCTATGCTGCCGAGAACCCCGACTCCTCCACCTGGAAGATCTACATCCGGAAGGCCCCCCGGAGCCACACTCTG-1377
 W  R  C  Y  A  A  E  N  P  D  S  S  T  W  K  I  Y  I  R  K  A  P  R  S  H  T  L -405
                                 ▼
CTGTCACCCAGCCCCAAACCCAAGAAGTCTGTGGTGGTAAAGAAAAAAAAGTTCAAGCTGGACAAAGACAATGGGGTGACT-1458
 L  S  P  S  P  K  P  K  K  S  V  V  V  K  K  K  K  F  K  L  D  K  D  N  G  V  T -432
CCTGGAGAGAAGATGCTCACAGTCCCCCATATCACGTGCGACCCCCCAGAAGAGCGGCGGCTGGACCACTTCTCTGTCGAC-1539
 P  G  E  K  M  L  T  V  P  H  I  T  C  D  P  P  E  E  R  R  L  D  H  F  S  V  D -459
              ▼
GGCTATGACAGTTCTGTAAGGAAGAGCCCAACACTGCTGGAAGTGAGCATGCCCCATTTCATGAGAACCAACAGCTTCGCC-1620
 G  Y  D  S  S  V  R  K  S  P  T  L  L  E  V  S  M  P  H  F  M  R  T  N  S  F  A -486
                                              ▼
GAGGACCTGGACCTGGAAGGGGAGACTCTGCTGACACCCATCACCCACATCTCACAGCTGCGGGAACACCATCGGGCCACC-1701
 E  D  L  D  L  E  G  E  T  L  L  T  P  I  T  H  I  S  Q  L  R  E  H  H  R  A  T -513
                                              ▼
ATTAAGGTCATTCGACGCATGCAGTACTTTGTGGCCAAGAAGAAATTCCAGCAAGCGCGGAAGCCTTACGATGTGCGGGAC-1782
 I  K  V  I  R  R  M  Q  Y  F  V  A  K  K  K  F  Q  Q  A  R  K  P  Y  D  V  R  D -540
                                                            ▼
GTCATTGAGCAGTACTCGCAGGGCCACCTCAACCCTCATGGTGCGCATCAAGGAGCTGCAGAGGAGGCTGGACCAGTCCATT-1863
 V  I  E  Q  Y  S  Q  G  H  L  N  L  M  V  R  I  K  E  L  Q  R  R  L  D  Q  S  I -567
```

FIG. 3A

```
                                         ▼
GGGAAGCCCTCACTGTTCATCTCCGTCTCAGAAAAGAGCAAGGATCGCGGCAGCAACACGATCGGCGCCCGCCTGAACCGA-1944
 G  K  P  S  L  F  I  S  V  S  E  K  S  K  D  R  G  S  N  T  I  G  A  R  L  N  R  -594
               ▼
GTAGAAGACAAGGTGACGCAGCTGGACCAGAGGCTGGCACTCATCACCGACATGCTTCACCAGCTGCTCTCCTTGCACGGT-2025
 V  E  D  K  V  T  Q  L  D  Q  R  L  A  L  I  T  D  M  L  H  Q  L  L  S  L  H  G  -621
GGCAGCACCCCCGGCAGCGGCGGCCCCCCCAGAGAGGGCGGGGCCCACATCACCCAGCCCTGCGGCAGTGGCGGCTCCGTC-2106
 G  S  T  P  G  S  G  G  P  P  R  E  G  G  A  H  I  T  Q  P  C  G  S  G  G  S  V  -648
GACCCTGAGCTCTTCCTGCCCAGCAACACCCTGCCCACCTACGAGCAGCTGACCGTGCCCAGGAGGGGCCCCGATGAGGGG-2187
 D  P  E  L  F  L  P  S  N  T  L  P  T  Y  E  Q  L  T  V  P  R  R  G  P  D  E  G  -675
TCCTGAGGAGGGGATGGGGCTGGGGGATGGGCCTGAGTGAGAGGGGAGGCCAAGAGTGGCCCCACCTGGCCCTCTCTGAAG-2268
 S  *                                                                               -676
GAGGCCACCTCCTAAAAGGCCCAGAGAGAAGAGCCCCACTCTCAGAGGCCCCAATACCCCATGGACCATGCTGTCTGGCAC-2349
AGCCTGCACTTGGGGGCTCAGCAAGGCCACCTCTTCCTGGCCGGTGTGGGGGCCCCGTCTCAGGTCTGAGTTGTTACCCCA-2430
AGCGCCCTGGCCCCCACATGGTGATGTTGACATCACTGGCATGGTGGTTGGGACCCAGTGGCAGGGCACAGGGCCTGGCCC-2511
ATGTATGGCCAGGAAGTAGCACAGGCTGAGTGCAGGCCCACCCTGCTTGGCCCAGGGGGCTTCCTGAGGGGAGACAGAGCA-2592
ACCCCTGGACCCCAGCCTCAAATCCAGGACCCTGCCAGGCACAGGCAGGGCAGGACCAGCCCACGCTGACTACAGGGCCAC-2673
CGGCAATAAAAGCCCAGGAGCCCATTTGGAGGGCCTGGGCCTGGCTCCCTCACTCTCAGGAAATGCTGACCCATGGGCAGG-2754
AGACTGTGGAGACTGCTCCTGAGCCCCCAGCTTCCAGCAGGAGGGACAGTCTCACCATTTCCCCAGGGCACGTGGTTGAGT-2835
GGGGGGAACGCCCACTTCCCTGGGTTAGACTGCCAGCTCTTCCTAGCTGGAGAGGAGCCCTGCCTCTCCGCCCCTGAGCCC-2916
ACTGTGCGTGGGGCTCCCGCCTCCAACCCCTCGCCCAGTCCCAGCAGCCAGCCAAACACACAGAAGGGGACTGCCACCTCC-2997
CCTTGCCAGCTGCTGAGCCGCAGAGAAGTGACGGTTCCTACACAGGACAGGGGTTCCTTCTGGGCATTACATCGCATAGAA-3078
ATCAATAATTTGTGGTGATTTGGATCTGTGTTTTAATGAGTTTCACAGTGTGATTTTGATTATTAATTGTGCAAGCTTTTC-3159
CTAATAAACGTGGAGAATCAC(A)n                                                           -3180
```

FIG. 3B

HOMOZYGOUS MUTATION IN KVLQT1 WHICH CAUSES JERVELL AND LANGE NIELSEN SYNDROME

CROSS REFERENCE TO RELATED APPLICATIONS

The present invention is a continuation-in-part of application Ser. No. 08/874,655 filed Jun. 13, 1997. and the present invention is also related to provisional application Ser. No. 60/094,477 filed Jul. 29, 1998, both of which are incorporated herein by reference.

This application was made with Government support under Grant No. Pb 50-HL52338-02 (SCOR), funded by the National Institutes of Health, Bethesda, Md. The federal government may have certain rights in this invention.

BACKGROUND OF THE INVENTION

Jervell and Lange-Nielsen syndrome (JLN) is an autosomal recessive form of long QT syndrome (LQT). In addition to QT interval prolongation, this disorder is associated with congenital deafness. JLN is rare, but affected individuals are susceptible to cardiac arrhythmias with a high incidence of sudden death and short life expectancy. The present invention is directed to a mutation in the KVLQT1 gene which results in Jervell and Lange-Nielsen syndrome and to probes and methods for diagnosing the presence of JLN. JLN is diagnosed in accordance with the present invention by analyzing the DNA sequence of the KVLQT1 gene of an individual to be tested and comparing the respective DNA sequence to the known DNA sequence of a normal KVLQT1 gene.

The publications and other materials used herein to illuminate the background of the invention or provide additional details respecting the practice, are incorporated by reference, and for convenience are respectively grouped in the appended l ist of References.

Cardiac arrhythmias are a common cause of morbidity and mortality, accounting for approximately 11% of all natural deaths (Kannel, 1987; Willich et al., 1987). In general, presymptomatic diagnosis and treatment of individuals with life-threatening ventricular tachyarrhythmias is poor, and in some cases medical management actually increases the risk of arrhythmia and death (Cardiac Arrhythmia Suppression Trial II Investigators, 1992). These factors make early detection of individuals at risk for cardiac arrhythmias and arrhythmia prevention high priorities.

Both genetic and acquired factors contribute to the risk of developing cardiac arrhythmias. Long QT syndrome (LQT) is an inherited cardiac arrhythmia that causes abrupt loss of consciousness, syncope, seizures and sudden death from ventricular tachyarrhythmias, specifically torsade de pointes and ventricular fibrillation (Ward, 1964; Romano, 1965; Schwartz et al., 1975; Moss et al., 1991). This disorder usually occurs in young, otherwise healthy individuals (Ward, 1964; Romano, 1965; Schwartz et al., 1975). Most LQT gene carriers manifest prolongation of the QT interval on electrocardiograms, a sign of abnormal cardiac repolarization (Vincent et al., 1992). The clinical features of LQT result from episodic cardiac arrhythmias, specifically repolarization-related ventricular tachyarrhythmias like torsade de pointes, named for the characteristic undulating nature of the electrocardiogram in this arrhythmia and ventricular fibrillation (Schwartz et al., 1975; Moss and McDonald, 1971). Torsade de pointes may degenerate into ventricular fibrillation, a particularly lethal arrhythmia. Although LQT is not a common diagnosis, ventricular arrhythmias are very common; more than 300,000 United States citizens die suddenly every year (Kannel, et al., 1987; Willich et al., 1987) and, in many cases, the underlying mechanism may be aberrant cardiac repolarization. LQT, therefore, provides a unique opportunity to study life-threatening cardiac arrhythmias at the molecular level.

Both inherited and acquired forms of LQT have been defined. Acquired LQT and secondary arrhythmias can result from cardiac ischemia, bradycardia and metabolic abnormalities such as low serum potassium or calcium concentration (Zipes, 1987). LQT can also result from treatment with certain medications, including antibiotics, antihistamines, general anesthetics, and, most commonly, antiarrhythmic medications (Zipes, 1987). Inherited forms of LQT can result from mutations in at least five different genes. In previous studies, LQT loci were mapped to chromosome 11p15.5 (KVLQT1 or LQT1) (Keating et al., 1991a; Keating et al., 1991b), 7q35–36 (HERG or LQT2), 3p21–24 (SCN5A or LQT3) (Jiang et al., 1994). Of these, the most common cause of inherited LQT is KVLQT1. Our data indicate that mutations in this gene are responsible for more than 50% of inherited LQT. Recently, a fourth LQT locus (LQT4) was mapped to 4q25–27 (Schott et al., 1995). Also, KCNE1 (LQT5) has been associated with long QT syndrome (Splawski et al., 1997b; Duggal et al., 1998). These genes encode ion channels involved in generation of the cardiac action potential. Mutations can lead to channel dysfunction and delayed myocellular repolarization. Because of regional heterogeneity of channel expression with the myocardium, the aberrant cardiac repolarization creates a substrate for arrhythmia. KVLQT1 and KCNE1 are also expressed in the inner ear (Neyroud et al., 1997; Vetter et al., 1996). We and others demonstrated that homozygous or compound heterozygous mutations in each of these genes can cause deafness and the severe cardiac phenotype of the Jervell and Lange-Nielsen syndrome (Neyroud et al., 1997; Splawski et al., 1997a; Schultze-Bahr et al., 1997; Tyson et al., 1997). Loss of functional channels in the ear apparently disrupts the production of endolymph, leading to deafness.

Autosomal dominant and autosomal recessive forms of this disorder have been reported. Autosomal recessive LQT (also known as Jervell and Lange-Nielsen syndrome) has been associated with congenital neural deafness; this form of LQT is rare (Jervell and Lange-Nielsen, 1957). Autosomal dominant LQT (Romano-Ward syndrome) is more common, and is not associated with other phenotypic abnormalities (Romano et al., 1963; Ward, 1964). A disorder very similar to inherited LQT can also be acquired, usually as a result of pharmacologic therapy (Schwartz et al., 1975; Zipes, 1987).

The data have implications for the mechanism of arrhythmias in LQT. Two hypotheses for LQT have previously been proposed (Schwartz et al., 1994). One suggests that a predominance of left autonomic innervation causes abnormal cardiac repolarization and arrhythmias. This hypothesis is supported by the finding that arrhythmias can be induced in dogs by removal of the right stellate ganglion. In addition, anecdotal evidence suggests that some LQT patients are effectively treated by β-adrenergic blocking agents and by left stellate ganglionectomy (Schwartz et al., 1994). The second hypothesis for LQT-related arrhythmias suggests that mutations in cardiac-specific ion channel genes, or genes that modulate cardiac ion channels, cause delayed myocellular repolarization. Delayed myocellular repolarization could promote reactivation of L-type calcium channels, resulting in secondary depolarizations (January and Riddle, 1989). These secondary depolarizations are the likely cellular mechanism of torsade de pointes arrhythmias (Surawicz, 1989). This hypothesis is supported by the observation that pharmacologic block of potassium channels can induce QT prolongation and repolarization-related arrhythmias in humans and animal models (Antzelevitch and Sicouri, 1994). The discovery that one form of LQT results from mutations in a cardiac potassium channel gene supports the myocellular hypothesis.

In theory, mutations in a cardiac sodium channel gene could cause LQT. Voltage-gated sodium channels mediate rapid depolarization in ventricular myocytes, and also conduct a small current during the plateau phase of the action potential (Attwell et al., 1979). Subtle abnormalities of sodium channel function (e.g., delayed sodium channel inactivation or altered voltage-dependence of channel inactivation) could delay cardiac repolarization, leading to QT prolongation and arrhythmias. In 1992, Gellens and colleagues cloned and characterized a cardiac sodium channel gene, SCN5A (Gellens et al., 1992). The structure of this gene was similar to other, previously characterized sodium channels, encoding a large protein of 2016 amino acids. These channel proteins contain four homologous domains (DI–DIV), each of which contains six putative membrane spanning segments (S1–S6). SCN5A was recently mapped to chromosome 3p21, making it an excellent candidate gene for LQT3 (George et al., 1995), and this gene was then proved to be associated with LQT3 (Wang et al., 1995).

In 1994, Warmke and Ganetzky identified a novel human cDNA, human ether a-go-go related gene (HERG, Warmke and Ganetzky, 1994). HERG was localized to human chromosome 7 by PCR analysis of a somatic cell hybrid panel (Warmke and Ganetzky, 1994) making it a candidate for LQT2. It has predicted amino acid sequence homology to potassium channels. HERG was isolated from a hippocampal cDNA library by homology to the Drosophila ether a-go-go gene (eag), which encodes a calcium-modulated potassium channel (Bruggemann et al., 1993). HERG is not the human homolog of eag, however, sharing only ~50% amino acid sequence homology. HERG has been shown to be associated with LQT2 (Curran et al., 1995).

LQT1 was found to be linked with the gene KVLQT1 (Q. Wang et al., 1996). Sixteen families with mutations in KVLQT1 were identified and characterized and it was shown that in all sixteen families there was complete linkage between LQT1 and KVLQT1. KVLQT1 was mapped to chromosome 11p15.5 making it a candidate gene for LQT1. KVLQT1 encodes a protein with structural characteristics of potassium channels, and expression of the gene as measured by Northern blot analysis demonstrated that KVLQT1 is most strongly expressed in the heart. One intragenic deletion and ten different missense mutations which cause LQT were identified in KVLQT1. These data define KVLQT1 as a novel cardiac potassium channel gene and show that mutations in this gene cause susceptibility to ventricular tachyarrhythmias and sudden death.

It was known that one component of the $I_{Ks}$ channel is minK, a 130 amino acid protein with a single putative transmembrane domain (Takumi et al., 1988; Goldstein and Miller, 1991; Hausdorff et al., 1991; Takumi et al., 1991; Busch et al., 1992; Wang and Goldstein, 1995; KW Wang et al., 1996). The size and structure of this protein made it unlikely that minK alone forms functional channels (Attali et al., 1993; Lesage et al., 1993). It has been shown that KVLQT1 and minK coassemble to form the cardiac $I_{Ks}$ potassium channel (Sanguinetti et al., 1996; Barhanin et al., 1996). $I_{Ks}$ dysfunction is a cause of cardiac arrhythmia. It was later shown that mutations in KCNE1 (which encodes minK) also can result in LQT (Splawski et al., 1997b).

In 1957, Jervell and Lange-Nielsen reported a syndrome associated with congenital sensory deafness and prolonged QT interval in four children of a Norwegian family (Jervell and Lange-Nielsen, 1957). The affected children had multiple syncopal episodes and three died suddenly at ages 4, 5 and 9. Since 1957, other examples of long QT syndrome (LQT) associated with deafness (Jervell and Lange-Nielsen syndrome or JLN) have been described (Fraser et al., 1964; Jervell et al., 1966; Tesson et al., 1996). In all cases the apparent mode of inheritance was autosomal recessive. This syndrome is rare (estimated incidence of 1.6 to 6 per million) (Fraser et al., 1964). Affected individuals are susceptible to recurrent syncope with a high incidence of sudden death and short life expectancy. Syncope results from torsade de pointes ventricular tachycardia and ventricular fibrillation (Till et al., 1988; Holland, 1993).

Romano-Ward syndrome is the autosomal dominant form of LQT and is not associated with deafness or other phenotypic abnormalities (Romano et al., 1963; Ward, 1964). The incidence of Romano-Ward is higher than JLN, but affected individuals generally have milder symptoms (Moss et al., 1985; Moss et al., 1991).

We hypothesized that JLN results from mutations affecting both alleles of an autosomal dominant LQT gene. It is here demonstrated that homozygous mutation of KVLQT1 causes JLN. Other family members also had LQT with an autosomal dominant pattern of inheritance but these individuals had normal hearing and were heterozygotes.

SUMMARY OF THE INVENTION

The present invention demonstrates a molecular basis of Jervell and Lange-Nielsen syndrome. More specifically, the present invention has determined that homozygous mutations in the KVLQT1 gene cause JLN. Genotypic analyses were performed on 58 members of a JLN family. Analysis of the KVLQT1 gene will provide an early diagnosis of subjects with JLN. The diagnostic method comprises analyzing the DNA sequence of the KVLQT1 gene of an individual to be tested and comparing it with the DNA sequence of the native, non-variant gene. In a second embodiment. the KVLQT1 gene of an individual to be tested is screened for mutations which cause LQT.

BRIEF DESCRIPTION OF THE FIGURES

FIG. 2A shows a subset of kindred 2948. Symbols are as described in the legend for FIG. 1. Note that the abnormal SSCP band cosegregates with the LQT phenotype in this family. FIG. 2B shows the DNA and protein sequence of the normal and mutant KVLQT1 alleles. The mutant allele contains a single G insertion after nucleotide 729 of SEQ ID NO:1 (or after base number 567 of the coding region numbering from the A nucleotide of the ATG initiation). The insertion causes a frameshift leading to a premature stop codon. The normal DNA sequence is shown as SEQ ID NO:73, the normal peptide sequence is SEQ ID NO:74, the mutant DNA sequence is SEQ ID NO:75 and the mutant peptide sequence is SEQ ID NO:76.

FIGS. 3A–3B. Genomic organization of KVLQT1 coding and 5' and 3' untranslated regions. Positions of the introns are indicated with arrowheads. The six putative transmembrane segments (S1 to S6) and the putative pore region (Pore) are underlined. The stop codon is denoted by an asterisk. The nucleotide sequence of FIGS. 3A–3B is SEQ ID NO:1. The amino acid sequence of FIGS. 3A–3B is SEQ ID NO:2.

BRIEF DESCRIPTION OF THE SEQUENCE LISTING

Figure 1:
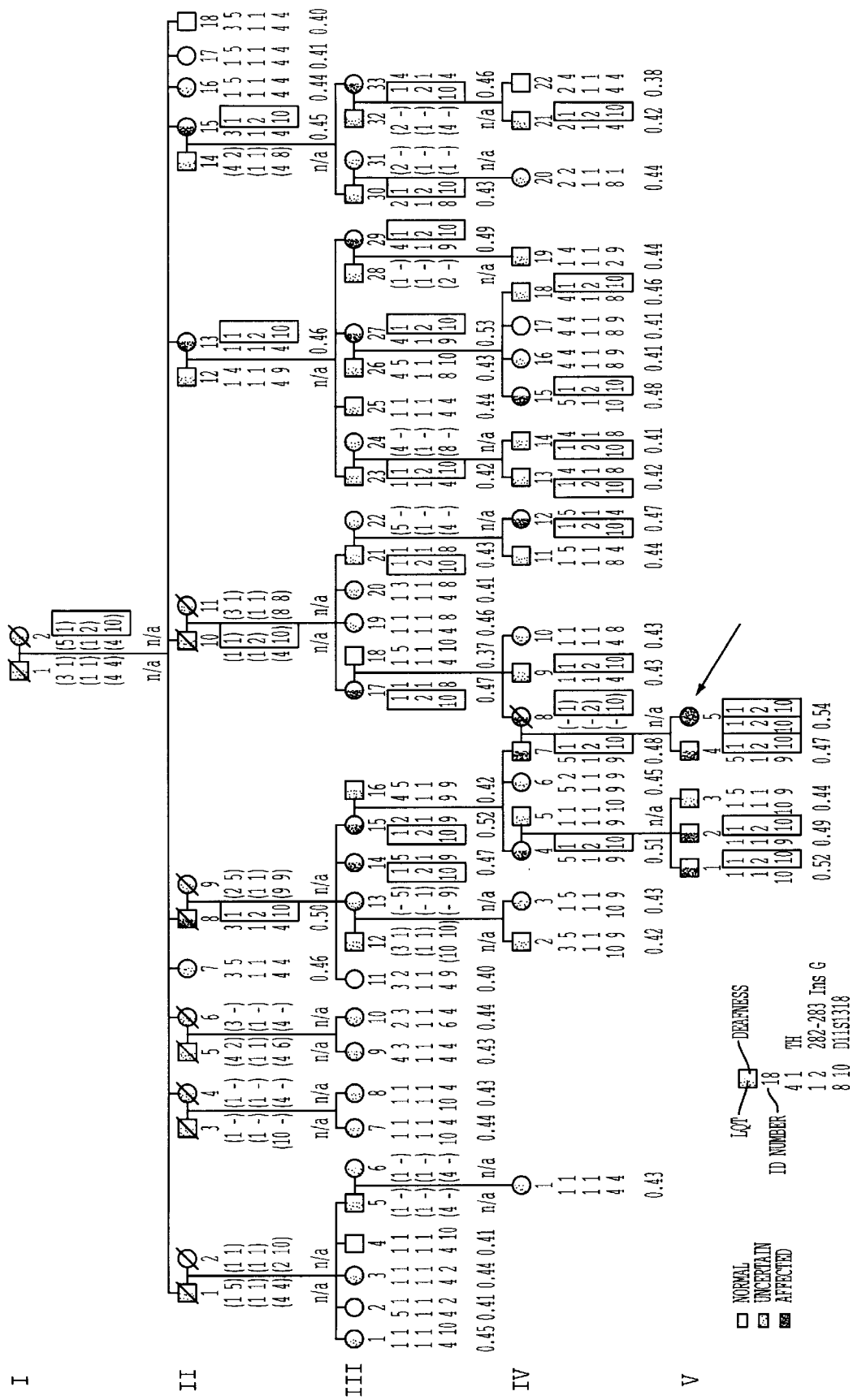
FIG. 1. JLN kindred 2948 with genotypes showing linkage between KVLQT1 and the LQT phenotype. Individuals are represented by circles (females) or squares (males). The left side of the symbol indicates long-QT syndrome phenotype; the right side denotes hearing status. Black=affected; gray=uncertain; white=unaffected. The proband (long-QT syndrome and deafness) is indicated by a completely filled circle and by an arrow. Genotypes for the polymorphic markers TH and D11S1318, and KVLQT1 mutation are shown beneath each symbol. For KVLQT1 the normal allele is designated by 1 and mutant allele by 2. Inferred genotypes are bracketed. Long-QT syndrome-associated genotypes are indicated by a box. QTc intervals are shown below genotypes. Ages of individuals in years were: II-7, 73; II-8, 82; II-13, 69; II-15, 66; II-16, 64; II-17, 61; II-18, 58; III-1, 59; III-2, 57; III-3, 52; III-4, 45; III-7, 52; III-8, 50; III-9, 55; III-10, 43; III-11, 62; III-14, 56; III-15, 58; III-17, 43; III-19, 48; III-20, 46; III-21, 39; III-23, 48; III-25, 45; III-27, 34; III-29, 32; III-30, 45; III-33, 43; IV-1, 22; IV-2, 36; IV-3, 27; IV-4, 33; IV-6, 29; IV-7, 27; IV-9, 24; IV-10, 19; IV-11, 20; IV-12, 18; IV-13, 25; IV-14, 23; IV-15, 14; IV-16, 12; IV-17, 10; IV-18, 8; IV-19, 13; IV-20, 26; IV-21, 22; IV-22, 17; V-1, 9; V-2, 6; V-3, 4; V-4, 3; and V-5, 13 months. Note that the KVLQT1 mutant allele cosegregates with the long-QT syndrome phenotype in this family and that the JLN patient V-5 is homozygous for the mutation.

SEQ ID NO:1 is the wild-type cDNA for KVLQT1 including 5' and 3' untranslated regions (see FIGS. 3A–B).
SEQ ID NO:2 is the wild-type KVLQT1 protein (see FIGS. 3A–B).
SEQ ID NOs:3–4 are hypothetical nucleic acids used to demonstrate the calculation of percent homology or identity.
SEQ ID NO:5 is a mutated KVLQT1 with a G (base 730) inserted after base 729 of the wild-type.
SEQ ID NO:6 is a polypeptide encoded by the mutated KVLQT1 of SEQ ID NO:5.
SEQ ID NOs:7–38 are the exon/intron boundaries of KVLQT1 (Table 4).
SEQ ID NOs:39–72 are primers used to amplify exons of KVLQT1 (Table 5).
SEQ ID NO:73 is the normal nucleic acid shown in FIG. 2B.
SEQ ID NO:74 is the normal peptide shown in FIG. 2B.
SEQ ID NO:75 is the mutant nucleic acid shown in FIG. 2B.
SEQ ID NO:76 is the mutant peptide shown in FIG. 2B.
SEQ ID NO:77 is wild-type KCNE1.
SEQ ID NO:78 is wild-type minK encoded by SEQ ID NO:77.

DETAILED DESCRIPTION OF THE INVENTION

The present invention is directed to the determination that JLN maps to the KVLQT1 gene and that molecular variants of this gene cause or are involved in the pathogenesis of JLN. More specifically, the present invention relates to a mutation in the KVLQT1 gene and its use in the diagnosis of LQT. The present invention is further directed to methods of screening humans for the presence of KVLQT1 gene variants which cause JLN. The present invention is also directed to methods for screening for drugs useful in treating or preventing JLN.

The present invention provides methods of screening the KVLQT1 gene to identify mutations. Such methods may further comprise the step of amplifying a portion of the KVLQT1 gene, and may further include a step of providing a set of polynucleotides which are primers for amplification of said portion of the KVLQT1 gene. The method is useful for identifying mutations for use in either diagnosis of JLN or prognosis of JLN.

Proof that the KVLQT1 gene is involved in causing JLN is obtained by finding sequences in DNA extracted from affected kindred members which create abnormal KVLQT1 gene products or abnormal levels of the gene products. Such JLN susceptibility alleles will co-segregate with the disease in large kindreds. They will also be present at a much higher frequency in non-kindred individuals with JLN than in individuals in the general population. The key is to find mutations which are serious enough to cause obvious disruption to the normal function of the gene product. These mutations can take a number of forms. The most severe forms would be frame shift mutations or large deletions which would cause the gene to code for an abnormal protein or one which would significantly alter protein expression. Less severe disruptive mutations would include small in-frame deletions and nonconservative base pair substitutions which would have a significant effect on the protein produced, such as changes to or from a cysteine residue, from a basic to an acidic amino acid or vice versa, from a hydrophobic to hydrophilic amino acid or vice versa, or other mutations which would affect secondary or tertiary protein structure. Silent mutations or those resulting in conservative amino acid substitutions would not generally be expected to disrupt protein function.

According to the diagnostic and prognostic method of the present invention, alteration of the wild-type KVLQT1 gene is detected. In addition, the method can be performed by detecting the wild-type KVLQT1 gene and confirming the lack of a cause of JLN as a result of this locus. "Alteration of a wild-type gene" encompasses all forms of mutations including deletions, insertions and point mutations in the coding and noncoding regions. Deletions may be of the entire gene or of only a portion of the gene. Point mutations may result in stop codons, frameshift mutations or amino acid substitutions. Somatic mutations are those which occur only in certain tissues and are not iinerited in the germline. Germline mutations can be found in any of a body's tissues and are inherited. Point mutational events may occur in regulatory regions, such as in the promoter of the gene, leading to loss or diminution of expression of the mRNA. Point mutations may also abolish proper RNA processing, leading to loss of expression of the KVLQT1 gene product, or to a decrease in mRNA stability or translation efficiency.

Useful diagnostic techniques include, but are not limited to fluorescent in situ hybridization (FISH), direct DNA sequencing, PFGE analysis, Southern blot analysis, single stranded conformation analysis (SSCA), RNase protection assay, allele-specific oligonucleotide (ASO), dot blot analysis and PCR-SSCP, as discussed in detail further below. Also useful is the recently developed technique of DNA microchip technology.

The presence of JLN may be ascertained by testing any tissue of a human for mutations of the KVLQT1 gene. For example, a person who has inherited a homozygous germline KVLQT1 mutation would be prone to develop JLN. This can be determined by testing DNA from any tissue of the person's body. Most simply, blood can be drawn and DNA extracted from the cells of the blood. In addition, prenatal diagnosis can be accomplished by testing fetal cells, placental cells or amniotic cells for mutations of the KVLQT1 gene. Alteration of a wild-type KVLQT1 allele, whether, for example, by point mutation or deletion, can be detected by any of the means discussed herein.

There are several methods that can be used to detect DNA sequence variation. Direct DNA sequencing, either manual sequencing or automated fluorescent sequencing can detect sequence variation. Another approach is the single-stranded conformation polymorphism assay (SSCP) (Orita et al., 1989). This method does not detect all sequence changes, especially if the DNA fragment size is greater than 200 bp, but can be optimized to detect most DNA sequence variation. The reduced detection sensitivity is a disadvantage, but the increased throughput possible with SSCP makes it an attractive, viable alternative to direct sequencing for mutation detection on a research basis. The fragments which have shifted mobility on SSCP gels are then sequenced to determine the exact nature of the DNA sequence variation. Other approaches based on the detection of mismatches between the two complementary DNA strands include clamped denaturing gel electrophoresis (CDGE) (Sheffield et al., 1991), hetcroduplex analysis (HA) (White et al., 1992) and chemical mismatch cleavage (CMC) (Grompe et al., 1989). None of the methods described above will detect large deletions, duplications or insertions, nor will they detect a regulatory mutation which affects transcription or translation of the protein. Other methods which might detect these classes of mutations such as a protein truncation assay or the asymmetric assay, detect only specific types of mutations and would not detect missense mutations. A review of currently available methods of detecting DNA sequence variation can be found in a recent review by Grompe (1993). Once a mutation is known, an allele specific detection approach such as allele specific oligonucleotide (ASO) hybridization can be utilized to rapidly screen large numbers of other samples for that same mutation. Such a technique can utilize probes which are labeled with gold nanoparticles to yield a visual color result (Elghanian et al., 1997).

A rapid preliminary analysis to detect polymorphisms in DNA sequences can be performed by looking at a series of Southern blots of DNA cut with one or more restriction enzymes, preferably with a large number of restriction enzymes. Each blot contains a series of normal individuals and a series of LQT cases. Southern blots displaying hybridizing fragments (differing in length from control DNA when probed with sequences near or including the KVLQT1 locus) indicate a possible mutation. If restriction enzymes which produce very large restriction fragments are used, then pulsed field gel electrophoresis (PFGE) is employed.

Detection of point mutations may be accomplished by molecular cloning of the KVLQT1 allele and sequencing the allele using techniques well known in the art. Also, the gene or portions of the gene may be amplified, e.g., by PCR or other amplification technique, and the amplified gene or amplified portions of the gene may be sequenced.

There are six well known methods for a more complete, yet still indirect, test for confirming the presence of a susceptibility allele: 1) single stranded conformation analysis (SSCP) (Orita et al., 1989); 2) denaturing gradient gel electrophoresis (DGGE) (Wartell et al., 1990; Sheffield et al., 1989); 3) RNase protection assays (Finkelstein et al., 1990; Kinszler et al., 1991); 4) allele-specific oligonucleotides (ASOs) (Conner et al., 1983); 5) the use of proteins which recognize nucleotide mismatches, such as the *E. coli* mutS protein (Modrich, 1991); and 6) allele-specific PCR (Ruano and Kidd, 1989). For allele-specific PCR, primers are used which hybridize at their 3' ends to a particular KVLQT1 mutation. If the particular mutation is not present, an amplification product is not observed. Amplification Refractory Mutation System (ARMS) can also be used, as disclosed in European Patent Application Publication No. 0332435 and in Newton et al., 1989. Insertions and deletions of genes can also be detected by cloning, sequencing and amplification. In addition, restriction fragment length polymorphism (RFLP) probes for the gene or surrounding marker genes can be used to score alteration of an allele or an insertion in a polymorphic fragment. Such a method is particularly useful for screening relatives of an affected individual for the presence of the mutation found in that individual. Other techniques for detecting insertions and deletions as known in the art can be used.

In the first three methods (SSCP, DGGE and RNase protection assay), a new electrophoretic band appears. SSCP detects a band which migrates differentially because the sequence change causes a difference in single-strand, intramolecular base pairing. RNase protection involves cleavage of the mutant polynucleotide into two or more smaller fragments. DGGE detects differences in migration rates of mutant sequences compared to wild-type sequences, using a denaturing gradient gel. In an allele-specific oligonucleotide assay, an oligonucleotide is designed which detects a specific sequence, and the assay is performed by detecting the presence or absence of a hybridization signal. In the mutS assay, the protein binds only to sequences that contain a nucleotide mismatch in a heteroduplex between mutant and wild-type sequences.

Mismatches, according to the present invention, are hybridized nucleic acid duplexes in which the two strands are not 100% complementary. Lack of total homology may be due to deletions, insertions, inversions or substitutions. Mismatch detection can be used to detect point mutations in the gene or in its mRNA product. While these techniques are less sensitive than sequencing, they are simpler to perform on a large number of samples. An example of a mismatch cleavage technique is the RNase protection method. In the practice of the present invention, the method involves the use of a labeled riboprobe which is complementary to the human wild-type KVLQT1 gene coding sequence. The riboprobe and either mRNA or DNA isolated from the person are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full length duplex RNA for the riboprobe and the mRNA or DNA. The riboprobe need not be the full length of the mRNA or gene but can be a segment of either. If the riboprobe comprises only a segment of the mRNA or gene, it will be desirable to use a number of these probes to screen the whole mRNA sequence for mismatches.

In similar fashion, DNA probes can be used to detect mismatches, through enzymatic or chemical cleavage. See, e.g., Cotton el al., 1988; Shenk et al., 1975; Novack et al., 1986. Alternatively, mismatches can be detected by shifts in the electrophoretic mobility of mismatched duplexes relative to matched duplexes. See, e.g., Cariello, 1988. With either riboprobes or DNA probes, the cellular mRNA or DNA which might contain a mutation can be amplified using PCR (see below) before hybridization. Changes in DNA of the KVLQT1 gene can also be detected using Southern hybridization, especially if the changes are gross rearrangements, such as deletions and insertions.

DNA sequences of the KVLQT1 gene which have been amplified by use of PCR may also be screened using allele-specific probes. These probes are nucleic acid oligomers, each of which contains a region of the gene sequence harboring a known mutation. For example, one oligomer may be about 30 nucleotides in length, corresponding to a portion of the gene sequence. By use of a battery of such allele-specific probes, PCR amplification products can be screened to identify the presence of a previously identified mutation in the gene. Hybridization of allele-specific probes with amplified KVLQT1 sequences can be performed, for example, on a nylon filter. Hybridization to a particular probe under high stringency hybridization conditions indicates the presence of the same mutation in the tissue as in the allele-specific probe.

The newly developed technique of nucleic acid analysis via microchip technology is also applicable to the present invention. In this technique, literally thousands of distinct oligonucleotide probes are built up in an array on a silicon chip. Nucleic acid to be analyzed is fluorescently labeled and hybridized to the probes on the chip. It is also possible to study nucleic acid-protein interactions using these nucleic acid microchips. Using this technique one can determine the presence of mutations or even sequence the nucleic acid being analyzed or one can measure expression levels of a gene of interest. The method is one of parallel processing of many, even thousands, of probes at once and can tremendously increase the rate of analysis. Several papers have been published which use this technique. Some of these are Hacia et al., 1996; Shoemaker et al., 1996; Chee et al., 1996; Lockhart et al., 1996; DeRisi et al., 1996; Lipshutz et al., 1995. This method has already been used to screen people for mutations in the breast cancer gene BRCA1 (Hacia et al., 1996). This new technology has been reviewed in a news article in Chemical and Engineering News (Borman, 1996) and been the subject of an editorial (Editorial, Nature Genetics, 1996). Also see Fodor (1997).

The most definitive test for mutations in a candidate locus is to directly compare genomic KVLQT1 sequences from patients with those from a control population. Alternatively, one could sequence messenger RNA after amplification, e.g., by PCR, thereby eliminating the necessity of determining the exon structure of the candidate gene.

Mutations from patients falling outside the coding region of KVLQT1 can be detected by examining the non-coding regions, such as introns and regulatory sequences near or within the genes. An early indication that mutations in noncoding regions are important may come from Northern blot experiments that reveal messenger RNA molecules of abnormal size or abundance in patients as compared to control individuals.

Alteration of KVLQT1 mRNA expression can be detected by any techniques known in the art. These include Northern blot analysis, PCR amplification and RNase protection. Diminished mRNA expression indicates an alteration of the wild-type gene. Alteration of wild-type genes can also be detected by screening for alteration of wild-type KVLQT1 protein. For example, monoclonal antibodies immunoreactive with KVLQT1 can be used to screen a tissue. Lack of cognate antigen would indicate a mutation. Antibodies specific for products of mutant alleles could also be used to detect mutant gene product. Such immunological assays can be done in any convenient formats known in the art. These include Western blots, immunohistochemical assays and ELISA assays. Any means for detecting an altered KVLQT1 protein can be used to detect alteration of the wild-type KVLQT1 gene. Functional assays, such as protein binding determinations, can be used. In addition, assays can be used which detect KVLQT1 biochemical function. Finding a mutant KVLQT1 gene product indicates alteration of a wild-type KVLQT1 gene.

A mutant KVLQT1 gene or gene product can also be detected in other human body samples, such as serum, stool, urine and sputum. The same techniques discussed above for detection of mutant genes or gene products in tissues can be applied to other body samples. By screening such body samples, a simple early diagnosis can be achieved for LQT or JLN.

The primer pairs of the present invention are useful for determination of the nucleotide sequence of a particular KVLQT1 allele using PCR. The pairs of single-stranded DNA primers for KVLQT1 can be annealed to sequences within or surrounding the KVLQT1 gene on chromosome 11 in order to prime amplifying DNA synthesis of the gene itself. A complete set of these primers allows synthesis of all of the nucleotides of the gene coding sequences, i.e., the exons. The set of primers preferably allows synthesis of both intron and exon sequences. Allele-specific primers can also be used. Such primers anneal only to particular KVLQT1 mutant alleles, and thus will only amplify a product in the presence of the mutant allele as a template.

In order to facilitate subsequent cloning of amplified sequences, primers may have restriction enzyme site sequences appended to their 5' ends. Thus, all nucleotides of the primers are derived from KVLQT1 sequence or sequences adjacent to KVLQT1, except for the few nucleotides necessary to form a restriction enzyme site. Such enzymes and sites are well known in the art. The primers themselves can be synthesized using techniques which are well known in the art. Generally, the primers can be made using oligonucleotide synthesizing machines which are commercially available. Given the sequence of KVLQT1, design of particular primers is well within the skill of the art. The present invention adds to this by presenting data on the intron/exon boundaries thereby allowing one to design primers to amplify and sequence all of the exonic regions completely.

The nucleic acid probes provided by the present invention are useful for a number of purposes. They can be used in Southern hybridization to genomic DNA and in the RNase protection method for detecting point mutations already discussed above. The probes can be used to detect PCR amplification products. They may also be used to detect mismatches with the KVLQT1 gene or mRNA using other techniques.

It has been discovered that individuals with the wild-type KVLQT1 gene do not have LQT. However, mutations which interfere with the function of the KVLQT1 gene product are involved in the pathogenesis of JLN. Thus, the presence of an altered (or a mutant) KVLQT1 gene which produces a protein having a loss of function, or altered function, directly causes JLN which increases the risk of cardiac arrhythmias. In order to detect a KVLQT1 gene mutation, a biological sample is prepared and analyzed for a difference between the sequence of the allele being analyzed and the sequence of the wild-type allele. Mutant KVLQT1 alleles can be initially identified by any of the techniques described above. The mutant alleles are then sequenced to identify the specific mutation of the particular mutant allele. Alternatively, mutant alleles can be initially identified by identifying mutant (altered) proteins, using conventional techniques. The mutant alleles are then sequenced to identify the specific mutation for each allele. The mutations, especially those which lead to an altered function of the protein, are then used for the diagnostic and prognostic methods of the present invention.

Definitions

The present invention employs the following definitions:

"Amplification of Polynucleotides" utilizes methods such as the polymerase chain reaction (PCR), ligation amplification (or ligase chain reaction, LCR) and amplification methods based on the use of Q-beta replicase. Also useful are strand displacement amplification (SDA), thermophilic SDA, and nucleic acid sequence based amplification (3SR or NASBA). These methods are well known and widely practiced in the art. See, e.g., U.S. Pat. Nos. 4,683,195 and 4,683,202 and Innis et al., 1990 (for PCR); Wu and Wallace, 1989 (for LCR); U.S. Pat. Nos. 5,270,184 and 5,455,166 and Walker et al., 1992 (for SDA); Spargo et al., 1996 (for thermophilic SDA) and U.S. Pat. No. 5,409,818, Fahy et al., 1991 and Compton, 1991 for 3SR and NASBA. Reagents and hardware for conducting PCR are commercially available. Primers useful to amplify sequences from the KVLQT1 region are preferably complementary to, and hybridize specifically to sequences in the KVLQT1 region or in regions that flank a target region therein. KVLQT1 sequences generated by amplification may be sequenced directly. Alternatively, but less desirably, the amplified sequence(s) may be cloned prior to sequence analysis. A method for the direct cloning and sequence analysis of enzymatically amplified genomic segments has been described by Scharf et al., 1986.

"Analyte polynucleotide" and "analyte strand" refer to a single- or double-stranded polynucleotide which is suspected of containing a target sequence, and which may be present in a variety of types of samples, including biological samples.

"Antibodies." The present invention also provides polyclonal and/or monoclonal antibodies and fragments thereof, and immunologic binding equivalents thereof, which are capable of specifically binding to the KVLQT1 polypeptide and fragments thereof or to polynucleotide sequences from the KVLQT1 region. The term "antibody" is used both to refer to a homogeneous molecular entity, or a mixture such as a serum product made up of a plurality of different molecular entities. Polypeptides may be prepared synthetically in a peptide synthesizer and coupled to a carrier molecule (e.g., keyhole limpet hemocyanin) and injected over several months into rabbits. Rabbit sera is tested for immunoreactivity to the KVLQT1 polypeptide or fragment. Monoclonal antibodies may be made by injecting mice with the protein polypeptides, fusion proteins or fragments thereof. Monoclonal antibodies will be screened by ELISA and tested for specific immunoreactivity with KVLQT1 polypeptide or fragments thereof. See, Harlow and Lane, 1988. These antibodies will be useful in assays as well as pharmaceuticals.

Once a sufficient quantity of desired polypeptide has been obtained, it may be used for various purposes. A typical use is the production of antibodies specific for binding. These antibodies may be either polyclonal or monoclonal, and may be produced by in vitro or in vivo techniques well known in the art. For production of polyclonal antibodies, an appropriate target immune system, typically mouse or rabbit, is selected. Substantially purified antigen is presented to the immune system in a fashion determined by methods appropriate for the animal and by other parameters well known to immunologists. Typical sites for injection are in footpads, intramuscularly, intraperitoneally, or intradermally. Of course, other species may be substituted for mouse or rabbit. Polyclonal antibodies are then purified using techniques known in the art, adjusted for the desired specificity.

An immunological response is usually assayed with an immunoassay. Normally, such immunoassays involve some purification of a source of antigen, for example, that produced by the same cells and in the same fashion as the antigen. A variety of immunoassay methods are well known in the art. See, e.g., Harlow and Lane, 1988, or Goding, 1986.

Monoclonal antibodies with affinities of $10^{-8}$ $M^{-1}$ or preferably $10^{-9}$ to $10^{-10}$ $M^{-1}$ or stronger will typically be made by standard procedures as described, e.g., in Harlow and Lane, 1988 or Goding, 1986. Briefly, appropriate animals will be selected and the desired immunization protocol followed. After the appropriate period of time, the spleens of such animals are excised and individual spleen cells fused, typically, to immortalized myeloma cells under appropriate selection conditions. Thereafter, the cells are clonally separated and the supernatants of each clone tested for their production of an appropriate antibody specific for the desired region of the antigen.

Other suitable techniques involve in vitro exposure of lymphocytes to the antigenic polypeptides, or alternatively, to selection of libraries of antibodies in phage or similar vectors. See Huse et al., 1989. The polypeptides and antibodies of the present invention may be used with or without modification. Frequently, polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent agents, chemiluminescent agents, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced (see U.S. Pat. No. 4,816,567).

"Binding partner" refers to a molecule capable of binding a ligand molecule with high specificity, as for example, an antigen and an antigen-specific antibody or an enzyme and its inhibitor. In general, the specific binding partners must bind with sufficient affinity to immobilize the analyte copy/complementary strand duplex (in the case of polynucleotide hybridization) under the isolation conditions. Specific binding partners are known in the art and include, for example, biotin and avidin or streptavidin, IgG and protein A, the numerous, known receptor-ligand couples, and complementary polynucleotide strands. In the case of complementary polynucleotide binding partners, the partners are normally at least about 15 bases in length, and may be at least 40 bases in length. It is well recognized by those of skill in the art that lengths shorter than 15 (e.g., 8 bases), between 15 and 40, and greater than 40 bases may also be used. The polynucleotides may be composed of DNA, RNA, or synthetic nucleotide analogs. Further binding partners can be identified using, e.g., the two-hybrid yeast screening assay as described herein.

A "biological sample" refers to a sample of tissue or fluid suspected of containing an analyte polynucleotide or polypeptide from an individual including, but not limited to, e.g., plasma, serum, spinal fluid, lymph fluid, the external sections of the skin, respiratory, intestinal, and genitourinary tracts, tears, saliva, blood cells, tumors, organs, tissue and samples of in vitro cell culture constituents.

"Encode". A polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

"Isolated" or "substantially pure". An "isolated" or "substantially pure" nucleic acid (e.g., an RNA, DNA or a mixed polymer) is one which is substantially separated from other cellular components which naturally accompany a native human sequence or protein, e.g., ribosomes, polymerases, many other human genome sequences and proteins. The term embraces a nucleic acid sequence or protein which has been removed from its naturally occurring environment, and includes recombinant or cloned DNA isolates and chemically synthesized analogs or analogs biologically synthesized by heterologous systems.

"KVLQT1 Allele" refers to normal alleles of the KVLQT1 locus as well as alleles of KVLQT1 carrying variations that cause LQT or JLN.

"KVLQT1 Locus", "KVLQT1 Gene", "KVLQT1 Nucleic Acids" or "KVLQT1 Polynucleotide" each refer to polynucleotides, all of which are in the KVLQT1 region that are likely to be expressed in normal tissue, certain alleles of which result in LQT or JLN. The KVLQT1 locus is intended to include coding sequences, intervening sequences and regulatory elements controlling transcription and/or translation. The KVLQT1 locus is intended to include all allelic variations of the DNA sequence.

These terms, when applied to a nucleic acid, refer to a nucleic acid which encodes a human KVLQT1 polypeptide, fragment, homolog or variant, including, e.g., protein fusions or deletions. The nucleic acids of the present invention will possess a sequence which is either derived from, or substantially similar to a natural KVLQT1-encoding gene or one having substantial homology with a natural KVLQT1-encoding gene or a portion thereof.

The KVLQT1 gene or nucleic acid includes normal alleles of the KVLQT1 gene, including silent alleles having no effect on the amino acid sequence of the KVLQT1 polypeptide as well as alleles leading to amino acid sequence variants of the KVLQT1 polypeptide that do not substantially affect its function. These terms also include alleles having one or more mutations which adversely affect the function of the KVLQT1 polypeptide. A mutation may be a change in the KVLQT1 nucleic acid sequence which produces a deleterious change in the amino acid sequence of the KVLQT1 polypeptide, resulting in partial or complete loss of KVLQT1 function, respectively, or may be a change in the nucleic acid sequence which results in the loss of effective KVLQT1 expression or the production of aberrant forms of the KVLQT1 polypeptide.

The KVLQT1 nucleic acid may be that shown in SEQ ID NO:1 (KVLQT1) or it may be an allele as described above or a variant or derivative differing from that shown by a change which is one or more of addition, insertion, deletion and substitution of one or more nucleotides of the sequence shown. Changes to the nucleotide sequence may result in an amino acid change at the protein level, or not, as determined by the genetic code.

Thus, nucleic acid according to the present invention may include a sequence different from the sequence shown in SEQ ID NO:1 yet encode a polypeptide with the same amino acid sequence as shown in SEQ ID NO:2. That is, nucleic acids of the present invention include sequences which are degenerate as a result of the genetic code. On the other hand, the encoded polypeptide may comprise an amino acid sequence which differs by one or more amino acid residues from the amino acid sequence shown in SEQ ID NO:2. Nucleic acid encoding a polypeptide which is an amino acid sequence variant, derivative or allele of the amino acid sequence shown in SEQ ID NO:2 is also provided by the present invention.

The KVLQT1 gene also refers to (a) any DNA sequence that (i) hybridizes to the complement of the DNA sequences that encode the amino acid sequence set forth in SEQ ID NO:2 under highly stringent conditions (Ausubel et al., 1992) and (ii) encodes a gene product functionally equivalent to KVLQT1, or (b) any DNA sequence that (i) hybridizes to the complement of the DNA sequences that encode the amino acid sequence set forth in SEQ ID NO:2 under less stringent conditions, such as moderately stringent conditions (Ausubel et al., 1992) and (ii) encodes a gene product functionally equivalent to KVLQT1. The invention also includes nucleic acid molecules that are the complements of the sequences described herein.

The polynucleotide compositions of this invention include RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

The present invention provides recombinant nucleic acids comprising all or part of the KVLQT1 region. The recombinant construct may be capable of replicating autonomously in a host cell. Alternatively, the recombinant construct may become integrated into the chromosomal DNA of the host cell. Such a recombinant polynucleotide comprises a polynucleotide of genomic, cDNA, semi-synthetic, or synthetic origin which, by virtue of its origin or manipulation, 1) is not associated with all or a portion of a polynucleotide with which it is associated in nature; 2) is linked to a polynucleotide other than that to which it is linked in nature; or 3) does not occur in nature. Where nucleic acid according to the invention includes RNA, reference to the sequence shown should be construed as reference to the RNA equivalent, with U substituted for T.

Therefore, recombinant nucleic acids comprising sequences otherwise not naturally occurring are provided by this invention. Although the wild-type sequence may be employed, it will often be altered, e.g., by deletion, substitution or insertion. cDNA or genomic libraries of various types may be screened as natural sources of the nucleic acids of the present invention, or such nucleic acids may be provided by amplification of sequences resident in genomic DNA or other natural sources, e.g., by PCR. The choice of cDNA libraries normally corresponds to a tissue source which is abundant in mRNA for the desired proteins. Phage libraries are normally preferred, but other types of libraries may be used. Clones of a library are spread onto plates, transferred to a substrate for screening, denatured and probed for the presence of desired sequences.

The DNA sequences used in this invention will usually comprise at least about five codons (15 nucleotides), more usually at least about 7–15 codons, and most preferably, at least about 35 codons. One or more introns may also be present. This number of nucleotides is usually about the minimal length required for a successful probe that would hybridize specifically with a KVLQT1-encoding sequence. In this context, oligomers of as low as 8 nucleotides, more generally 8–17 nucleotides, can be used for probes, especially in connection with chip technology.

Techniques for nucleic acid manipulation are described generally, for example, in Sambrook et al., 1989 or Ausubel et al., 1992. Reagents useful in applying such techniques, such as restriction enzymes and the like, are widely known in the art and commercially available from such vendors as New England BioLabs, Boehringer Mannheim, Amersham, Promega, U.S. Biochemicals, New England Nuclear, and a number of other sources. The recombinant nucleic acid sequences used to produce fusion proteins of the present invention may be derived from natural or synthetic sequences. Many natural gene sequences are obtainable from various cDNA or from genomic libraries using appropriate probes. See, GenBank, National Institutes of Health.

As used herein, a "portion" of the KVLQT1 locus or region or allele is defined as having a minimal size of at least about eight nucleotides, or preferably about 15 nucleotides, or more preferably at least about 25 nucleotides, and may have a minimal size of at least about 40 nucleotides. This definition includes all sizes in the range of 8–40 nucleotides as well as greater than 40 nucleotides. Thus, this definition includes nucleic acids of 8, 12, 15, 20, 25, 40, 60, 80, 100, 200, 300, 400, 500 nucleotides, or nucleic acids having any number of nucleotides within these ranges of values (e.g., 9, 10, 11, 16, 23, 30, 38, 50, 72, 121, etc., nucleotides), or nucleic acids having more than 500 nucleotides. The present invention includes all novel nucleic acids having at least 8 nucleotides derived from SEQ ID NO:1 or SEQ ID NO:5, its complement or functionally equivalent nucleic acid sequences. The present invention does not include nucleic acids which exist in the prior art. That is, the present invention includes all nucleic acids having at least 8 nucleotides derived from SEQ ID NO:1 or SEQ ID NO:5 with the proviso that it does not include nucleic acids existing in the prior art.

"KVLQT1 protein" or "KVLQT1 polypeptide" refers to a protein or polypeptide encoded by the KVLQT1 locus, variants or fragments thereof. The term "polypeptide" refers to a polymer of amino acids and its equivalent and does not refer to a specific length of the product; thus, peptides, oligopeptides and proteins are included within the definition of a polypeptide. This term also does not refer to, or exclude modifications of the polypeptide, for example, glycosylations, acetylations, phosphorylations, and the like. Included within the definition are, for example, polypeptides containing one or more analogs of an amino acid (including, for example, unnatural amino acids, etc.), polypeptides with substituted linkages as well as other modifications known in the art, both naturally and non-naturally occurring. Ordinarily, such polypeptides will be at least about 50% homologous to the native KVLQT1 sequence, preferably in excess of about 90%, and more preferably at least about 95% homologous. Also included are proteins encoded by DNA which hybridize under high or low stringency conditions, to KVLQT1-encoding nucleic acids and closely related polypeptides or proteins retrieved by antisera to the KVLQT1 protein.

The KVLQT1 polypeptide may be that shown in SEQ ID NO:2 which may be in isolated and/or purified form, free or substantially free of material with which it is naturally associated. The polypeptide may, if produced by expression in a prokaryotic cell or produced synthetically, lack native post-translational processing, such as glycosylation. Alternatively, the present invention is also directed to polypeptides which are sequence variants, alleles or derivatives of the KVLQT1 polypeptide. Such polypeptides may have an amino acid sequence which differs from that set forth in SEQ ID NO:2 by one or more of addition, substitution, deletion or insertion of one or more amino acids. Preferred such polypeptides have KVLQT1 function.

Substitutional variants typically contain the exchange of one amino acid for another at one or more sites within the protein, and may be designed to modulate one or more properties of the polypeptide, such as stability against proteolytic cleavage, without the loss of other functions or properties. Amino acid substitutions may be made on the basis of similarity in polarity, charge, solubility, hydrophobicity, hydrophilicity, and/or the amphipathic nature of the residues involved. Preferred substitutions are ones which are conservative, that is, one amino acid is replaced with one of similar shape and charge. Conservative substitutions are well known in the art and typically include substitutions within the following groups: glycine, alanine; valine, isoleucine, leucine; aspartic acid, glutamic acid; asparagine, glutamine; serine, threonine; lysine, arginine; and tyrosine, phenylalanine.

Certain amino acids may be substituted for other amino acids in a protein structure without appreciable loss of interactive binding capacity with structures such as, for example, antigen-binding regions of antibodies or binding sites on substrate molecules or binding sites on proteins interacting with the KVLQT1 polypeptide. Since it is the interactive capacity and nature of a protein which defines that protein's biological functional activity, certain amino acid substitutions can be made in a protein sequence, and its underlying DNA coding sequence, and nevertheless obtain a protein with like properties. In making such changes, the hydropathic index of amino acids may be considered. The importance of the hydrophobic amino acid index in conferring interactive biological function on a protein is generally understood in the art (Kyte and Doolittle, 1982). Alternatively, the substitution of like amino acids can be made effectively on the basis of hydrophilicity. The importance of hydrophilicity in conferring interactive biological function of a protein is generally understood in the art (U.S. Pat. No. 4,554,101). The use of the hydrophobic index or hydrophilicity in designing polypeptides is further discussed in U.S. Pat. No. 5,691,198.

The length of polypeptide sequences compared for homology will generally be at least about 16 amino acids, usually at least about 20 residues, more usually at least about 24 residues, typically at least about 28 residues, and preferably more than about 35 residues.

"Operably linked" refers to ajuxtaposition wherein the components so described are in a relationship permitting them to function in their intended manner. For instance, a promoter is operably linked to a coding sequence if the promoter affects its transcription or expression.

The term peptide mimetic or mimetic is intended to refer to a substance which has the essential biological activity of the KVLQT1 polypeptide. A peptide mimetic may be a peptide-containing molecule that mimics elements of protein secondary structure (Johnson et al., 1993). The underlying rationale behind the use of peptide mimetics is that the peptide backbone of proteins exists chiefly to orient amino acid side chains in such a way as to facilitate molecular interactions, such as those of antibody and antigen, enzyme and substrate or scaffolding proteins. A peptide mimetic is designed to permit molecular interactions similar to the natural molecule. A mimetic may not be a peptide at all, but it will retain the essential biological activity of natural KVLQT1 polypeptide.

"Probes". Polynucleotide polymorphisms associated with KVLQT1 alleles which predispose to LQT or JLN are detected by hybridization with a polynucleotide probe which forms a stable hybrid with that of the target sequence, under stringent to moderately stringent hybridization and wash conditions. If it is expected that the probes will be perfectly complementary to the target sequence, high stringency conditions will be used. Hybridization stringency may be lessened if some mismatching is expected, for example, if variants are expected with the result that the probe will not be completely complementary. Conditions are chosen which rule out nonspecific/adventitious bindings, that is, which minimize noise. (It should be noted that throughout this disclosure, if it is simply stated that "stringent" conditions are used that is meant to be read as "high stringency" conditions are used.) Since such indications identify neutral DNA polymorphisms as well as mutations, these indications need further analysis to demonstrate detection of a KVLQT1 susceptibility allele.

Probes for KVLQT1 alleles may be derived from the sequences of the KVLQT1 region, its cDNA, functionally equivalent sequences, or the complements thereof. The probes may be of any suitable length, which span all or a portion of the KVLQT1 region, and which allow specific hybridization to the region. If the target sequence contains a sequence identical to that of the probe, the probes may be short, e.g., in the range of about 8–30 base pairs, since the hybrid will be relatively stable under even stringent conditions. If some degree of mismatch is expected with the probe, i.e., if it is suspected that the probe will hybridize to a variant region, a longer probe may be employed which hybridizes to the target sequence with the requisite specificity.

The probes will include an isolated polynucleotide attached to a label or reporter molecule and may be used to isolate other polynucleotide sequences, having sequence similarity by standard methods. For techniques for preparing and labeling probes see, e.g., Sambrook et al., 1989 or Ausubel et al., 1992. Other similar polynucleotides may be selected by using homologous polynucleotides. Alternatively, polynucleotides encoding these or similar polypeptides may be synthesized or selected by use of the redundancy in the genetic code. Various codon substitutions may be introduced, e.g., by silent changes (thereby producing various restriction sites) or to optimize expression for a particular system. Mutations may be introduced to modify the properties of the polypeptide, perhaps to change the polypeptide degradation or turnover rate.

Probes comprising synthetic oligonucleotides or other polynucleotides of the present invention may be derived from naturally occurring or recombinant single- or double-stranded polynucleotides, or be chemically synthesized. Probes may also be labeled by nick translation, Klenow fill-in reaction, or other methods known in the art.

Portions of the polynucleotide sequence having at least about eight nucleotides, usually at least about 15 nucleotides, and fewer than about 9 kb, usually fewer than about 1.0 kb, from a polynucleotide sequence encoding KVLQT1 are preferred as probes. This definition therefore includes probes of sizes 8 nucleotides through 9000 nucleotides. Thus, this definition includes probes of 8, 12, 15, 20, 25, 40, 60, 80, 100, 200, 300, 400 or 500 nucleotides or probes having any number of nucleotides within these ranges of values (e.g., 9, 10, 11, 16, 23, 30, 38, 50, 72, 121, etc., nucleotides), or probes having more than 500 nucleotides. The probes may also be used to determine whether mRNA encoding KVLQT1 is present in a cell or tissue. The present invention includes all novel probes having at least 8 nucleotides derived from SEQ ID NO:1 or SEQ ID NO:5, its complement or functionally equivalent nucleic acid sequences. The present invention does not include probes which exist in the prior art. That is, the present invention includes all probes having at least 8 nucleotides derived from SEQ ID NO:1 or SEQ ID NO:5 with the proviso that they do not include probes existing in the prior art.

Similar considerations and nucleotide lengths are also applicable to primers which may be used for the amplification of all or part of the KVLQT1 gene. Thus, a definition for primers includes primers of 8, 12, 15, 20, 25, 40, 60, 80, 100, 200, 300, 400, 500 nucleotides, or primers having any number of nucleotides within these ranges of values (e.g., 9, 10, 11, 16, 23, 30, 38, 50, 72, 121, etc. nucleotides), or primers having more than 500 nucleotides, or any number of nucleotides between 500 and 9000. The primers may also be used to determine whether mRNA encoding KVLQT1 is present in a cell or tissue. The present invention includes all novel primers having at least 8 nucleotides derived from the KVLQT1 locus for amplifying the KVLQT1 gene, its complement or functionally equivalent nucleic acid sequences. The present invention does not include primers which exist in the prior art. That is, the present invention includes all primers having at least 8 nucleotides with the proviso that it does not include primers existing in the prior art.

"Protein modifications or fragments" are provided by the present invention for KVLQT1 polypeptides or fragments thereof which are substantially homologous to primary structural sequence but which include, e.g., in vivo or in vitro chemical and biochemical modifications or which incorporate unusual amino acids. Such modifications include, for example, acetylation, carboxylation, phosphorylation, glycosylation, ubiquitination, labeling, e.g., with radionuclides, and various enzymatic modifications, as will be readily appreciated by those well skilled in the art. A variety of methods for labeling polypeptides and of substituents or labels useful for such purposes are well known in the art, and include radioactive isotopes such as $^{32}P$, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods of labeling polypeptides are well known in the art. See Sambrook et al., 1989 or Ausubel et al., 1992.

Besides substantially full-length polypeptides, the present invention provides for biologically active fragments of the polypeptides. Significant biological activities include ligand-binding, immunological activity and other biological activities characteristic of KVLQT1 polypeptides. Immunological activities include both immunogenic function in a target immune system, as well as sharing of immunological epitopes for binding, serving as either a competitor or substitute antigen for an epitope of the KVLQT1 protein. As used herein, "epitope" refers to an antigenic determinant of a polypeptide. An epitope could comprise three amino acids in a spatial conformation which is unique to the epitope. Generally, an epitope consists of at least five such amino acids, and more usually consists of at least 8–10 such amino acids. Methods of determining the spatial conformation of such amino acids are known in the art.

For immunological purposes, tandem-repeat polypeptide segments may be used as immunogens, thereby producing highly antigenic proteins. Alternatively, such polypeptides will serve as highly efficient competitors for specific binding. Production of antibodies specific for KVLQT1 polypeptides or fragments thereof is described below.

The present invention also provides for fusion polypeptides, comprising KVLQT1 polypeptides and fragments. Homologous polypeptides may be fusions between two or more KVLQT1 polypeptide sequences or between the sequences of KVLQT1 and a related protein. Likewise, heterologous fusions may be constructed which would exhibit a combination of properties or activities of the derivative proteins. For example, ligand-binding or other domains may be "swapped" between different new fusion polypeptides or fragments. Such homologous or heterologous fusion polypeptides may display, for example, altered strength or specificity of binding. Fusion partners include immunoglobulins, bacterial β-galactosidase, trpE, protein A, β-lactamase, alpha amylase, alcohol dehydrogenase and yeast alpha mating factor. See Godowski et al., 1988.

Fusion proteins will typically be made by either recombinant nucleic acid methods, as described below, or may be chemically synthesized. Techniques for the synthesis of polypeptides are described, for example, in Merrifield (1963).

"Protein purification" refers to various methods for the isolation of the KVLQT1 polypeptides from other biological material, such as from cells transformed with recombinant nucleic acids encoding KVLQT1, and are well known in the art. For example, such polypeptides may be purified by immunoaffinity chromatography employing, e.g., the antibodies provided by the present invention. Various methods of protein purification are well known in the art, and include those described in Deutscher, 1990 and Scopes, 1982.

The terms "isolated", "substantially pure", and "substantially homogeneous" are used interchangeably to describe a protein or polypeptide which has been separated from components which accompany it in its natural state. A monomeric protein is substantially pure when at least about 60 to 75% of a sample exhibits a single polypeptide sequence. A substantially pure protein will typically comprise about 60 to 90% W/W of a protein sample, more usually about 95%, and preferably will be over about 99% pure. Protein purity or homogeneity may be indicated by a number of means well known in the art, such as polyacrylamide gel electrophoresis of a protein sample, followed by visualizing a single polypeptide band upon staining the gel. For certain purposes, higher resolution may be provided by using HPLC or other means well known in the art which are utilized for purification.

A KVLQT1 protein is substantially free of naturally associated components when it is separated from the native contaminants which accompany it in its natural state. Thus, a polypeptide which is chemically synthesized or synthesized in a cellular system different from the cell from which it naturally originates will be substantially free from its naturally associated components. A protein may also be rendered substantially free of naturally associated components by isolation, using protein purification techniques well known in the art.

A polypeptide produced as an expression product of an isolated and manipulated genetic sequence is an "isolated polypeptide", as used herein, even if expressed in a homologous cell type. Synthetically made forms or molecules expressed by heterologous cells are inherently isolated molecules.

"Recombinant nucleic acid" is a nucleic acid which is not naturally occurring, or which is made by the artificial combination of two otherwise separated segments of sequence. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions.

"Regulatory sequences" refers to those sequences normally within 100 kb of the coding region of a locus, but they may also be more distant from the coding region, which affect the expression of the gene (including transcription of the gene, and translation, splicing, stability or the like of the messenger RNA).

"Substantial homology or similarity". A nucleic acid or fragment thereof is "substantially homologous" ("or substantially similar") to another if, when optimally aligned (with appropriate nucleotide insertions or deletions) with the other nucleic acid (or its complementary strand), there is nucleotide sequence identity in at least about 60% of the nucleotide bases, usually at least about 70%, more usually at least about 80%, preferably at least about 90%, and more preferably at least about 95–98% of the nucleotide bases.

To determine homology between two different nucleic acids, the percent homology is to be determined using the BLASTN program "BLAST 2 sequences". This program is available for public use from the National Center for Biotechnology Information (NCBI) over the Internet (http://www.ncbi.nlm.nih.gov/gorf/bl2.html) (Altschul et al., 1997). The parameters to be used are whatever combination of the following yields the highest calculated percent homology (as calculated below) with the default parameters shown in parentheses:

Program—blastn
Matrix—0 BLOSUM62
Reward for a match—0 or 1 (1)
Penalty for a mismatch—0, −1, −2 or −3 (−2)
Open gap penalty—0, 1, 2, 3, 4 or 5 (5)
Extension gap penalty—0 or 1 (1)
Gap x_dropoff—0 or 50 (50)
Expect—10

Along with a variety of other results, this program shows a percent identity across the complete strands or across regions of the two nucleic acids being matched. The program shows as part of the results an alignment and identity of the two strands being compared. If the strands are of equal length then the identity will be calculated across the complete length of the nucleic acids. If the strands are of unequal lengths, then the length of the shorter nucleic acid is to be used. If the nucleic acids are quite similar across a portion of their sequences but different across the rest of their sequences, the blastn program "BLAST 2 Sequences" will show an identity across only the similar portions, and these portions are reported individually. For purposes of determining homology herein, the percent homology refers to the shorter of the two sequences being compared. If any one region is shown in different alignments with differing percent identities, the alignments which yield the greatest homology are to be used. The averaging is to be performed as in this example of SEQ ID NOs:3 and 4.

5'-ACCGTAGCTACGTACGTATATAGAAAGGGCG CGATCGTCGTCGCGTATGACGACTTAGCATGC-3' (SEQ ID NO:3)

5'-ACCGGTAGCTACGTACGTTATTTAGAAAGGGG TGTGTGTGTGTGTGTAAACCGGGGTTTTCGGG ATCGTCCGTCGCGTATGACGACTTAGCCATGCA CGGTATATCGTATTAGGACTTAGCGATTGACT AG-3' (SEQ ID NO:4)

The program "BLAST 2 Sequences" shows differing alignments of these two nucleic acids depending upon the parameters which are selected. As examples, four sets of parameters were selected for comparing SEQ ID NOs:3 and 4 (gap x_dropoff was 50 for all cases), with the results shown in Table 1. It is to be noted that none of the sets of parameters selected as shown in Table 1 is necessarily the best set of parameters for comparing these sequences. The percent homology is calculated by multiplying for each region showing identity the fraction of bases of the shorter strand within a region times the percent identity for that region and adding all of these together. For example, using the first set of parameters shown in Table 1, SEQ ID NO:3 is the short sequence (63 bases), and two regions of identity are shown, the first encompassing bases 4–29 (26 bases) of SEQ ID NO:3 with 92% identity to SEQ ID NO:4 and the second encompassing bases 39–59 (21 bases) of SEQ ID NO:3 with 100% identity to SEQ ID NO:4. Bases 1–3, 30–38 and 60–63 (16 bases) are not shown as having any identity with SEQ ID NO:4. Percent homology is calculated as: (26/63)(92)+(21/63)(100)+(16/63)(0)=71.3% homology. The percents of homology calculated using each of the four sets of parameters shown are listed in Table 1. Several other combinations of parameters are possible, but they are not listed for the sake of brevity. It is seen that each set of parameters resulted in a different calculated percent homology. Because the result yielding the highest percent homology is to be used, based solely on these four sets of parameters one would state that SEQ ID NOs:3 and 4 have 87.1% homology. Again it is to be noted that use of other parameters may show an even higher homology for SEQ ID NOs:3 and 4, but for brevity not all the possible results are shown.

Alternatively, substantial homology or (similarity) exists when a nucleic acid or fragment thereof will hybridize to another nucleic acid (or a complementary strand thereof) under selective hybridization conditions, to a strand, or to its complement. Selectivity of hybridization exists when hybridization which is substantially more selective than total lack of specificity occurs. Typically, selective hybridization will occur when there is at least about 55% homology over a stretch of at least about 14 nucleotides, preferably at least about 65%, more preferably at least about 75%, and most preferably at least about 90%. See, Kanehisa, 1984. The length of homology comparison, as described, may be over longer stretches, and in certain embodiments will often be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides.

TABLE 1

| | Parameter Values | | | | | |
|---|---|---|---|---|---|---|
| Match | Mismatch | Open Gap | Extension Gap | Regions of identity (%) | | Homology |
| 1 | −2 | 5 | 1 | 4–29 of 3 and 5–31 of 4 (92%) | 39–59 of 3 and 71–91 of 4 (100%) | 71.3 |
| 1 | −2 | 2 | 1 | 4–29 of 3 and 5–31 of 4 (92%) | 33–63 of 3 and 64–96 of 4 (93%) | 83.7 |
| 1 | −1 | 5 | 1 | — | 30–59 of 3 and 61–91 of 4 (93%) | 44.3 |
| 1 | −1 | 2 | 1 | 4–29 of 3 and 5–31 of 4 (92%) | 30–63 of 3 and 61–96 of 4 (91%) | 87.1 |

Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30° C., typically in excess of 37° C., and preferably in excess of 45° C. Stringent salt conditions will ordinarily be less than 1000 mM, typically less than 500 mM, and preferably less than 200 mM. However, the combination of parameters is much more important than the measure of any single parameter. The stringency conditions are dependent on the length of the nucleic acid and the base composition of the nucleic acid and can be determined by techniques well known in the art. See, e.g., Wetmur and Davidson, 1968.

Probe sequences may also hybridize specifically to duplex DNA under certain conditions to form triplex or other higher order DNA complexes. IThe preparation of such probes and suitable hybridization conditions are well known in the art.

The terms "substantial homology" or "substantial identity", when referring to polypeptides, indicate that the polypeptide or protein in question exhibits at least about 30% identity with an entire naturally-occurring protein or a portion thereof, usually at least about 70% identity, more usually at least about 80% identity, preferably at least about 90% identity, and more preferably at least about 95% identity.

Homology, for polypeptides, is typically measured using sequence analysis software. See, e.g., the Sequence Analysis Software Package of the Genetics Computer Group, University of Wisconsin Biotechnology Center, 910 University Avenue, Madison, Wis. 53705. Protein analysis software matches similar sequences using measures of homology assigned to various substitutions, deletions and other modifications. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine.

"Substantially similar function" refers to the function of a modified nucleic acid or a modified protein, with reference to the wild-type KVLQT1 nucleic acid or wild-type KVLQT1 polypeptide. The modified polypeptide will be substantially homologous to the wild-type KVLQT1 polypeptide and will have substantially the same function. The modified polypeptide may have an altered amino acid sequence and/or may contain modified amino acids. In addition to the similarity of function, the modified polypeptide may have other useful properties, such as a longer half-life. The similarity of function (activity) of the modified polypeptide may be substantially the same as the activity of the wild-type KVLQT1 polypeptide. Alternatively, the similarity of function (activity) of the modified polypeptide may be higher than the activity of the wild-type KVLQT1 polypeptide. The modified polypeptide is synthesized using conventional techniques, or is encoded by a modified nucleic acid and produced using conventional techniques. The modified nucleic acid is prepared by conventional techniques. A nucleic acid with a function substantially similar to the wild-type KVLQT1 gene function produces the modified protein described above.

A polypeptide "fragment", "portion" or "segment" is a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids.

The polypeptides of the present invention, if soluble, may be coupled to a solid-phase support, e.g., nitrocellulose, nylon, column packing materials (e.g., Sepharose beads), magnetic beads, glass wool, plastic, metal, polymer gels, cells, or other substrates. Such supports may take the form, for example, of beads, wells, dipsticks, or membranes.

"Target region" refers to a region of the nucleic acid which is amplified and/or detected. The term "target sequence" refers to a sequence with which a probe or primer will form a stable hybrid under desired conditions.

The practice of the present invention employs, unless otherwise indicated, conventional techniques of chemistry, molecular biology, microbiology, recombinant DNA, genetics, and immunology. See, e.g., Maniatis et al., 1982; Sambrook et al., 1989; Ausubel et al., 1992; Glover, 1985; Anand, 1992; Guthrie and Fink, 1991. A general discussion of techniques and materials for human gene mapping, including mapping of human chromosome 1, is provided, e.g., in White and Lalouel, 1988.

Preparation of Recombinant or Chemically Synthesized Nucleic Acids: Vectors, Transformation, Host Cells Large amounts of the polynucleotides of the present invention may be produced by replication in a suitable host cell. Natural or synthetic polynucleotide fragments coding for a desired fragment will be incorporated into recombinant polynucleotide constructs, usually DNA constructs, capable of introduction into and replication in a prokaryotic or eukaryotic cell. Usually the polynucleotide constructs will be suitable for replication in a unicellular host, such as yeast or bacteria, but may also be intended for introduction to (with and without integration within the genome) cultured mammalian or plant or other eukaryotic cell lines. The purification of nucleic acids produced by the methods of the present invention are described, e.g., in Sambrook et al., 1989 or Ausubel et al., 1992.

The polynucleotides of the present invention may also be produced by chemical synthesis, e.g., by the phosphoramidite method described by Beaucage and Caruthers (1981) or the triester method according to Matteucci and Caruthers (1981) and may be performed on commercial, automated oligonucleotide synthesizers. A double-stranded fragment may be obtained from the single-stranded product of chemical synthesis either by synthesizing the complementary strand and annealing the strand together under appropriate conditions or by adding the complementary strand using DNA polymerase with an appropriate primer sequence.

Polynucleotide constructs prepared for introduction into a prokaryotic or eukaryotic host may comprise a replication system recognized by the host, including the intended polynucleotide fragment encoding the desired polypeptide, and will preferably also include transcription and translational initiation regulatory sequences operably linked to the polypeptide encoding segment. Expression vectors may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Such vectors may be prepared by means of standard recombinant techniques well known in the art and discussed, for example, in Sambrook et al. (1989) or Ausubel et al. (1992).

An appropriate promoter and other necessary vector sequences will be selected so as to be functional in the host, and may include, when appropriate, those naturally associated with the KVLQT1 gene. Examples of workable combinations of cell lines and expression vectors are described in Sambrook et al. (1989) or Ausubel et al. (1992); see also, e.g., Metzger et al. (1988). Many useful vectors are known in the art and may be obtained from such vendors as Stratagene, New England Biolabs, Promega Biotech, and others. Promoters such as the trp, lac and phage promoters, tRNA promoters and glycolytic enzyme promoters may be used in prokaryotic hosts. Useful yeast promoters include promoter regions for metallothionein, 3-phosphoglycerate kinase or other glycolytic enzymes such as enolase or glyceraldehyde-3-phosphate dehydrogenase, enzymes responsible for maltose and galactose utilization, and others. Vectors and promoters suitable for use in yeast expression are further described in Hitzeman et al., EP 73,675A. Appropriate non-native mammalian promoters might include the early and late promoters from SV40 (Fiers et al., 1978) or promoters derived from murine Molony leukemia virus, mouse tumor virus, avian sarcoma viruses, adenovirus II, bovine papilloma virus or polyoma. Insect promoters may be derived from baculovirus. In addition, the construct may be joined to an amplifiable gene (e.g., DHFR) so that multiple copies of the gene may be made. For appropriate enhancer and other expression control sequences, see also *Enhancers and Eukaryotic Gene Expression*, Cold Spring Harbor Press, Cold Spring Harbor, N.Y. (1983). See also, e.g., U.S. Pat. Nos. 5,691,198; 5,735,500; 5,747,469 and 5,436,146.

While such expression vectors may replicate autonomously, they may also replicate by being inserted into the genome of the host cell, by methods well known in the art.

Expression and cloning vectors will likely contain a selectable marker, a gene encoding a protein necessary for survival or growth of a host cell transformed with the vector. The presence of this gene ensures growth of only those host cells which express the inserts. Typical selection genes encode proteins that a) confer resistance to antibiotics or other toxic substances, e.g. ampicillin, neomycin, methotrexate, etc., b) complement auxotrophic deficiencies, or c) supply critical nutrients not available from complex media, e.g., the gene encoding D-alanine racemase for Bacilli. The choice of the proper selectable marker will depend on the host cell, and appropriate markers for different hosts are well known in the art.

The vectors containing the nucleic acids of interest can be transcribed in vitro, and the resulting RNA introduced into the host cell by well-known methods, e.g., by injection (see, Kubo et al. (1988)), or the vectors can be introduced directly into host cells by methods well known in the art, which vary depending on the type of cellular host, including electroporation; transfection employing calcium chloride, rubidium chloride calcium phosphate, DEAE-dextran, or other substances; microprojectile bombardment; lipofection; infection (where the vector is an infectious agent, such as a retroviral genome); and other methods. See generally, Sambrook et al. (1989) and Ausubel et al. (1992). The introduction of the polynucleotides into the host cell by any method known in the art, including, inter alia, those described above, will be referred to herein as "transformation." The cells into which have been introduced nucleic acids described above are meant to also include the progeny of such cells.

Large quantities of the nucleic acids and polypeptides of the present invention may be prepared by expressing the KVLQT1 nucleic acid or portions thereof in vectors or other expression vehicles in compatible prokaryotic or eukaryotic host cells. The most commonly used prokaryotic hosts are strains of *Escherichia coli*, although other prokaryotes, such as *Bacillus subtilis* or Pseiidomonas may also be used.

Mammalian or other eukaryotic host cells, such as those of yeast, filamentous fungi, plant, insect, or amphibian or avian species, may also be useful for production of the proteins of the present invention. Propagation of mammalian cells in culture is per se well known. See, Jakoby and Pastan (eds.) (1979). Examples of commonly used mammalian host cell lines are VERO and HeLa cells, Chinese hamster ovary (CHO) cells, and W138, BHK, and COS cell lines, although it will be appreciated by the skilled practitioner that other cell lines may be appropriate, e.g., to provide higher expression, desirable glycosylation patterns, or other features. An example of a commonly used insect cell line is SF9.

Clones are selected by using markers depending on the mode of the vector construction. The marker may be on the same or a different DNA molecule, preferably the same DNA molecule. In prokaryotic hosts, the transformant may be selected, e.g., by resistance to ampicillin, tetracycline or other antibiotics. Production of a particular product based on temperature sensitivity may also serve as an appropriate marker.

Prokaryotic or eukaryotic cells transformed with the polynucleotides of the present invention will be useful not only for the production of the nucleic acids and polypeptides of the present invention, but also, for example, in studying the characteristics of KVLQT1 polypeptides.

The probes and primers based on the KVLQT1 gene sequence disclosed herein are used to identify homologous KVLQT1 gene sequences and proteins in other species. These gene sequences and proteins are used in the diagnostic/prognostic, therapeutic and drug screening methods described herein for the species from which they have been isolated.

Methods of Use: Drug Screening

The invention is particularly useful for screening compounds by using KVLQT1 proteins in transformed cells, transfected oocytes or transgenic animals. Since mutations in either the KVLQT1 or KCNE1 protein can alter the functioning of the cardiac $I_{Ks}$ potassium channel, candidate drugs are screened for effects on the channel using cells containing either a normal KVLQT1 or KCNE1 protein and a mutant KCNE1 or KVLQT1 protein, respectively, or a mutant KVLQT1 and a mutant KCNE1 protein. The drug is added to the cells in culture or administered to a transgenic animal and the effect on the induced current of the $I_{Ks}$ potassium channel is compared to the induced current of a cell or animal containing the wild-type KVLQT1 and minK. Drug candidates which alter the induced current to a more normal level are useful for treating or preventing LQT.

This invention is particularly useful for screening compounds by using the KVLQT1 polypeptide or binding fragment thereof in any of a variety of drug screening techniques.

The KVLQT1 polypeptide or fragment employed in such a test may either be free in solution, affixed to a solid support, or borne on a cell surface. One method of drug screening utilizes eucaryotic or procaryotic host cells which are stably transformed with recombinant polynucleotides expressing the polypeptide or fragment, preferably in competitive binding assays. Such cells, either in viable or fixed form, can be used for standard binding assays. One may measure, for example, for the formation of complexes between a KVLQT1 polypeptide or fragment and the agent being tested, or examine the degree to which the formation of a complex between a KVLQT1 polypeptide or fragment and a known ligand is interfered with by the agent being tested.

Thus, the present invention provides methods of screening for drugs comprising contacting such an agent with a KVLQT1 polypeptide or fragment thereof and assaying (i) for the presence of a complex between the agent and the KVLQT1 polypeptide or fragment, or (ii) for the presence of a complex between the KVLQT1 polypeptide or fragment and a ligand, by methods well known in the art. In such competitive binding assays the KVLQTL polypeptide or fragment is typically labeled. Free KVLQT1 polypeptide or fragment is separated from that present in a protein:protein complex, and the amount of free (i.e., uncomplexed) label is a measure of the binding of the agent being tested to KVLQT1 or its interference with KVLQT1:ligand binding. One may also measure the amount of bound, rather than free, KVLQT1. It is also possible to label the ligand rather than the KVLQT1 and to measure the amount of ligand binding to KVLQT1 in the presence and in the absence of the drug being tested.

Another technique for drug screening provides high throughput screening for compounds having suitable binding affinity to the KVLQT1 polypeptides and is described in detail in Geysen (published PCT application WO 84/03564). Briefly stated, large numbers of different small peptide test compounds are synthesized on a solid substrate, such as plastic pins or some other surface. The peptide test compounds are reacted with KVLQT1 polypeptide and washed.

Bound KVLQT1 polypeptide is then detected by methods well known in the art.

Purified KVLQT1 can be coated directly onto plates for use in the aforementioned drug screening techniques. However, non-neutralizing antibodies to the polypeptide can be used to capture antibodies to immobilize the KVLQT1 polypeptide on the solid phase.

This invention also contemplates the use of competitive drug screening assays in which neutralizing antibodies capable of specifically binding the KVLQT1 polypeptide compete with a test compound for binding to the KVLQT1 polypeptide or fragments thereof. In this manner, the antibodies can be used to detect the presence of any peptide which shares one or more antigenic determinants of the KVLQT1 polypeptide.

The above screening methods are not limited to assays employing only KVLQT1 but are also applicable to studying KVLQT1-protein complexes. The effect of drugs on the activity of this complex is analyzed.

In accordance with these methods, the following assays are examples of assays which can be used for screening for drug candidates.

A mutant KVLQT1 (per se or as part of a fusion protein) is mixed with a wild-type protein (per se or as part of a fusion protein) to which wild-type KVLQT1 binds. This mixing is performed in both the presence of a drug and the absence of the drug, and the amount of binding of the mutant KVLQT1 with the wild-type protein is measured. If the amount of the binding is more in the presence of said drug than in the absence of said drug, the drug is a drug candidate for treating JLN resulting from a mutation in KVLQT1.

A wild-type KVLQT1 (per se or as part of a fusion protein) is mixed with a wild-type protein (per se or as part of a fusion protein) to which wild-type KVLQT1 binds. This mixing is performed in both the presence of a drug and the absence of the drug, and the amount of binding of the wild-type KVLQT1 with the wild-type protein is measured. If the amount of the binding is more in the presence of said drug than in the absence of said drug, the drug is a drug candidate for treating LQT resulting from a mutation in KVLQT1.

A mutant protein, which as a wild-type protein binds to KVLQT1 (per se or as part of a fusion protein) is mixed with a wild-type KVLQT1 (per se or as part of a fusion protein). This mixing is performed in both the presence of a drug and the absence of the drug, and the amount of binding of the mutant protein with the wild-type KVLQT1 is measured. If the amount of the binding is more in the presence of said drug than in the absence of said drug, the drug is a drug candidate for treating JLN resulting from a mutation in the gene encoding the protein.

The polypeptide of the invention may also be used for screening compounds developed as a result of combinatorial library technology. Combinatorial library technology provides an efficient way of testing a potential vast number of different substances for ability to modulate activity of a polypeptide. Such libraries and their use are known in the art. The use of peptide libraries is preferred. See, for example, WO 97/02048.

Briefly, a method of screening for a substance which modulates activity of a polypeptide may include contacting one or more test substances with the polypeptide in a suitable reaction medium, testing the activity of the treated polypeptide and comparing that activity with the activity of the polypeptide in comparable reaction medium untreated with the test substance or substances. A difference in activity between the treated and untreated polypeptides is indicative of a modulating effect of the relevant test substance or substances.

Prior to or as well as being screened for modulation of activity, test substances may be screened for ability to interact with the polypeptide, e.g., in a yeast two-hybrid system (e.g., Bartel et al., 1993; Fields and Song, 1989; Chevray and Nathans, 1992; Lee et al., 1995). This system may be used as a coarse screen prior to testing a substance for actual ability to modulate activity of the polypeptide. Alternatively, the screen could be used to screen test substances for binding to a KVLQT1 specific binding partner, or to find mimetics of the KVLQT1 polypeptide.

Following identification of a substance which modulates or affects polypeptide activity, the substance may be investigated further. Furthermore, it may be manufactured and/or used in preparation, i.e., manufacture or formulation, or a composition such as a medicament, pharmaceutical composition or drug. These may be administered to individuals.

Thus, the present invention extends in various aspects not only to a substance identified using a nucleic acid molecule as a modulator of polypeptide activity, in accordance with what is disclosed herein, but also a pharmaceutical composition, medicament, drug or other composition comprising such a substance, a method comprising administration of such a composition comprising such a substance, a method comprising administration of such a composition to a patient, e.g., for treatment (which may include preventative treatment) of LQT, use of such a substance in the manufacture of a composition for administration, e.g., for treatment of LQT, and a method of making a pharmaceutical composition comprising admixing such a substance with a pharmaceutically acceptable excipient, vehicle or carrier, and optionally other ingredients.

A substance identified as a modulator of polypeptide function may be peptide or non-peptide in nature. Non-peptide "small molecules" are often preferred for many in vivo pharmaceutical uses. Accordingly, a mimetic or mimic of the substance (particularly if a peptide) may be designed for pharmaceutical use.

The designing of mimetics to a known pharmaceutically active compound is a known approach to the development of pharmaceuticals based on a "lead" compound. This might be desirable where the active compound is difficult or expensive to synthesize or where it is unsuitable for a particular method of administration, e.g., pure peptides are unsuitable active agents for oral compositions as they tend to be quickly degraded by proteases in the alimentary canal. Mimetic design, synthesis and testing is generally used to avoid randomly screening large numbers of molecules for a target property.

There are several steps commonly taken in the design of a mimetic from a compound having a given target property. First, the particular parts of the compound that are critical and/or important in determining the target property are determined. In the case of a peptide, this can be done by systematically varying the amino acid residues in the peptide, e.g., by substituting each residue in turn. Alanine scans of peptide are commonly used to refine such peptide motifs. These parts or residues constituting the active region of the compound are known as its "pharmacophore".

Once the pharmacophore has been found, its structure is modeled according to its physical properties, e.g. stereochemistry, bonding, size and/or charge, using data from a range of sources, e.g., spectroscopic techniques, x-ray diffraction data and NMR. Computational analysis, similarity mapping (which models the charge and/or volume of a pharmacophore, rather than the bonding between atoms) and other techniques can be used in this modeling process.

In a variant of this approach, the three-dimensional structure of the ligand and its binding partner are modeled. This can be especially useful where the ligand and/or binding partner change conformation on binding, allowing the model to take account of this in the design of the mimetic.

A template molecule is then selected onto which chemical groups which mimic the pharmacophore can be grafted. The template molecule and the chemical groups grafted onto it can conveniently be selected so that the mimetic is easy to synthesize, is likely to be pharmacologically acceptable, and does not degrade in vivo, while retaining the biological activity of the lead compound. Alternatively, where the mimetic is peptide-based, further stability can be achieved by cyclizing the peptide, increasing its rigidity. The mimetic or mimetics found by this approach can then be screened to see whether they have the target property, or to what extent they exhibit it. Further optimization or modification can then be carried out to arrive at one or more final mimetics for in vivo or clinical testing.

Methods of Use: Nucleic Acid Diagnosis and Diagnostic Kits

In order to detect the presence of a KVLQT1 allele predisposing an individual to LQT, a biological sample such as blood is prepared and analyzed for the presence or absence of susceptibility alleles of KVLQT1. In order to detect the presence of JLN or as a prognostic indicator, a biological sample is prepared and analyzed for the presence or absence of mutant alleles of KVLQT1. Results of these tests and interpretive information are returned to the health care provider for communication to the tested individual. Such diagnoses may be performed by diagnostic laboratories, or, alternatively, diagnostic kits are manufactured and sold to health care providers or to private individuals for self-diagnosis.

Initially, the screening method involves amplification of the relevant KVLQT1 sequences. In another preferred embodiment of the invention, the screening method involves a non-PCR based strategy. Such screening methods include two-step label amplification methodologies that are well known in the art. Both PCR and non-PCR based screening strategies can detect target sequences with a high level of sensitivity.

The most popular method used today is target amplification. Here, the target nucleic acid sequence is amplified with polymerases. One particularly preferred method using polymerase-driven amplification is the polymerase chain reaction (PCR). The polymerase chain reaction and other polymerase-driven amplification assays can achieve over a million-fold increase in copy number through the use of polymerase-driven amplification cycles. Once amplified, the resulting nucleic acid can be sequenced or used as a substrate for DNA probes.

When the probes are used to detect the presence of the target sequences the biological sample to be analyzed, such as blood or serum, may be treated, if desired, to extract the nucleic acids. The sample nucleic acid may be prepared in various ways to facilitate detection of the target sequence, e.g. denaturation, restriction digestion, electrophoresis or dot blotting. The targeted region ofthe analyte nucleic acid usually must be at least partially single-stranded to form hybrids with the targeting sequence of the probe. If the sequence is naturally single-stranded, denaturation will not be required. However, if the sequence is double-stranded, the sequence will probably need to be denatured. Denaturation can be carried out by various techniques known in the art.

Analyte nucleic acid and probe are incubated under conditions which promote stable hybrid formation of the target sequence in the probe with the putative targeted sequence in the analyte. The region of the probes which is used to bind to the analyte can be made completely complementary to the targeted region of human chromosome 11 for KVLQT1. Therefore, high stringency conditions are desirable in order to prevent false positives. However, conditions of high stringency are used only if the probes are complementary to regions of the chromosome which are unique in the genome. The stringency of hybridization is determined by a number of factors during hybridization and during the washing procedure, including temperature, ionic strength, base composition, probe length, and concentration of formamide. These factors are outlined in, for example, Maniatis et al., 1982 and Sambrook et al., 1989. Under certain circumstances, the formation of higher order hybrids, such as triplexes, quadraplexes, etc., may be desired to provide the means of detecting target sequences.

Detection, if any, of the resulting hybrid is usually accomplished by the use of labeled probes. Alternatively, the probe may be unlabeled, but may be detectable by specific binding with a ligand which is labeled, either directly or indirectly. Suitable labels, and methods for labeling probes and ligands are known in the art, and include, for example, radioactive labels which may be incorporated by known methods (e.g., nick translation, random priming or kinasing), biotin, fluorescent groups, chemiluminescent groups (e.g., dioxetanes, particularly triggered dioxetanes), enzymes, antibodies, gold nanoparticles and the like. Variations of this basic scheme are known in the art, and include those variations that facilitate separation of the hybrids to be detected from extraneous materials and/or that amplify the signal from the labeled moiety. A number of these variations are reviewed in, e.g., Matthews and Kricka, 1988; Landegren et al., 1988; Mifflin, 1989; U.S. Pat. No. 4,868,105; and in EPO Publication No. 225,807.

As noted above, non-PCR based screening assays are also contemplated in this invention. This procedure hybridizes a nucleic acid probe (or an analog such as a methyl phosphonate backbone replacing the normal phosphodiester), to the low level DNA target. This probe may have an enzyme covalently linked to the probe, such that the covalent linkage does not interfere with the specificity of the hybridization. This enzyme-probe-conjugate-target nucleic acid complex can then be isolated away from the free probe enzyme conjugate and a substrate is added for enzyme detection. Enzymatic activity is observed as a change in color development or luminescent output resulting in a $10^3$–$10^6$ increase in sensitivity. For an example relating to the preparation of oligodeoxynucleotide-alkaline phosphatase conjugates and their use as hybridization probes, see Jablonski et al. (1986).

Two-step label amplification methodologies are known in the art. These assays work on the principle that a small ligand (such as digoxigenin, biotin, or the like) is attached to a nucleic acid probe capable of specifically binding KVLQT1. Allele specific probes are also contemplated within the scope of this example and exemplary allele specific probes include probes encompassing the predisposing mutations of this patent application.

In one example, the small ligand attached to the nucleic acid probe is specifically recognized by an antibody-enzyme conjugate. In one embodiment of this example, digoxigenin is attached to the nucleic acid probe. Hybridization is detected by an antibody-alkaline phosphatase conjugate which turns over a chemiluminescent substrate. For methods for labeling nucleic acid probes according to this embodiment see Martin et al., 1990. In a second example, the small ligand is recognized by a second ligand-enzyme conjugate that is capable of specifically complexing to the first ligand. A well known embodiment of this example is the biotin-avidin type of interactions. For methods for labeling nucleic acid probes and their use in biotin-avidin based assays see Rigby et al., 1977 and Nguyen et al., 1992.

It is also contemplated within the scope of this invention that the nucleic acid probe assays of this invention will employ a cocktail of nucleic acid probes capable of detecting KVLQT1. Thus, in one example to detect the presence of KVLQT1 in a cell sample, more than one probe complementary to the gene is employed and in particular the number of different probes is alternatively two, three, or five different nucleic acid probe sequences. In another example, to detect the presence of mutations in the KVLQT1 gene sequence in a patient, more than one probe complementary to these genes is employed where the cocktail includes probes capable of binding to the allele-specific mutations identified in populations of patients with alterations in KVLQT1. In this embodiment, any number of probes can be used, and will preferably include probes corresponding to the major gene mutations identified as predisposing an individual to LQT.

Methods of Use: Peptide Diagnosis and Diagnostic Kits

The presence of JLN can also be detected on the basis of the alteration of wild-type KVLQT1 polypeptide. Such alterations can be determined by sequence analysis in accordance with conventional techniques. More preferably, antibodies (polyclonal or monoclonal) are used to detect differences in, or the absence of KVLQT1 peptides. Techniques for raising and purifying antibodies are well known in the art and any such techniques may be chosen to achieve the preparations claimed in this invention. In a preferred embodiment of the invention, antibodies will immunoprecipitate KVLQT1 proteins from solution as well as react with these proteins on Western or immunoblots of polyacrylamide gels. In another preferred embodiment, antibodies will detect KVLQT1 proteins in paraffin or frozen tissue sections, using immunocytochemical techniques.

Preferred embodiments relating to methods for detecting KVLQT1 or its mutations include enzyme linked immunosorbent assays (ELISA), radioimmunoassays (RIA), immunoradiometric assays (IRMA) and immunoenzymatic assays (IEMA), including sandwich assays using monoclonal and/or polyclonal antibodies. Exemplary sandwich assays are described by David et al., in U.S. Pat. Nos. 4,376,110 and 4,486,530, hereby incorporated by reference.

Methods of Use: Rational Drug Design

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. See, e.g., Hodgson, 1991. In one approach, one first determines the three-dimensional structure of a protein of interest (e.g., KVLQT1 polypeptide) by x-ray crystallography, by computer modeling or most typically, by a combination of approaches. Less often, useful information regarding the structure of a polypeptide may be gained by modeling based on the structure of homologous proteins. An example of rational drug design is the development of HIV protease inhibitors (Erickson et al., 1990). In addition, peptides (e.g., KVLQT1 polypeptide) are analyzed by an alanine scan (Wells, 1991). In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced banks of peptides. Selected peptides would then act as the pharmacore.

Thus, one may design drugs which have, e.g., improved KVLQT1 polypeptide activity or stability or which act as inhibitors, agonists, antagonists, etc. of KVLQT1 polypeptide activity. By virtue of the availability of cloned KVLQT1 sequences, sufficient amounts of the KVLQT1 polypeptide may be made available to perform such analytical studies as x-ray crystallography. In addition, the knowledge of the KVLQT1 protein sequences provided herein will guide those employing computer modeling techniques in place of, or in addition to x-ray crystallography.

Methods of Use: Gene Therapy

According to the present invention, a method is also provided of supplying wild-type KVLQT1 function to a cell which carries a mutant KVLQT1 allele, respectively. Supplying such a function should allow normal functioning of the recipient cells. The wild-type gene or a part of the gene may be introduced into the cell in a vector such that the gene remains extrachromosomal. In such a situation, the gene will be expressed by the cell from the extrachromosomal location. More preferred is the situation where the wild-type gene or a part thereof is introduced into the mutant cell in such a way that it recombines with the endogenous mutant gene present in the cell. Such recombination requires a double recombination event which results in the correction of the gene mutation. Vectors for introduction of genes both for recombination and for extrachromosomal maintenance are known in the art, and any suitable vector may be used. Methods for introducing DNA into cells such as electroporation, calcium phosphate coprecipitation and viral transduction are known in the art, and the choice of method is within the competence of the practitioner.

As generally discussed above, the KVLQT1 gene or fragment, where applicable, may be employed in gene therapy methods in order to increase the amount of the expression products of such gene in cells. It may also be useful to increase the level of expression of a given LQT gene even in those heart cells in which the mutant gene is expressed at a "normal" level, but the gene product is not fully functional.

Gene therapy would be carried out according to generally accepted methods, for example, as described by Friedman (1991) or Culver (1996). Cells from a patient would be first analyzed by the diagnostic methods described above, to ascertain the production of KVLQT1 polypeptide in the cells. A virus or plasmid vector (see further details below), containing a copy of the KVLQT1 gene linked to expression control elements and capable of replicating inside the cells, is prepared. The vector may be capable of replicating inside the cells. Alternatively, the vector may be replication deficient and is replicated in helper cells for use in gene therapy. Suitable vectors are known, such as disclosed in U.S. Pat. No. 5,252,479 and PCT published application WO 93/07282 and U.S. Pat. Nos. 5,691,198; 5,747,469; 5,436,146 and 5,753,500. The vector is then injected into the patient. If the transfected gene is not permanently incorporated into the genome of each of the targeted cells, the treatment may have to be repeated periodically.

Gene transfer systems known in the art may be useful in the practice of the gene therapy methods of the present invention. These include viral and nonviral transfer methods. A number of viruses have been used as gene transfer vectors or as the basis for repairing gene transfer vectors, including papovaviruses (e.g., SV40, Madzak et al., 1992), adenovirus (Berkner, 1992; Berkner et al., 1988; Gorziglia and Kapikian, 1992; Quantin et al., 1992; Rosenfeld et al., 1992; Wilkinson and Akrigg, 1992; Stratford-Perricaudet et al., 1990; Schneider et al., 1998), vaccinia virus (Moss, 1992; Moss, 1996), adeno-associated virus (Muzyczka, 1992; Ohi et al., 1990; Russell and Hirata, 1998), herpesviruses including HSV and EBV (Margolskee, 1992; Jolnson et al., 1992; Fink et al., 1992; Breakefield and Geller, 1987; Freese et al., 1990; Fink et al., 1996), lentiviruses (Naldini et al., 1996), Sindbis and Semliki Forest virus (Berglund et al., 1993), and retroviruses of avian (Bandyopadhyay and Temin, 1984; Petropoulos et al., 1992), murine (Miller, 1992; Miller et al., 1985; Sorge et al., 1984; Mann and Baltimore, 1985; Miller et al., 1988), and human origin (Shimada et al., 1991; Helseth et al., 1990; Page et al., 1990; Buchschacher and Panganiban, 1992). Most human gene therapy protocols have been based on disabled murine retroviruses, although adenovirus and adeno-associated virus are also being used.

Nonviral gene transfer methods known in the art include chemical techniques such as calcium phosphate coprecipitation (Graham and van der Eb, 1973; Pellicer et al., 1980); mechanical techniques, for example microinjection (Anderson et al., 1980; Gordon et al., 1980; Brinster et al., 1981; Costantini and Lacy, 1981); membrane fusion-mediated transfer via liposomes (Felgner et al., 1987; Wang and Iluang, 1989; Kaneda et al., 1989; Stewart et al., 1992; Nabel et al., 1990; Lim et al., 1991); and direct DNA uptake and receptor-mediated DNA transfer (Wolff et al., 1990; Wu et al., 1991; Zenke et al., 1990; Wu et al., 1989; Wolff et al., 1991; Wagner et al., 1990; Wagner et al., 1991; Cotten et al., 1990; Curiel et al., 1992; Curiel et al., 1991). Viral-mediated gene transfer can be combined with direct in vivo gene transfer using liposome delivery, allowing one to direct the viral vectors to the tumor cells and not into the surrounding nondividing cells. Alternatively, the retroviral vector producer cell line can be injected into tumors (Culver et al., 1992). Injection of producer cells would then provide a continuous source of vector particles. This technique has been approved for use in humans with inoperable brain tumors.

In an approach which combines biological and physical gene transfer methods, plasmid DNA of any size is combined with a polylysine-conjugated antibody specific to the adenovirus hexon protein, and the resulting complex is bound to an adenovirus vector. The trimolecular complex is then used to infect cells. The adenovirus vector permits efficient binding, internalization, and degradation of the endosome before the coupled DNA is damaged. For other techniques for the delivery of adenovirus based vectors see Schneider et al. (1998) and U.S. Pat. Nos. 5,691,198; 5,747,469; 5,436,146 and 5,753,500.

Liposome/DNA complexes have been shown to be capable of mediating direct in vivo gene transfer. While in standard liposome preparations the gene transfer process is nonspecific, localized in vivo uptake and expression have been reported in tumor deposits, for example, following direct in situ administration (Nabel, 1992).

Expression vectors in the context of gene therapy are meant to include those constructs containing sequences sufficient to express a polynucleotide that has been cloned therein. In viral expression vectors, the construct contains viral sequences sufficient to support packaging of the construct. If the polynucleotide encodes KVLQT1, expression will produce KVLQT1. If the polynucleotide encodes an antisense polynucleotide or a ribozyme, expression will produce the antisense polynucleotide or ribozyme. Thus in this context, expression does not require that a protein product be synthesized. In addition to the polynucleotide cloned into the expression vector, the vector also contains a promoter functional in eukaryotic cells. The cloned polynucleotide sequence is under control of this promoter. Suitable eukaryotic promoters include those described above. The expression vector may also include sequences, such as selectable markers and other sequences described herein.

Gene transfer techniques which target DNA directly to heart tissue is preferred. Receptor-mediated gene transfer, for example, is accomplished by the conjugation of DNA (usually in the form of covalently closed supercoiled plasmid) to a protein ligand via polylysine. Ligands are chosen on the basis of the presence of the corresponding ligand receptors on the cell surface of the target cell/tissue type. These ligand-DNA conjugates can be injected directly into the blood if desired and are directed to the target tissue where receptor binding and internalization of the DNA-protein complex occurs. To overcome the problem of intracellular destruction of DNA, coinfection with adenovirus can be included to disrupt endosome function.

The therapy is as follows: patients who carry a KVLQT1 susceptibility allele are treated with a gene delivery vehicle such that some or all of their heart precursor cells receive at least one additional copy of a functional normnal KVLQT1 individuals have reduced risk of JLN to the extent that the effect of the susceptible allele has been countered by the presence of the normal allele.

Methods of Use: Peptide Therapy

Peptides which have KVLQT1 activity can be supplied to cells which carry a mutant or missing KVLQT1 allele. Protein can be produced by expression of the cDNA sequence in bacteria, for example, using known expression vectors. Alternatively, KVLQT1 polypeptide can be extracted from KVLQT1-producing mammalian cells. In addition, the techniques of synthetic chemistry can be employed to synthesize KVLQT1 protein. Any of such techniques can provide the preparation of the present invention which comprises the KVLQT1 protein. The preparation is substantially free of other human proteins. This is most readily accomplished by synthesis in a microorganism or in vitro.

Active KVLQT1 molecules can be introduced into cells by microinjection or by use of liposomes, for example. Alternatively, some active molecules may be taken up by cells, actively or by diffusion. Supply of molecules with KVLQT1 activity should lead to partial reversal of JLN. Other molecules with KVLQT1 activity (for example, peptides, drugs or organic compounds) may also be used to effect such a reversal. Modified polypeptides having substantially similar function are also used for peptide therapy.

Methods of Use: Transformed Hosts

Animals for testing therapeutic agents can be selected after mutagenesis of whole animals or after treatment of germline cells or zygotes. Such treatments include insertion of mutant KVLQT1 alleles, usually from a second animal species, as well as insertion of disrupted homologous genes. Alternatively, the endogenous KVLQT1 gene of the animals may be disrupted by insertion or deletion mutation or other genetic alterations using conventional techniques (Capecchi, 1989; Valancius and Smithies, 1991; Hasty et al., 1991; Shinkai et al., 1992; Mombaerts et al., 1992; Philpott et al., 1992; Snouwaert et al., 1992; Donehower et al., 1992). After test substances have been administered to the animals, the presence of JLN must be assessed. If the test substance prevents or suppresses the appearance of JLN, then the test substance is a candidate therapeutic agent for treatment of JLN. These animal models provide an extremely important testing vehicle for potential therapeutic products.

KVLQT1 is a putative cardiac potassium channel gene and causes the chromosome 11-linked form of LQT. As shown here, it also is a cause of JLN. Genetic analyses suggested that KVLQT1 encodes a voltage-gated potassium channel with functional importance in cardiac repolarization and it has been shown that KVLQT1 coassembles with minK (also called KCNE1) to form a cardiac $I_{Ks}$ potassium channel. The mechanism of chromosome 11-linked LQT and JLN probably involves reduced repolarizing KVLQT1 current. Since potassium channels with six transmembrane domains are thought to be formed from homo- or hetero-tetramers (MacKinnon, 1991; MacKinnon et al., 1993; Covarrubias et al., 1991), it is possible that LQT-associated mutations of KVLQT1 act through a dominant-negative mechanism. The type and location of KVLQT 1 mutations described here are consistent with this hypothesis. The resultant suppression of potassium channel function, in turn, would likely lead to abnormal cardiac repolarization and increased risk of ventricular tachyarrhythmias. The mutations identified in HERG, and the biophysics of potassium channel alpha subunits, suggest that chromosome 7-linked LQT results from dominant-negative mutations and a resultant reduction in functional channels. In chromosome 3-linked LQT, by contrast, the LQT-associated deletions identified in SCN5A are likely to result in functional cardiac sodium channels with altered properties, such as delayed inactivation or altered voltage-dependence of channel inactivation. Delayed sodium channel inactivation would increase inward sodium current, depolarizing the membrane. This effect is similar to the altered membrane potential expected from HERG mutations where outward potassium current is decreased. It is unlikely that more deleterious mutations of SCN5A would cause LQT. A reduction of the total number of cardiac sodium channels, for example, would be expected to reduce action potential duration, a phenotype opposite that of LQT.

Presymptomatic diagnosis of LQT has depended on identification of QT prolongation on electrocardiograms. Unfortunately, electrocardiograms are rarely performed in young, healthy individuals. In addition, many LQT gene carriers have relatively normal QT intervals, and the first sign of disease can be a fatal cardiac arrhythmia (Vincent et al., 1992). Now that several genes have been identified which are associated with LQT, genetic testing for this disorder can be contemplated. This will require continued mutational analyses and identification of additional LQT genes. With more detailed phenotypic analyses, phenotypic differences between the varied forms of LQT may be discovered. These differences may be useful for diagnosis and treatment. With the present finding that a homozygous variant of KVLQT1 is a cause of JLN it is also now possible to perform genetic testing for JLN and to use this information for diagnosis and treatment.

The identification of the association between the KVLQT1 gene mutation and JLN permits the early presymptomatic screening of individuals to identify those at risk for developing JLN. To identify such individuals, the KVLQT1 alleles are screened for mutations either directly or after cloning the alleles. The alleles are tested for the presence of nucleic acid sequence differences from the normal allele using any suitable technique, including but not limited to, one of the following methods: fluorescent in situ hybridization (FISH), direct DNA sequencing, PFGE analysis, Southern blot analysis, single stranded conformation analysis (SSCP), linkage analysis, RNase protection assay, allele specific oligonucleotide (ASO), dot blot analysis and PCR-SSCP analysis. Also useful is the recently developed technique of DNA microchip technology. For example, either (1) the nucieotide sequence of both the cloned alleles and normal KVLQT1 gene or appropriate fragment (coding sequence or genomic sequence) are determined and then compared, or (2) the RNA transcripts of the KVLQT1 gene or gene fragment are hybridized to single stranded whole genomic DNA from an individual to be tested, and the resulting heteroduplex is treated with Ribonuclease A (RNase A) and run on a denaturing gel to detect the location of any mismatches. Two of these methods can be carried out according to the following procedures.

The alleles of the KVLQT1 gene in an individual to be tested are cloned using conventional techniques. For example, a blood sample is obtained from the individual. The genomic DNA isolated from the cells in this sample is partially digested to an average fragment size of approximately 20 kb. Fragments in the range from 18–21 kb are isolated. The resulting fragments are ligated into an appropriate vector. The sequences of the clones are then determined and compared to the normal KVLQT1 gene.

Alternatively, polymerase chain reactions (PCRs) are performed with primer pairs for the 5' region or the exons of the KVLQT1 gene. PCRs can also be perfonned with primer pairs based on any sequence of the normal KVLQT1 gene. For example, primer pairs for one of the introns can be prepared and utilized. Finally, RT-PCR can also be performed on the mRNA. The amplified products are then analyzed by single stranded conformation polymorphisms (SSCP) using conventional techniques to identify any differences and these are then sequenced and compared to the normal gene sequence.

Individuals can be quickly screened for common KVLQT1 gene variants by amplifying the individual's DNA using suitable primer pairs and analyzing the amplified product, e.g., by dot-blot hybridization using allele-specific oligonucleotide probes.

The second method employs RNase A to assist in the detection of differences between the normal KVLQT1 gene and defective genes. This comparison is performed in steps using small (~500 bp) restriction fragments of the KVLQT1 gene as the probe. First, the KVLQT1 gene is digested with a restriction enzyme(s) that cuts the gene sequence into fragments of approximately 500 bp. These fragments are separated on an electrophoresis gel, purified from the gel and cloned individually, in both orientations, into an SP6 vector (e.g., pSP64 or pSP65). The SP6-based plasmids containing inserts of the KVLQT1 gene fragments are transcribed in vitro using the SP6 transcription system, well known in the art, in the presence of $[\alpha^{32}P]GTP$, generating radiolabeled RNA transcripts of both strands of the gene.

Individually, these RNA transcripts are used to form heteroduplexes with the allelic DNA using conventional techniques. Mismatches that occur in the RNA:DNA heteroduplex, owing to sequence differences between the KVLQT1 fragment and the KVLQT1 allele subclone from the individual, result in cleavage in the RNA strand when treated with RNase A. Such mismatches can be the result of point mutations or small deletions in the individual's allele. Cleavage of the RNA strand yields two or more small RNA fragments, which run faster on the denaturing gel than the RNA probe itself.

Any differences which are found, will identify an individual as having a molecular variant of the KVLQT1 gene and the consequent presence of long QT syndrome. These variants can take a number of forms. The most severe forms would be frame shift mutations or large deletions which would cause the gene to code for an abnormal protein or one which would significantly alter protein expression. Less severe disruptive mutations would include small in-frame deletions and nonconservative base pair substitutions which would have a significant effect on the protein produced, such as changes to or from a cysteine residue, from a basic to an acidic amino acid or vice versa, from a hydrophobic to hydrophilic amino acid or vice versa, or other mutations which would affect secondary or tertiary protein structure. Silent mutations or those resulting in conservative amino acid substitutions would not generally be expected to disrupt protein function.

Genetic testing will enable practitioners to identify individuals at risk for LQT or JLN at, or even before, birth. Presymptomatic diagnosis of LQT or JLN will enable prevention of these disorders. Existing medical therapies, including beta adrenergic blocking agents, may prevent and delay the onset of problems associated with the disease. Finally, this invention changes our understanding of the cause and treatment of common heart disease like cardiac arrhythmias which account for 11% of all natural deaths. Existing diagnosis has focused on measuring the QT interval from electrocardiograms. This method is not a fully accurate indicator of the presence of long QT syndrome or of JLN. The present invention is a more accurate indicator of the presence of these conditions. Genetic testing and improved mechanistic understanding of LQT and JLN provide the opportunity for prevention of life-threatening arrhythmias through rational therapies. It is possible, for example, that potassium channel opening agents will reduce the risk of arrhythmias in patients with KVLQT1 mutations; sodium chatiel blocking agents, by contrast, may be a more effective treatment for patients with mutations that alter the function of SCN5A. Finally, these studies may provide insight into mechanisms underlying common arrhythmias, as these arrhythmias are often associated with abnormal cardiac repolarization and may result from a combination of inherited and acquired factors.

Pharmaceutical Compositions and Routes of Administration

The KVLQT1 polypeptides, antibodies, peptides and nucleic acids of the present invention can be formulated in pharmaceutical compositions, which are prepared according to conventional pharmaceutical compounding techniques. See, for example, Remington's Pharmaceutical Sciences, 18th Ed. (1990, Mack Publishing Co., Easton, Pa.). The composition may contain the active agent or pharmaceutically acceptable salts of the active agent. These compositions may comprise, in addition to one of the active substances, a pharmaceutically acceptable excipient, carrier, buffer, stabilizer or other materials well known in the art. Such materials should be non-toxic and should not interfere with the efficacy of the active ingredient. The carrier may take a wide variety of forms depending on the form of preparation desired for administration, e.g., intravenous, oral, intrathecal, epineural or parenteral.

For oral administration, the compounds can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent can be encapsulated to make it stable to passage through the gastrointestinal tract while at the same time allowing for passage across the blood brain barrier. See for example, WO 96/11698.

For parenteral administration, the compound may be dissolved in a pharmaceutical carrier and administered as either a solution or a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like. When the compounds are being administered intrathecally, they may also be dissolved in cerebrospinal fluid.

The active agent is preferably administered in a therapeutically effective amount. The actual amount administered, and the rate and time-course of administration, will depend on the nature and severity of the condition being treated. Prescription of treatment, e.g. decisions on dosage, timing, etc., is within the responsibility of general practitioners or specialists, and typically takes account of the disorder to be treated, the condition of the individual patient, the site of delivery, the method of administration and other factors known to practitioners. Examples of techniques and protocols can be found in Remington's Pharmaceutical Sciences.

Alternatively, targeting therapies may be used to deliver the active agent more specifically to certain types of cell, by the use of targeting systems such as antibodies or cell specific ligands. Targeting may be desirable for a variety of reasons, e.g. if the agent is unacceptably toxic, or if it would otherwise require too high a dosage, or if it would not otherwise be able to enter the target cells.

Instead of administering these agents directly, they could be produced in the target cell, e.g. in a viral vector such as described above or in a cell based delivery system such as described in U.S. Pat. No. 5,550,050 and published PCT application Nos. WO 92/19195, WO 94/25503, WO 95/01203, WO 95/05452, WO 96/02286, WO 96/02646, WO 96/40871, WO 96/40959 and WO 97/12635, designed for implantation in a patient. The vector could be targeted to the specific cells to be treated, or it could contain regulatory elements which are more tissue specific to the target cells. The cell based delivery system is designed to be implanted in a patient's body at the desired target site and contains a coding sequence for the active agent. Alternatively, the agent could be administered in a precursor form for conversion to the active form by an activating agent produced in, or targeted to, the cells to be treated. See for example, EP 425,731A and WO 90/07936.

The present invention is further detailed in the following Examples, which are offered by way of illustration and are not intended to limit the invention in any manner. Standard techniques well known in the art or the techniques specifically described below are utilized.

EXAMPLE 1

Ascertainment and Phenotyping of Kindred 2948

A large JLN family was identified by physician referral. A team of researchers attended a large family gathering organized by the patient's paternal aunt and grandmother. Pedigree information, patient history, electrocardiograms and blood samples were collected at the gathering. Individuals in this family ranged in age from 13 months to 82 years. Individuals were phenotypically characterized based on the QT interval corrected for heart rate and the presence of syncope, seizures, and aborted sudden death as described (Keating et al., 1991a; Jiang et al., 1994; Vincent et al., 1992). The phenotypic criteria were: unaffected, QTc≦0.41 with no symptoms; uncertain, 0.41<QTc<0.47 with no symptoms, and QTc<0.45 with symptoms; affected, QTc≧0.45 with symptoms, or asymptomatic with QTc≧0.47. The criteria for phenotypic assignment were not age dependent. Informed consent was obtained from all individuals or their guardians in accordance with local institutional review board guidelines. Phenotypic data were interpreted without knowledge of genotype.

The family which was studied was of Scottish descent and had a child with JLN. This female infant was born to a consanguineous marriage of second cousins (individual V-5, FIG. 1). At 35 weeks gestation the obstetrician informed the 25 year old mother that the fetus' heart rate had dropped to 70–80 beats per minute. An ultrasound showed that growth and development were normal. At 38 weeks the heart rate continued to be slow. A second ultrasound confirmed normal development. The infant was born without complications by normal vaginal delivery. The slow heart rate persisted after birth. One hour post delivery the infant turned cyanotic and hypotonic with the first bottle feeding, was rushed to the pediatric ICU and monitored for 14 days. Electrolytes and hematologic evaluation were normal. Blood cultures, urinalysis, urine cultures and chest X-ray were negative. Electrocardiogram showed sinus bradycardia with a rate of 82 beats per minute, and QT interval prolongation with QTc of 0.61 seconds. On the third day, LQT was diagnosed and propanolol treatment initiated. On the eighth day, audiograms indicated bilateral sensory deafness. Neurologic evaluation was otherwise unremarkable, and no evidence of brain stem dysfunction was found. There was no evidence of dysmorphology. On day 10, the infant was sent home with an apnea monitor. Deafness was confirmed at age 4 weeks; serial audiograms indicated bilateral sensory deafness. There was no evidence of infection, meningitis or temporal bone fractures and no history of treatment with ototoxic drugs. At 26 months the proband continues on propanolol with no syncope, seizures or tachyarrhythmia observed to date.

No further evaluation was performed on family members. Seven months after delivery, the proband's mother suffered a cardiac arrest when her alarm clock sounded. At the time she was exhausted and extremely anxious.

After the mother died, the family was referred to our laboratory for genetic evaluation. Phenotypic analyses revealed that 14 family members had prolonged QTc intervals ranging from 0.47 to 0.53 seconds (FIG. 1). Thirty-two family members had borderline QTc intervals ranging from 0.42 to 0.46 seconds. Six family members gave a history of syncope. Three had experienced one syncopal episode: patient II-13 (QTc of 0.46 seconds, unknown precipitation); patient III-29 (QTc of 0.49 seconds, while smoking marijuana); and patient IV-4 (QTc of 0.51 seconds, while exercising). Three other patients had multiple syncopal episodes: patient III-27 (QTc of 0.53 seconds, while exercising); patient III-33 (QTc of 0.46 seconds, unknown precipitation); and patient IV-14 (QTc of 0.41 seconds, while exercising or at rest). None of these individuals complained of hearing deficit. Formal audiometric analyses of individuals IV-4, V-1, and V-3 showed normal hearing.

By inspection, it is apparent that the long-QT syndrome phenotype is inherited as an autosomal dominant trait in kindred 2948 (FIG. 1). This pattern of inheritance is characterized by vertical transmission of the disease phenotype, the presence of the phenotype in each generation and the involvement of both sexes. Father to son transmission is observed in this family, excluding X-linked inheritance.

EXAMPLE 2

Genotyping and Linkage Analysis

Linkage analysis is a technique that can be used to determine if a gene responsible for a phenotype and a genetic marker are located on the same chromosomal segment. In this technique, an investigator examines a family to determine if a phenotype is coinherited with a specific DNA sequence variant (allele) of known chromosomal location. Genes or segments of DNA that have two or more forms are known as polymorphic markers and can be detected using the polymerase chain reaction (PCR) (Keating, 1992).

In this study, linkage analysis was used to determine if the long-QT syndrome phenotype was coinherited with the polymorphic markers TH and D11S1318 located near KVLQT1 (Q. Wang et al., 1996). Small synthetic DNA primers (oligonucleotides) were used in PCR to amplify DNA from each individual. PCR genotyping was performed as described with the following modifications (Jiang et al., 1994). Reactions were completed with 75 ng DNA in a final volume of 10 $\mu$L using a Perkin-Elmer Cetus 9600 thermocycler. Amplification conditions were 94° C. for 3 minutes followed by 30 cycles of 94° C. for 10 seconds, 58° C. for 20 seconds, 72° C. for 20 seconds and a 5 minute final extension at 72° C. Ten microliters of 95% formamide loading dye was added to each reaction, samples were denatured at 94° C. for 5 minutes and placed on ice. Three microliters of each sample was separated on a 6% denaturing polyacrylamide gel. Gels were dried on 3 MM filter paper and exposed for 12 hours at −70° C. The pattern of alleles (genotype) for each individual, which appears as bands of variable size on the film, was determined by inspection.

Genotypes were scored without knowledge of phenotypic data. The LINKAGE Version 5.1 software package was used for pairwise (MLINK) linkage analysis (Lathrop et al., 1985). Penetrance was set to 95% and the LQT syndrome gene frequency (0.001) was assumed to be equal between males and females. Allele frequencies were set to 1/n where n equals the number of alleles for each marker in this family (TH, n=5; KVLQT1, n=2; D11S1318, n=10).

Genotypic analyses were performed with markers at the known autosomal dominant LQT loci. TH and D11S1318, polymorphic markers tightly linked to KVLQT1, were completely linked to the LQT phenotype in this family (Q. Wang et al., 1996). The LOD (logarithm of odds) scores for linkage were 4.70 and 5.46 at recombination fraction of 0.00 for TH and D11S1318, respectively (p<0.001 for both markers;

Table 2). These data indicate that KVLQT1 is an excellent candidate gene for LQT in this family.

EXAMPLE 3

Mutational Analysis

Genomic samples were amplified by PCR and used in single strand conformational polymorphism (SSCP) analysis as described (Curran et al., 1995) to screen for mutations in KVLQT1. In this technique a small, approximately 200 bp, section of a patient's genomic DNA is amplified by PCR. If that patient has a mutation, PCR will amplify both normal and mutant

TABLE 2

Pairwise LOD* Scores between LQT Phenotype in Kindred 2948 and Chromosome 11p15.5 Markers, Including the KVLQT1 Mutation#

| Marker | Recombination Fraction (θ) | | | | | | $Z_{max}^a$ | $\theta_{max}^b$ |
|---|---|---|---|---|---|---|---|---|
| | 0.00 | 0.001 | 0.01 | 0.05 | 0.1 | 0.2 | | |
| TH | 4.70 | 4.70 | 4.63 | 4.31 | 3.89 | 2.98 | 4.70 | 0.00 |
| KVLQT1 | 5.08 | 5.07 | 4.98 | 4.60 | 4.09 | 3.03 | 5.08 | 0.00 |
| D11S1318 | 5.46 | 5.45 | 5.37 | 4.99 | 4.50 | 3.44 | 5.46 | 0.00 |

*LOD scores were computed with the assumption of 95% penetrance, disease allele frequency of 0.001, and equal female and male recombination frequencies. When penetrance was varied from 60% to 100%, the maximum LOD scores ranged from 4.09–4.81 for TH, 4.77–5.57 for D11S1318 and 4.38–5.19 for the KVLQT1 mutation.
Chromosome 11p15.5 markers were completely linked to the disease phenotype in kindred 2948.
$^a Z_{max}$ indicates maximum LOD score
$^b \theta_{max}$ indicates estimated recombination fraction at $Z_{max}$ alleles. The two different products can then be distinguished by separation on nondenaturing gels. The principle underlying SSCP is that a single strand of DNA will migrate through a nondenaturing gel at a rate that depends on the size and the specific sequence of the strand (Orita et al., 1989). Another strand of identical size, containing a single nucleotide substitution will travel through the same gel at a slightly different rate. This difference in mobility results from an altered conformation of the DNA molecule with the nucleotide substitution and produces an abnormal SSCP band.

PCR was completed with 75 ng DNA in a volume of 10 μL using a Perkin-Elmer Cetus 9600 thermocycler. Amplification conditions were 94° C. for 3 minutes followed by 5 cycles of 94° C. for 10 seconds, 64° C. for 20 seconds, 72° C. for 20 seconds and 30 cycles of 94° C. for 10 seconds, 60° C. for 20 seconds and 72° C. for 20 seconds and a 5 minute final extension at 72° C. Reactions were diluted with 40 μL of 0.1% SDS/10 mM EDTA and with 30 μL of 95% formamide loading dye. The mixture was denatured at 94° C. for 5 minutes and placed on ice. Three microliters of each sample was separated on 5% and 10% non-denaturing polyacrylamide gels (acrylamide:bisacrylamide 49:1) at 4° C. and on 0.5x and 1x MDE (mutation detection enhancement gels (FMC BioProducts) at room temperature. Electrophoreses on the 5% and 10% gels were completed at 40 W for 3–5 hours; electrophoreses on 0.5x and 1x MDE gels were completed overnight at 350V and 600V, respectively. Gels were dried on 3 MM filter paper and exposed for 18 hours at −70° C.

Figures 2A, 2B:
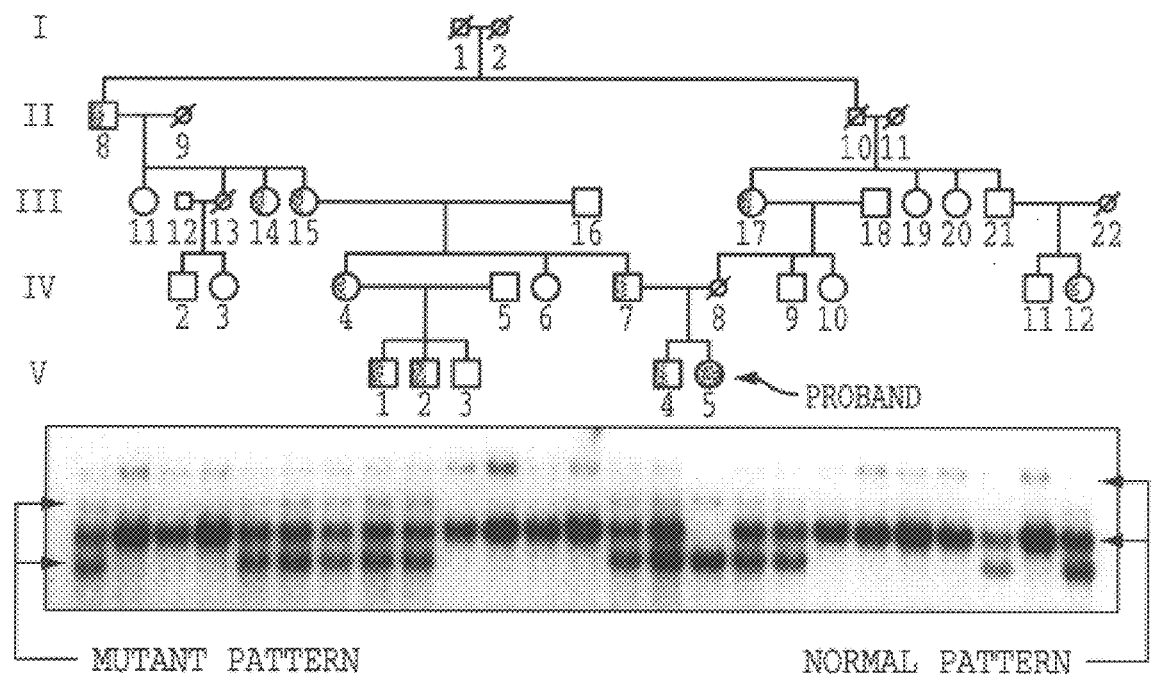
FIGS. 2A–B. Cosegregation of the abnormal SSCP with the LQT phenotype in JLN kindred 2948 and DNA sequence of the KVLQT1 mutation.

SSCP analyses were used to screen for functional mutations in KVLQT1. An abnormal conformer was observed in affected members of the family, but not in unaffected individuals (FIGS. 2A–B). The proband with JLN (individual V-5) had two copies of the aberrant SSCP conformer. Linkage analyses indicated that the SSCP anomaly was completely linked to the LQT phenotype in this family with a LOD score of 5.08 at recombination fraction of 0.00 (Table 2).

This indicates odds greater than 100,000 to 1 favoring linkage and corresponds to p<0.001. The abnormal SSCP conformer was not observed in DNA samples obtained from 200 unrelated control individuals (400 chromosomes).

EXAMPLE 4

DNA Sequence Analyses

SSCP bands were cut out of the gel and eluted in 100 μL double distilled water at 65° C. for 30 minutes. Ten microliters of eluted DNA was used as template in a second PCR reaction using the original primer pair. Products were separated on 1% low melting temperature agarose gels (FMC BioProducts), phenol-chloroform extracted and ethanol precipitated. DNA was sequenced in both directions by the dideoxy chain termination method on an Applied Biosystems model 373A DNA sequencer.

DNA sequence analysis revealed that the abnormal conformer contained a single nucleotide (G) insertion after nucleotide 729 of SEQ ID NO:1 (base 567 of the coding sequence numbering from the A nucleotide of the ATG initiation codon). The wild-type KVLQT1 sequence is shown as SEQ ID NO:1 and the wild-type KVLQT1 sequence is shown as SEQ ID NO:2. The mutated KVLQT1 sequence with the inserted G is shown as SEQ ID NO:5 and the mutated KVLQT1 is shown as SEQ ID NO:6. This insertion causes a frameshift, disrupting the coding sequence after the second putative membrane spanning domain of KVLQT1 protein. The mutation leads to a premature stop codon at base 1011 of SEQ ID NO:1 (base 849 of the coding sequence). This region encodes the loop linking the second and third putative membrane spanning domains of KVLQT1.

The spectrum of QTc intervals in this genotypically defined population was assessed. The mean QTc for the proband with homozygous KVLQT1 mutation was 0.54±0.05 seconds (1 individual, 8 electrocardiograms). By contrast, the QTc for individuals harboring one mutant KVLQT1 allele was 0.47±0.04 seconds (24 individuals, 1 electrocardiogram each). The mean QTc for family members without KVLQT1 mutation was 0.43±0.02 seconds (28 individuals, 1 electrocardiogram each). Although the number of homozygotes (one) in this family is not sufficient to perform a formal statistical analysis, the QTc interval of the proband (QTc of 0.54 seconds) is markedly higher than the mean for heterozygotes (QTc of 0.47 seconds). This suggests that patients having two copies of mutant KVLQT1 may have a longer QTc interval than those harboring a single mutant copy.

The family which was studied shows autosomal dominant LQT resulting from a mutation of KVLQT1. Family members harboring one mutant KVLQT1 allele have LQT but normal hearing. One member of this family had the typical features of JLN, QTc prolongation and congenital sensory deafness (Jervell and Lange-Nielsen, 1957; Fraser et al., 1964; Tesson et al., 1996). This individual presented in utero with bradycardia. She was the offspring of a consanguineous marriage and had two copies of the mutant KVLQT1 allele. It is concluded that homozygous mutation of KVLQT1 causes JLN. A person with one mutation in the paternal KVLQT1 gene and a different mutation in the maternal KVLQT1 gene will also have JLN.

Recent genetic and physiologic data support this conclusion. It has been demonstrated that mutations of KVLQT1 cause autosomal dominant LQT (Q. Wang et al., 1996). It was recently discovered that KVLQT1 subunits coassemble with minK to form cardiac $I_{Ks}$ potassium channels (Sanguinetti et al., 1996; Barhanin et al., 1996). Although most studies have focused on the function of minK in the heart, this gene is also expressed in the inner ear. MinK knockout mice are deaf and show inner ear pathology similar to that observed in individuals with JLN (Vetter et al., 1996; Friedman et al., 1966). Loss of functional minK in the ear apparently disrupts endolymph production, leading to deafness. Recently, Neyroud and colleagues showed that KVLQT1 is expressed in the stria vascularis of mouse inner ear (Neyroud et al., 1997). Other known genes located near KVLQT1 ($p57^{K1P2}$, insulin-like growth factor II, insulin, lyrosine hydroxylase and H19) are not likely to contribute to the pathology observed in the Jervell and Lange-Nielsen syndrome. These data are consistent with the finding that homozygous mutation of KVLQT1 causes deafness.

The insertion in KVLQT1 described here causes a frameshift, disrupting the coding sequence and leading to a premature stop codon. The resultant truncated protein would lack a pore region and could not function as an ion channel. Thus, the proband represents a functional knockout of KVLQT1. The result is prolonged myocellular repolarization, inhomogeneity of cardiac repolarization, increased risk of torsades de pointes arrhythmias and deafness.

It is not yet clear if KVLQT1 is the only gene responsible for JLN. Genetic heterogeneity has been identified in autosomal dominant LQT (Table 3), and Jeffery and colleagues described a JLN family that was not linked to markers on chromosome 11p15.5 (Curran et al., 1995; Wang et al., 1995; Q. Wang et al., 1996; Jeffery et al., 1992). Consistent with the presented data, Neyroud and collcagues recently reported homozygous KVLQT1 mutations associated with JLN in two kindreds (Neyroud et al., 1997). Because minK coassembles with KVLQT1 to form $I_{Ks}$ channels, the minK gene is another excellent candidate for this disorder (Sanguinetti et al., 1996; Barhanin et al., 1996).

TABLE 3

Molecular Genetics of Long QT Syndrome

| Inheritance | Locus | Chromosome | Gene |
|---|---|---|---|
| Romano-Ward Syndrome (LQT) | | | |
| autosomal dominant | LQT1 | 11p15.5 | KVLQT1 |
| | LQT2 | 7q35–36 | HERG |
| | LQT3 | 3p21–24 | SCN5A |
| | LQT4 | 4q25–27 | ? |
| | LQT5 | 21q22.1–22.2 | KCNE1 |
| Jervell and Lange Nielsen Syndrome (LQT + Deafness) | | | |
| autosomal recessive | LQT1 | 11p15.5 | KVLQT1 |

It was previously thought that family members of individuals with JLN are not at increased risk for cardiac arrhythmias (Jervell and Lange-Nielsen 1957; Fraser et al., 1964; Jervell et al., 1966; Tesson et al., 1996). Previous reports on the clinical characteristics of JLN have focused on the dramatic features observed in the probands, which generally include marked prolongation of the QTc interval, frequent tachyarrhythmias and deafness. Some studies have documented moderate QTc prolongation in family members with normal hearing, but Romano-Ward long-QT syndrome was not diagnosed (Fraser et al., 1964; Jervell et al., 1966). The family described in this study came to our attention because the proband's mother died suddenly, presumably of a cardiac arrhythmia. Phenotypic evaluation of the extended family revealed autosomal dominant inheritance of long-QT syndrome in other family members. Deafness, however, was only observed in the proband, a patient who was homozygous for the KVLQT1 mutation. Thus, one feature of the Jervell and Lange-Nielsen syndrome phenotype (deafness) is inherited as an autosomal recessive trait. QTc prolongation, by contrast, is inherited as a dominant trait but the phenotype may be more severe if both alleles are mutant. It is important to note that parents (and possibly other family members) of JLN patients are obligate heterozygotes for LQT associated mutations and are at increased risk of arrhythmia. The untimely death of the proband's mother points to the importance of electrocardiographic and genetic testing of JLN families.

EXAMPLE 5

Genomic Structure of KVLQT1

The genomic DNA of KVLQT1 was examined and the exon/intron boundaries determined for all exons.

A. Isolation of cDNA Clones

A cDNA probe containing exons 3 through 6 was used to isolate three full length KVLQT1 cDNA clones from an adult heart cDNA library prepared in the laboratory using SuperScript Choice system (GIBCO BRL).

B. Isolation of Genomic Clones

KVLQT1 P1 clones were isolated as described (Q. Wang et al., 1996). The cosmid containing exon 1 was isolated screening a human genomic cosmid library (Stratagene) with a cDNA probe from exon 1.

C. Exon/Intron Boundary Determination

All genomic clones were sequenced using primers designed to the cDNA sequences. The KVLQT1 P1 clones were cycle sequenced using ThermoSequenase (Amersham Life Science). The KVLQT1 cosmids were sequenced by the dideoxy chain termination method on an Applied Biosystems model 373A DNA sequencer. The exact exon/intron boundaries were determined by comparison of cDNA, genomic sequences, and known splice site consensus sequences.

D. Design of PCR Primers and PCR Reaction Conditions

Primers to amplify exons of the two genes were designed empirically or using OLIGO 4.0 (NBI). Amplification conditions were:

(1) 94° C. for 3 minutes followed by 30 cycles of 94° C. for 10 seconds, 58° C. for 20 seconds and 72° C. for 20 seconds and a 5 minute extension at 72° C.

(2) same as conditions in (1) except that the reactions had final concentrations of 10% glycerol and 4% formamide and were overlaid with mineral oil.

(3) 94° C. for 3 minutes followed by 5 cycles of 94° C. for 10 seconds, 64° C. for 20 seconds and 72° C. for 20 seconds and 30 cycles of 94° C. for 10 seconds, 62° C. for 20 seconds and 72° C. for 20 seconds and a 5 minute extension at 72° C.

E. KVLQT1 Genomic Structure and Primer Sets

Figure 4:
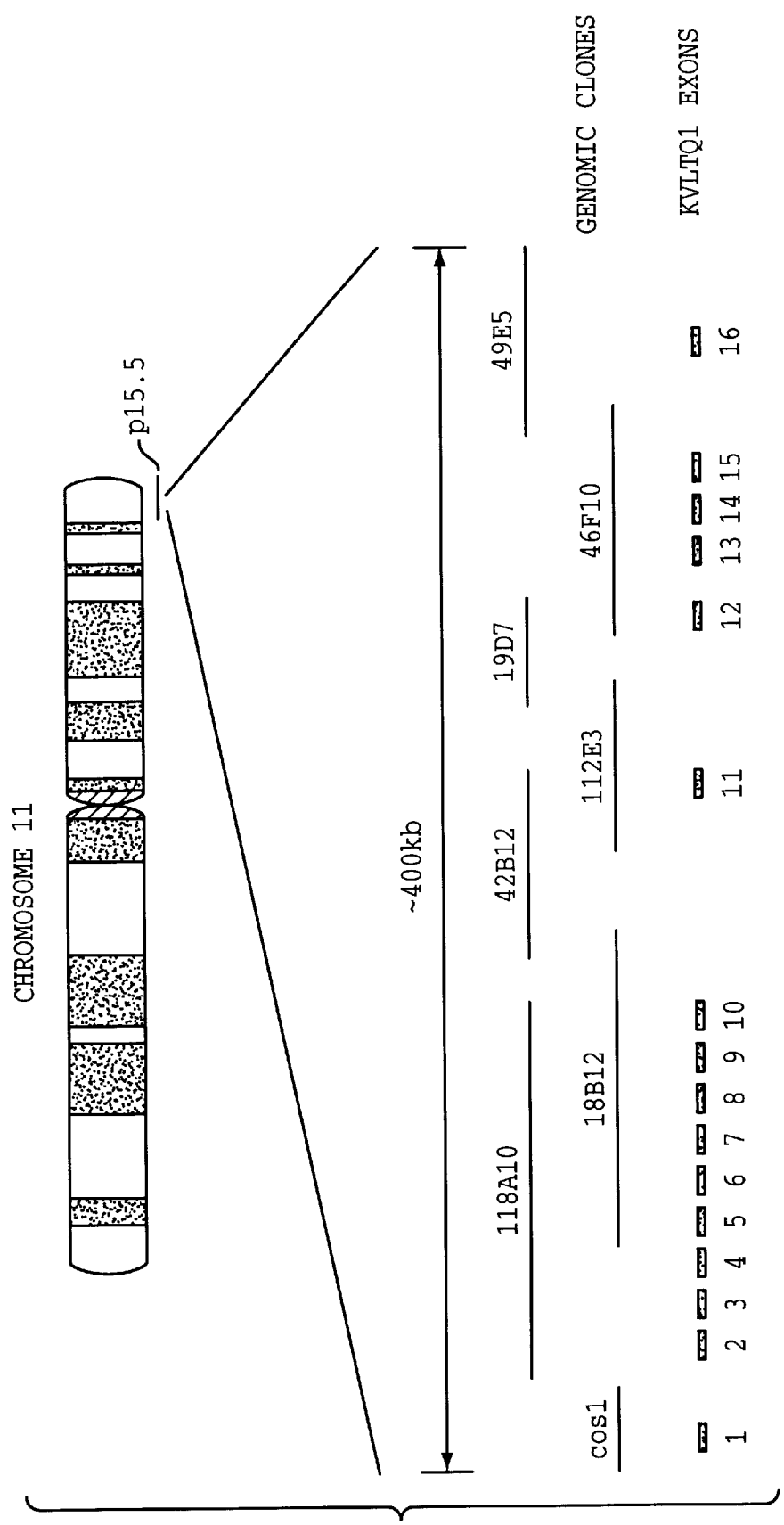
FIG. 4. Physical map and exon organization of KVLQT1. The genomic region of KVLQT1 encompasses approximately 400 kilobases. Physical map of the minimal contig of overlapping P1 clones and the cosmid containing exon 1 is shown. The location of KVLQT1 exons relative to genomic clones is indicated. Sizes of exons and distances are not drawn to scale.

Full length cDNA clones were isolated from an adult heart cDNA library. A 5'-cDNA probe generated from one of these clones was used to isolate cos1, a genomic cosmid clone containing exon 1. P1 genomic clones encompassing the rest of the KVLQT1 cDNA were previously isolated (Q. Wang et al., 1996). These genomic clones span approximately 400 kb on chromosome 11 p15.5 (FIG. 4). To determine the exon structure and exon/intron boundaries, cos1 and P1 clones 118A10, 112E3, 46F10 and 49E5 were sequenced using primers designed to the cDNA. Comparison of the genomic and cDNA sequences of KVLQT1 revealed the presence of 16 exons (FIGS. 3A–3B and Table 4). Exon size ranged from 47 bp (exon 14) to 1122 bp (exon 16). All intronic sequences contained the invariant GT and AG at the donor and acceptor splice sites, respectively (Table 4). One pair of PCR primers was designed for each of intron sequences flanking exons 2 through 16 and two pairs of primers with overlapping products were designed for exon 1 due to its large size (Table 5). These primers can be used to screen all KVLQT1 exons.

EXAMPLE 6

Mutations in KVLQT1 Associated with LQT Syndrome

Several LQT families were analyzed for the presence of mutations in KVLQT1. SSCP analyses were performed and aberrant conformers were later sequenced. The mutations seen in these studies are shown in Table 6. These mutations are not seen in persons without LQT. Persons who have at least one of these mutations in their paternal chromosome and at least one of these mutations in their maternal chromosome will have no wild-type KVLQT1 and will therefore be functionally similar to the case discussed above in which the patient was homozygous for a mutation in KVLQT1 and

TABLE 4

Intron/Exon Boundaries in KVLQT1

| Exon No. | intron/EXON[a] | EXON (total bases) | EXON/intron[a] |
|---|---|---|---|
| 1 | 5'UTR . . . ATGGCCGCGG (7) | 386+ | ACTTCGCCGTgtgagtatcg (8) |
| 2 | tgtcttgcagCTTCCTCATC (9) | 91 | CTTCTGGATGgtacgtagca (10) |
| 3 | gtccctgcagGAGATCGTGC (11) | 127 | TCCATCATCGgtgagtcatg (12) |
| 4 | cactccacagACCTCATCGT (13) | 79 | GGGCCATCAGgtgcgtctgt (14) |
| 5 | tccttcgcagGGGCATCCGC (15) | 97 | CCACCGCCAGgtgggtggcc (16) |
| 6 | tctggcctagGAGCTGATAA (17) | 141 | GTGGGGGGTGgtaagtcgga (18) |
| 7 | ctccctgcagGTCACAGTCA (19) | 111 | GCTCCCAGCGgtaggtgccc (20) |
| 8 | tccttcccagGGGATTCTTG (21) | 96 | ACTCATTCAGgtgcggtgcc (22) |
| 9 | cccacctcagACCGCATGGA (23) | 123 | GTCTGTGGTGgtgagtagcc (24) |
| 10 | ttttttttagGTAAAGAAAA (25) | 142 | GACAGTTCTGgtgagaaccc (26) |
| 11 | ttctcctcagTAAGGAAGAG (27) | 121 | ACATCTCACAgtgagtgcct (28) |
| 12 | tccactgcagGCTGCGGGAA (29) | 76 | GAAATTCCAGgtaagccctg (30) |
| 13 | tgtcccgcagCAAGCGCGGA (31) | 95 | TGCAGAGGAGgtgggcacgg (32) |
| 14 | ttctctccagGCTGGACCAG (33) | 47 | TCCGTCTCAGgtgggttct (34) |
| 15 | tcccccatagAAAAGAGCAA (35) | 62 | AGAAGACAAGgtaggctcac (36) |
| 16 | gtccccgcagGTGACGCAGC (37) | 237+ | GGGGTCCTGA . . . 3'UTR (38) |

[a]SEQ ID NO is shown in parentheses following each sequence.

TABLE 5

Primers Used to Amplify KVLQT1 Exons

| Exon No. | Forward Primer[a] | Reverse Primer[a] | Size | C[b] |
|---|---|---|---|---|
| 1 | CTCGCCTTCGCTGCAGCTC (39) | GCGCGGGTCTAGGCTCACC (40) | 334 | 2 |
| 1 | CGCCGCGCCCCCAGTTGC (41) | CAGAGCTCCCCCACACCAG (42) | 224 | 2 |
| 2 | ATGGGCAGAGGCCGTGATGCTGAC (43) | ATCCAGCCATGCCCTCAGATGC (44) | 165 | 3 |
| 3 | GTTCAAACAGGTTGCAGGGTCTGA (45) | CTTCCTGGTCTGGAAACCTGG (46) | 256 | 3 |
| 4 | CTCTTCCCTGGGGCCCTGGC (47) | TGCGGGGGAGCTTGTGGCACAG (48) | 170 | 3 |
| 5 | TCAGCCCCACACCATCTCCTTC (49) | CTGGGCCCCTACCCTAACCC (50) | 154 | 3 |
| 6 | TCCTGGAGCCCGACACTGTGTGT (51) | TGTCCTGCCCACTCCTCAGCCT (52) | 238 | 2 |
| 7 | TGGCTGACCACTGTCCCTCT (53) | CCCCAGGACCCCAGCTGTCCAA (54) | 195 | 3 |
| 8 | GCTGGCAGTGGCCTGTGTGGA (55) | AACAGTGACCAAAATGACAGTGAC (56) | 191 | 3 |
| 9 | TGGCTCAGCAGGTGACAGC (57) | TGGTGGCAGGTGGGCTACT (58) | 185 | 1 |
| 10 | GCCTGGCAGACGATGTCCA (59) | CAACTGCCTGAGGGGTTCT (60) | 216 | 1 |
| 11 | CTGTCCCCACACTTTCTCCT (61) | TGAGCTCCCCTCCCCTCCAG (62) | 195 | 1 |
| 12 | TGGCCACTCACAATCTCCT (63) | GCCTTGACACCCTCCACTA (64) | 222 | 1 |
| 13 | GGCACAGGGAGGAGAAGTG (65) | CGGCACCGCTGATCATGCA (66) | 216 | 1 |
| 14 | CCAGGGCCAGGTGTGACTG (67) | TGGGCCCAGAGTAACTGACA (68) | 119 | 2 |
| 15 | GGCCCTGATTTGGGTGTTTTA (69) | GGACGCTAACCAGAACCAC (70) | 135 | 2 |
| 16 | CACCACTGACTCTCTCGTCT (71) | CCATCCCCCAGCCCCATC (72) | 297 | 2 |

[a]SEQ ID NO is shown in parentheses following each sequence.
[b]Conditions of the PCR as described in Example 5D.

had Jervell and Lange-Nielsen syndrome. Other persons with no wild-type KVLQT1 will also have Jervell and Lange-Nielsen syndrome, regardless of whether this is due to a homozygous mutation or a result of two separate mutations affecting both sets of chromosomes.

EXAMPLE 7

Generation of Polyclonal Antibody against KVLQT1

Segments of KVLQT1 coding sequence are expressed as fusion protein in *E. coli*. The overexpressed protein is purified by gel elution and used to immunize rabbits and mice using a procedure similar to the one described by Harlow and Lane, 1988. This procedure has been shown to generate Abs against various other proteins (for example, see Kraemer et al., 1993).

Briefly, a stretch of KVLQT1 coding sequence is cloned as a fusion protein in plasmid PET5A (Novagen, Inc., Madison, Wis.). After induction with IPTG, the overexpression of a fusion protein with the expected molecular weight is verified by SDS/PAGE. Fusion protein is purified from the gel by electroelution. Identification of the protein as the KVLQT1 fusion product is verified by protein sequencing at the N-terminus. Next, the purified protein is used as immunogen in rabbits. Rabbits are immunized with 100 μg of the protein in complete Freund's adjuvant and boosted twice in 3 week intervals, first with 100 μg of immunogen in incomplete Freund's adjuvant followed by 100 μg of immunogen in PBS. Antibody containing serum is collected two weeks thereafter.

This procedure is repeated to generate antibodies against the mutant forms of the KVLQT1 gene product. These antibodies, in conjunction with antibodies to wild type KVLQT1, are used to detect the presence and the relative level of the mutant forms in various tissues and biological fluids.

EXAMPLE 8

Generation of Monoclonal Antibodies Specific for KVLQT1

Monoclonal antibodies are generated according to the following protocol. Mice are immunized with immunogen comprising intact KVLQT1 or KVLQT1 peptides (wild type or mutant) conjugated to keyhole limpet hemocyanin using glutaraldehyde or EDC as is well known.

The immunogen is mixed with an adjuvant. Each mouse receives four injections of 10 to 100 μg of immunogen and after the fourth injection blood samples are taken from the mice to determine if the serum contains antibody to the imnmunogen. Serum titer is determined by ELISA or RIA. Mice with sera indicating the presence of antibody to the immunogen are selected for hybridoma production.

Spleens are removed from immune mice and a single cell suspension is prepared (see Harlow and Lane, 1988). Cell fusions are performed essentially as described by Kohler and Milstein (1975). Briefly, P3.65.3 myeloma cells (American Type Culture Collection, Rockville, Md.) are fused with immune spleen cells using polyethylene glycol as described by Harlow and Lane (1988). Cells are plated at a density of $2\times10^5$ cells/well in 96 well tissue culture plates. Individual wells are examined for growth and the supernatants of wells with growth are tested for the presence of KVLQT1 specific antibodies by ELISA or RIA using wild type or mutant KVLQT1 target protein. Cells in positive wells are expanded and subcloned to establish and confirm monoclonality.

Clones with the desired specificities are expanded and grown as ascites in mice or in a hollow fiber system to produce sufficient quantities of antibody for characterization and assay development.

TABLE 6

Summary of KVLQT1 Mutations

| Codon | Nucleotide change | Coding effect | Mutation | Region | Kindred | No. of affected |
|---|---|---|---|---|---|---|
| 167–168 | ΔTCG | Deletion | F167W/G168Δ | S2 | K13216 | 1 |
| 178 | GCC to CCC | Missense | A178P | S2–S3 | K13119 | 1 |
| 189 | GGG to AGG | Missense | G189R | S2–53 | K2557 | 3 |
| 190 | CGG to CAG | Missense | R190Q | S2–S3 | K15019 | 2 |
| 254 | GTG to ATG | Missense | V254M | S4–S5 | K1532 | 70 |
| 273 | CTC to TTC | Missense | L273F | S5 | K1777 | 2 |
| 306 | GGG to AGG | Missense | G306R | Pore | K20926 | 1 |
| 312 | ACC to ATC | Missense | T312I | Pore | K20925 | 1 |
| 341 | GCG to GAG | Missense | A341B | S6 | K1723 | 6 |
| 341 | GCG to GAG | Missense | A341E | S6 | K2050 | 2 |
| 341 | GCG to GTG | Missense | A341V | S6 | K1807 | 6 |
| 341 | GCG to GTG | Missense | A341V | S6 | K161 | 18 |
| 341 | GCG to GTG | Missense | A341V | S6 | K162 | 18 |
| 341 | GCG to GTG | Missense | A341V | 56 | K163 | 3 |
| 341 | GCG to GTG | Missense | A341V | S6 | K164 | 2 |
| 345 | GGG to GAG | Missense | G345E | S6 | K2605 | 11 |
| 168 | GGG to AGG | Missense | G168R | S2 | K2625 | — |
| 168 | GGG to AGG | Missense | G168R | S2 | K2673 | — |
| 168 | GGG to AGG | Missense | G168R | S2 | K3698 | — |
| 314 | GGC to AGC | Missense | G314S | Pore | K19187 | — |
| 315 | TAT to TGT | Missense | Y315C | Pore | K22709 | — |
| 318 | AAGto AAC | Missense | K318N | Pore | K2762 | — |
| 353 | CTG to CCG | Missense | L353P | S6 | K3401 | — |
| 366 | CGG to TGG | Missense | R366W | C-terminus | K2824 | — |

EXAMPLE 9

Sandwich Assay for KVLQT1

Monoclonal antibody is attached to a solid surface such as a plate, tube, bead or particle. Preferably, the antibody is attached to the well surface of a 96-well ELISA plate. 100 µl sample (e.g., serum, urine, tissue cytosol) containing the KVLQT1 peptide/protein (wild-type or mutants) is added to the solid phase antibody. The sample is incubated for 2 hrs at room temperature. Next the sample fluid is decanted, and the solid phase is washed with buffer to remove unbound material. 100 µL of a second monoclonal antibody (to a different determinant on the KVLQT1 peptide/protein) is added to the solid phase. This antibody is labeled with a detector molecule (e.g., $^{125}$I, enzyme, fluorophore, or a chromophore) and the solid phase with the second antibody is incubated for two hours at room temperature. The second antibody is decanted and the solid phase is washed with buffer to remove unbound material.

The amount of bound label, which is proportional to the amount of KVLQT1 peptide/protein present in the sample, is quantified. Separate assays are performed using monoclonal antibodies which are specific for the wild-type KVLQT1 as well as monoclonal antibodies specific for each of the mutations identified in KVLQT1.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

LIST OF REFERENCES

Altschul S F, et al. (1997). *Nucl. Acids Res.* 25:3389–3402.
Anand, R (1992). *Techniques for the Analysis of Complex Genomes*, (Academic Press).
Anderson W F, et al. (1980). *Proc. Natl. Acad Sci. USA* 77:5399–5403.
Antzelevitch C and Sicouri S (1994). *J. Am. Col. Card* 23:259–277.
Attali B, et al. (1993). *Nature* 365:850–852.
Attwell D, et al. (1979). *Pflugers Arch.* 379:137–142.
Ausubel F M, et al. (1992). *Current Protocols in Molecular Biology*, (John Wiley and Sons, New York, N.Y.).
Bandyopadhyay P K and Temin H M (1984). *Mol. Cell. Biol.* 4:749–754.
Barhanin J, et al. (1996). *Nature* 384:78–80.
Bartel P L, et al. (1993). "Using the 2-hybrid system to detect protein-protein interactions." In *Cellular Interactions in Development: A Practical Approach*, Oxford University Press, pp.153–179.
Beaucage S L and Caruthers M H (1981). *Tetra. Letts.* 22:1859–1862.
Berglund P, et al. (1993). *Biotechnology* 11:916–920.
Berkner K L, et al. (1988). *BioTechniques* 6:616–629.
Berkner K L (1992). *Curr. Top. Microbiol. Immunol.* 158:39–66.
Bonnan S (1996). *Chemical & Engineering News*, December 9 issue, pp. 42–43.
Breakefield X O and Geller A l (1987). *Mol. Neurobiol.* 1:337–371.
Brinster R L, et al. (1981). *Cell* 27:223–231.
Bruggemann A, et al. (1993). *Nature* 365:445–448.
Buchschacher G L and Panganiban A T (1992). *J. Virol.* 66:2731–2739.
Busch A E, et al. (1992). *Science* 255:1705–1707.
Capecchi M R (1989). *Science* 244:1288.
Cardiac Arrhythmia Suppression Trial II Investigators (1992). *N. Engl. J. Med.* 327:227–233.
Cariello N F (1988). *Am. J. Human Genetics* 42:726–734.
Chee M, et al. (1996). *Science* 274:610–614.
Chevray P M and Nathans D N (1992). *Proc. Natl. Acad. Sci. USA* 89:5789–5793.
Compton J (1991). *Nature* 350:91–92.
Conner B J, et al. (1983). *Proc. Natl. Acad. Sci. USA* 80:278–282.
Costantini F and Lacy E (1981). *Nature* 294:92–94.
Cotten M, et al. (1990). *Proc. Natl. Acad. Sci. USA* 87:4033–4037.
Cotton R G, et al. (1988). *Proc. Natl. Acad. Sci. USA* 85:4397–4401.
Covarrubias M, et al. (1991). *Neuron* 7:763–773.
Culver K W, et al. (1992). *Science* 256:1550–1552.
Culver K (1996). *Gene Therapy: A Primer for Physicians*, 2nd Ed., Mary Ann Liebert.
Curiel D T, et al. (1991). *Proc. Natl. Acad. Sci. USA* 88:8850–8854.
Curiel D T, et al. (1992). *Hum. Gene Ther.* 3:147–154.
Curran M E, et al. (1995). *Cell* 80:795–804.
DeRisi J, et al. (1996). *Nat. Genet.* 14:457–460.
Deutscher M (1990). *Meth. Enzymology* 182:83–89 (Academic Press, San Diego, Calif.).
Donehower L A, et al. (1992). *Nature* 356:215.
Duggal P et al. (1998). *Circulation* 97:142–146.
Editorial (1996). *Nature Genetics* 14:367–370.
Elghanian R, et al. (1997). *Science* 277:1078–1081.
*Enhancers and Eukaryotic Gene Expression*, Cold Spring Harbor Press, Cold Spring Harbor, N.Y. (1983).
Erickson J, et al. (1990). *Science* 249:527–533.
Fahy E, et al. (1991). *PCR Methods Appl.* 1:25–33.
Feigner P L, et al. (1987). *Proc. Natl. Acad. Sci. USA* 84:7413–7417.
Fields S and Song O-K (1989). *Nature* 340:245–246.
Fiers W, et al. (1978). *Nature* 273:113–120.
Fink D J, et al. (1992). *Hum. Gene Ther.* 3:11–19.
Fink D J, et al. (1996). *Ann. Rev. Neurosci.* 19:265–287.
Finkelstein J, et al. (1990). *Genomics* 7:167–172.
Fodor S P A (1997). *Science* 277:393–395.
Fraser G R, et al. (1964). *Quart. J. Med.* 33:361–385.
Freese A, et al. (1990). *Biochem. Pharmacol.* 40:2189–2199.
Friedman I, et al. (1966). *J. Laryngol. Otol.* 80:451–470.
Friedman T (1991). In *Therapy for Genetic Diseases*, T. Friedman, ed., Oxford University Press, pp. 105–121.
Gellens M, et al. (1992). *Proc. Naci. Acad. Sci. USA* 89:554–558.
George A L, et al. (1995). *Cytogenet. Cell. Genet.* 68:67–70.
Glover D (1985). *DNA Cloning*, I and II (Oxford Press).
Goding (1986). *Monoclonal Antibodies: Principles and Practice*, 2d ed. (Academic Press, N.Y.).
Godowski P J, et al. (1988). *Science* 241:812–816.
Goldstein S A N and Miller C (1991). *Neuron* 7:403–408.
Gordon J W, et al. (1980). *Proc. Natl. Acad. Sci. USA* 77:7380–7384.
Gorziglia M and Kapikian A Z (1992). *J. Virol.* 66:4407–4412.
Graham F L and van der Eb A J (1973). *Virology* 52:456–467.
Grompe M (1993). *Nature Genetics* 5:111–117.
Grompe M, et al. (1989). *Proc. Natl. Acad. Sci. USA* 86:5855–5892.
Guthrie G and Fink G R (1991). *Guide to Yeast Genetics and Molecular Biology* (Academic Press).
Hacia J G, et al. (1996). *Nature Genetics* 14:441–447.
Harlow E and Lane D (1988). *Antibodies: A Laboratory Manual* (Cold Spring Harbor Laboratory, Cold Spring Harbor, N.Y.).
Hasty P K, et al. (1991). *Nature* 350:243.
Hausdorff S F, et al. (1991). *Biochem.* 30:3341–3346.

Helseth E, et al. (1 990). *J. Virol.* 64:2416–2420.
Hodgson J (1991). *Bio/Technology* 9:19–21.
Holland J J (1993). *Anaesthesia* 48:149–151.
Huse W D, et al. (1989). *Science* 246:1275–1281.
Innis M A, et al. (1990). *PCR Protocols: A Guide to Methods and Applications* (Academic Press, San Diego).
Jablonski E, et al. (1986). *Nucl. Acids Res.* 14:6115–6128.
Jakoby W B and Pastan I H (eds.) (1979). *Cell Culture. Methods in Enzymology* volume 58 (Academic Press, Inc., Harcourt Brace Jovanovich (New York)).
January C T and Riddle J M (1989). *Circ. Res.* 64:977–990.
Jeffery S, et al. (1992). *Lancet* 339:255.
Jervell A and Lange-Nielsen F (1957). *Am. Heart J.* 54:59–68.
Jervell A, et al. (1966). *Am. Heart J.* 72:582–593.
Jiang C, et al. (1 994). *Nat. Genet.* 8: 141–147.
Johnson P A, et al. (1992). *J. Virol.* 66:2952–2965.
Johnson, et al. (1993). "Peptide Turn Mimetics" in *Biotechnology and Pharmacy*, Pezzuto et al., eds., Chapman and Hall, New York.
Kaneda Y, et al. (1989). *J. Biol. Chem.* 264:12126–12129.
Kanehisa M (1984). *Nucl. Acids Res.* 12:203–213.
Kannel W B, et al. (1987). *Am. Heart J.* 113:799–804.
Keating M (1992). *Circulation* 85:1973–1986.
Keating M T, et al. (1991a). *Science* 252:704–706.
Keating M T, et al. (1991b). *Am. J. Hum. Genet.* 49:1335–1339.
Kinszler K W, et al. (1991). *Science* 251:1366–1370.
Kohler G and Milstein C (1975). *Nature* 256:495–497.
Kraemer F B, et al. (1993). *J. Lipid Res.* 34:663–672.
Kubo T, et al. (1988). *FFBS Lett.* 241:119.
Kyte J and Doolittle R F (1982). *J. Mol. Biol.* 157:105–132.
Landegren U, et al. (1988). *Science* 242:229–237.
Lathrop, G M, et al. (1985). *Am. J. Hum. Genet.* 37:482–498.
Lee J E, et al. (1995). *Science* 268:836–844.
Lesage F, et al. (1993). *Receptors and Channels* 1:143–152.
Lim C S, et al. (1991). *Circulation* 83:2007–2011.
Lipshutz R J, et al. (1995). *BioTechniques* 19:442–447.
Lockhart D J, et al. (1996). *Nature Biotechnology* 14:1675–1680.
MacKinnon R (1991). *Nature* 350:232–235.
MacKinnon R, et al. (1993). *Science* 262:757–759.
Madzak C, et al. (1992). *J. Gen. Virol.* 73:1533–1536.
Maniatis T, et al. (1982). *Molecular Cloning: A Laboratory Manual* (Cold Spring Harbor Laboratory, Cold Spring Harbor, N.Y.).
Mann R and Baltimore D (1985). *J. Virol.* 54:401–407.
Margolskee R F (1992). *Curr. Top. Microbiol. Immunol.* 158:67–95.
Martin R, et al. (1990). *BioTechniques* 9:762–768.
Matteucci M D and Caruthers M H (1981). *J. Anm. Chem. Soc.* 103:3185.
Matthews J A and Kricka L J (1988). *Anal. Biochem.* 169:1.
Merrifield B (1963). *J. Am. Chem. Soc.* 85:2149–2156.
Metzger D, et al. (1988). *Nature* 334:31–36.
Mifflin T E (1989). *Clinical Chem.* 35:1819–1825.
Miller A D (1992). *Curr. Top. Microbiol. Immunol.* 158:1–24.
Miller A D, et al. (1985). *Mol. Cell. Biol.* 5:431–437.
Miller A D, et al. (1988). *J. Virol.* 62:4337–4345.
Modrich P (1991). *Ann. Rev. Genet.* 25:229–253.
Mombaerts P, et al. (1992). *Cell* 68:869.
Moss A J and McDonald J (1971). *N. Engl. J. Med.* 285:903–904.
Moss A J, et al. (1985). *Circulation* 71:17–21.
Moss A J, et al. (1991). *Circulation* 84:1136–1144.
Moss B (1992). *Curr. Top. Microbiol. Immunol.* 158:25–38.
Moss B (1996). *Proc. Natl. Acad. Sci. USA* 93:11341–11348.
Muzyczka N (1992). *Curr. Top. Microbiol. Immunol.* 158:97–129.
Nabel E G, et al. (1990). *Science* 249:1285–1288.
Nabel (1992). *Hum. Gene Ther.* 3:399–410.
Naldini L, et al. (1996). *Science* 272:263–267.
Newton C R, et al. (1989). *Nucl Acids Res.* 17:2503–2516.
Neyroud N, et al. (1997). *Nat. Genet.* 15:186–189.
Nguyen Q, et al. (1992). *BioTechniques* 13:116–123.
Novack D F, et al. (1986). *Proc. Natl. Acad. Sci. USA* 83:586–590.
Ohi S, et al. (1990). *Gene* 89:279–282.
Orita M, et al. (1989). *Proc. Natl. Acad. Sci. USA* 86:2766–2770.
Page K A, et al. (1990). *J. Virol.* 64:5270–5276.
Pellicer A, et al. (1980). *Science* 209:1414–1422.
Petropoulos C J, et al. (1992). *J. Virol.* 66:3391–3397.
Philpott K L, et al. (1992). *Science* 256:1448.
Quantin B, et al. (1992). *Proc. Natl. Acad. Sci. USA* 89:2581–2584.
*Remington's Pharmaceutical Sciences*, 18th Ed. (1990, Mack Publishing Co., Easton, Pa.).
Rigby P W J, et al. (1977). *J. Mol. Biol.* 113:237–251.
Romano C (1965). *Lancet* 1658–659.
Romano C, et al. (1963). *Clin. Pediatr.* 45:656–683.
Rosenfeld M A, et al. (1992). *Cell* 68:143–155.
Ruano G and Kidd K K (1989). *Nucl. Acids Res.* 17:8392.
Russell D and Hirata R (1998). *Nature Genetics* 18:323–328.
Sambrook J, et al. (1989). *Molecular Cloning: A Laboratory Manual*, 2nd Ed. (Cold Spring Harbor Laboratory, Cold Spring Harbor, N.Y.).
Sanguinetti M C, et al. (1996). *Nature* 384:80–83.
Scharf S J, et al. (1986). *Science* 233:1076–1078.
Schneider G, et al. (1998). *Nature Genetics* 18:180–183.
Schott J, et al. (1995). *Am. J. Hum. Genet.* 57:1114–1122.
Schultze-Bahr E, et al. (1997). *Nat. Genet.* 17:267–268.
Schwartz P J, et al. (1975). *Am. Heart.J.* 109:378–390.
Schwartz P J, et al. (1994). "The long QT syndrome." In *Cardiac Electrophysiology: from cell to bedside.* D. P. Zipes and J. Jalife eds. (W.B. Sanders Company) pp.788–811.
Scopes R (1982). *Protein Purification: Principles and Practice*, (Springer-Verlag, N.Y.).
Sheffield V C, et al. (1989). *Proc. Natl. Acad. Sci. USA* 86:232–236.
Sheffield V C, et al. (1991). *Am. J. Hum. Genet.* 49:699–706.
Shenk T E, et al. (1975). *Proc. Natl. Acad. Sci. USA* 72:989–993.
Shimada T, et al. (1991). *J. Clin. Invest.* 88:1043–1047.
Shinkai Y, et al. (1992). *Cell* 68:855.
Shoemaker D D, et al. (1996). *Nature Genetics* 14:450–456.
Snouwaert J N, et al. (1 992). *Science* 257:1083.
Sorge J, et al. (1984). *Mol. Cell. Biol.* 4:1730–1737.
Spargo C A, et al. (1996). *Mol. Cell. Probes* 10:247–256.
Splawski I, et al. (1997a). *N. Engl. J. Med.* 336:1562–1567.
Splawski I, et al. (1997b). *Nat. Genet.* 17:338–340.
Stewart M J, et al. (1992). *Hum. Gene Ther.* 3:267–275.
Stratford-Perricaudet L D, et al. (1990). *Hum. Gene Ther.* 1:241–256.
Surawicz B (1989). *J. Am. Coll. Cardiol.* 14:172–184.
Takumi T, et al. (1988). *Science* 242:1042–1045.
Takumi T, et al. (1991). *J. Biol. Chem.* 266:22192–22198.
Tesson F, et al. (1996). *J. Mol. Cell. Cardiol.* 28:2051–2055.
Till J A, et al. (1988). *Am. J. Cardiol.* 62:1319–1321.

Tyson J, et al. (1997). *Hum. Mol. Genet.* 6:2179–2185.
Valancius V and Smithies O (1991). *Mol. Cell Biol.* 11:1402.
Vetter D E, et al. (1996). *Neuron* 17:1251–1264.
Vincent G M, et al. (1992). *N. Engl. J. Med.* 327:846–852.
Wagner E, et al. (1991). *Proc. Natl. Acad. Sci. USA* 88:4255–4259.
Wagner E, et al. (1990). *Proc. Nail Acad Sci. USA* 87:3410–3414.
Walker G T, et al., (1992). *Nucl. Acids Res.* 20:1691–1696.
Wang K W and Goldstein S A (1995). *Neuron* 14:1303–1309.
Wang K W, et al. (1996). *Neuron* 16:571–577.
Wang C Y and Huang L (1989). *Biochemistry* 28:9508–9514.
Wang Q, et al. (1995). *Cell* 80:805–811.
Wang Q, et al. (1996). *Nat. Genet.* 12:17–23.
Ward O C (1964). *J. Ir. Med. Assoc.* 54:103–106.
Warmke J E and Ganetzky B (1994). *Proc. Natl. Acad. Sci.* 91:3438–3442.
Wartell R M, et al. (1990). *Nucl. Acids Res.* 18:2699–2705.
Wells J A (1991). *Methods Enzymol.* 202:390–411.
Wetmur J G and Davidson N (1968). *J. Mol. Biol.* 31:349–370.
White M B, et al. (1992). *Genomics* 12:301–306.
White R and Lalouel J M (1988). *Annu. Rev. Genet.* 22:259–279.
Wilkinson G W and Akrigg A (1992). *Nucleic Acids Res.* 20:2233–2239.
Willich S N, et al. (1987). *Am. J. Cardiol.* 60:801–806.
Wolff J A, et al. (1990). *Science* 247:1465–1468.
Wolff J A, et al. (1991). *BioTechniques* 11:474–485.
Wu D Y and Wallace R B (1989). *Genomics* 4:560–569.
Wu C H, et al. (1989). *J. Biol. Chem.* 264:16985–16987.
Yang W P, et al. (1997). *Proc. Natl. Acad, Sci. USA* 94:4017–4021.
Zenke M, et al. (1990). *Proc. Natl. Acad. Sci. USA* 87:3655–3659.
Zipes D P (1987). *Am. J. Cardiol.* 59:26E-31E.

PATENTS AND PATENT APPLICATIONS

European Patent Application Publication No. 0332435.
EPO Publication No. 225,807.
Hitzeman et al., EP 73,675A.
EP 425,731 A.
WO 84/03564.
WO 90/07936.
WO 92/19195.
WO 93/07282.
WO 94/25503.
WO 95/01203.
WO 95/05452.
WO 96/02286.
WO 96/02646.
WO 96/11698.
WO 96/40871.
WO 96/40959.
WO 97/02048.
WO 97/12635.
U.S. Pat. No. 3,817,837.
U.S. Pat. No. 3,850,752.
U.S. Pat. No. 3,939,350.
U.S. Pat. No. 3,996,345.
U.S. Pat. No. 4,275,149.
U.S. Pat. No. 4,277,437.
U.S. Pat. No. 4,366,241.
U.S. Pat. No. 4,376,110.
U.S. Pat. No. 4,486,530.
U.S. Pat. No. 4,554,101.
U.S. Pat. No. 4,683,195.
U.S. Pat. No. 4,683,202.
U.S. Pat. No. 4,816,567.
U.S. Pat. No. 4,868,105.
U.S. Pat. No. 5,252,479.
U.S. Pat. No. 5,270,184.
U.S. Pat. No. 5,409,818.
U.S. Pat. No. 5,436,146.
U.S. Pat. No. 5,455,166.
U.S. Pat. No. 5,550,050.
U.S. Pat. No. 5,691.198.
U.S. Pat. No. 5,735,500.
U.S. Pat. No. 5,747,469.

What is claimed is:

1. An isolated DNA fragment or polynucleotide comprising DNA coding for a mutant polypeptide of SEQ ID NO:80 which causes Jervell and Lange-Nielsen Syndrome (JLN) when homozygous.

2. An isolated DNA according to claim 1 wherein said isolated DNA comprises an insertion of a single base between nucleotides 282 and 283 of SEQ ID NO:79.

3. An isolated DNA according to claim 1 wherein said isolated DNA comprises a stop codon at or before nucleotide 564 of SEQ ID NO:79.

4. A nucleic acid probe which will hybridize to the DNA of claim 1 but will not hybridize to DNA encoding a polypeptide of SEQ ID NO:80 under stringent conditions.

5. A nucleic acid probe which will hybridize to the DNA of claim 2 but will not hybridize to DNA encoding a polypeptide of SEQ ID NO:80 under stringent conditions.

6. A method for diagnosing a polymorphism which causes JLN comprising the steps of:
   a) hybridizing under stringent conditions a probe of claim 4 to a patient's sample of DNA or RNA, and
   b) hybridizing under stringent conditions a probe, which hybridizes under stringent conditions to a DNA encoding a polypeptide of SEQ ID NO:80 but not to DNA coding for a polypeptide of SEQ ID NO:80 comprising a mutation which causes Jervell and Lange-Nielsen Syndrome when homozygous, to a patient's sample of DNA or RNA,
wherein the presence of a hybridization signal in step (a) but not in step (b) is indicative of the presence of JLN.

7. A method for diagnosing a polymorphism which causes JLN comprising the steps of:
   a) hybridizing under stringent conditions a probe of claim 5 to a patient's sample of DNA or RNA, and
   b) hybridizing under stringent conditions a probe, which under stringent conditions hybridizes to nucleic acid of SEQ ID NO:79 but not to DNA encoding a polypeptide of SEQ ID NO:80 comprising a mutation which causes Jervell and Lange-Nielsen Syndrome when homozygous wherein said DNA encoding a polypeptide of SEQ ID NO:80 comprising a mutation which causes Jervell and Lang-Nielsen Syndrome comprises an insertion of a single base between nucleotides 282 and 283 of SEQ ID NO:79, to a patient's sample of DNA or RNA,
wherein the presence of a hybridization signal in step (a) but not in step (b) is indicative of the presence of JLN.

8. A method according to claim 6 wherein the patient's DNA or RNA has been amplified.

9. A method according to claim 7 wherein the patient's DNA or RNA has been amplified.

10. A method according to claim 8 wherein hybridization is performed in situ.

11. A method according to claim 9 wherein hybridization is performed in situ.

12. A method for diagnosing a polymorphism which causes JLN comprising:
   a) amplifying a portion of a gene or RNA encoding a polypeptide of SEQ ID NO:80 to obtain an amplified portion wherein said portion comprises base 282 of SEQ ID NO:79,
   b) measuring the size of said amplified portion, and
   c) determining whether an insertion has occurred,
wherein the presence of said insertion is indicative of JLN when it is homozygous.

13. A method for diagnosing a polymorphism which causes JLN when a person is homozygous for said polymorphism, said method comprising using a single-stranded conformation polymorphism technique to assay for said polymorphism.

14. The method of claim 13 wherein said polymorphism is an insertion of a single base between nucleotides 282 and 283 of SEQ ID NO:79.

15. A method for diagnosing in a person a polymorphism which causes JLN comprising:
   a) amplifying a portion of a gene or RNA encoding a polypeptide of SEQ ID NO:80 to produce an amplified portion wherein said portion comprises base number 282 of SEQ ID NO:79, and
   b) sequencing said portion wherein an insertion of a single base in both copies of said person's gene or RNA as compared to a gene of SEQ ID NO:79 is indicative of JLN.

16. A method for diagnosing a polymorphism which causes JLN comprising identifying a mismatch between a patient's DNA or RNA and a wild-type DNA or RNA probe wherein said probe hybridizes to the region of DNA encompassing nucleotides 282–283 of SEQ ID NO:79.

17. The method of claim 16 wherein the mismatch is identified by an RNase assay.

18. A cell transfected with the DNA of claim 1.

19. A cell transfected with the DNA of claim 2.

20. A cell transfected with the DNA of claim 3.

21. A cell transfected with RNA encoding human mutant KVLQT1.

22. A cell according to claim 21 wherein said mutant KVLQT1 contains a mutation which results in a stop codon at or before base 564 SEQ ID NO:79.

23. A cell according to claim 22 wherein said mutation is addition of a single base between nucleotides 282 and 283 of SEQ ID NO:79.

24. A method for diagnosing a polymorphism which causes JLN comprising sequencing the KVLQT1 genes in a patient's sample of DNA to determine the presence or absence of a mutation which causes JLN when homozygous.

25. The method according to claim 24 wherein said mutation is insertion of a single base between nucleotides 282 and 283 of SEQ ID NO:79.

26. The method according to claim 24 wherein said patient's sample of DNA has been amplified.

27. The method according to claim 25 wherein said patient's sample of DNA has been amplified.

28. A method for diagnosing a polymorphism which causes JLN comprising sequencing the KVLQT1 RNA in a patient's sample of RNA to determine the presence or absence of a mutation which causes JLN when homozygous.

29. The method according to claim 28 wherein said mutation is insertion of a single base between nucleotides 282 and 283 of SEQ ID NO:79.

30. A method for diagnosing a polymorphism which causes JLN comprising determining the KVLQT1 gene sequence in a patient by preparing cDNA from RNA taken from the patient and sequencing said cDNA to determine the presence or absence of a mutation which causes JLN, wherein if said mutation is homozygous then JLN is present.

31. The method according to claim 30 wherein said mutation is addition of a single base between nucleotides 282 and 283 of SEQ ID NO:79.

32. A nucleic acid vector comprising DNA coding for a mutant human KVLQT1 polypeptide which causes JLN.

33. The vector of claim 32 wherein said DNA comprises an insertion of a single base between nucleotides 282 and 283 of SEQ ID NO:79.

34. A method for diagnosing the presence of JLN wherein said method comprises determining the presence of a mutation in each chromosomal copy of KVLQT1 wherein if a person has a mutation in each copy then said person has JLN.

* * * * *

SEQUENCE LISTING

```
<160> NUMBER OF SEQ ID NOS: 80

<210> SEQ ID NO 1
<211> LENGTH: 3181
<212> TYPE: DNA
<213> ORGANISM: Homo sapiens
<220> FEATURE:
<221> NAME/KEY: CDS
<222> LOCATION: (163)..(2190)

<400> SEQUENCE: 1 ctgcccctc cggcccgcc ccgagcgccc gggctgggcc ggcagcggcc ccccgcggcg      60
gggctggcag cagtggctgc ccgcactgcg cccgggcgct cgccttcgct gcagctcccg     120
gtgccgccgc tcgggccggc cccccggcag gccctcctcg tt atg gcc gcg gcc      174
                                               Met Ala Ala Ala
                                                 1 tcc tcc ccg ccc agg gcc gag agg aag cgc tgg ggt tgg ggc cgc ctg    222
Ser Ser Pro Pro Arg Ala Glu Arg Lys Arg Trp Gly Trp Gly Arg Leu
```

-continued

```
      5                    10                   15                   20
cca ggc gcc cgg cgg ggc agc gcg ggc ctg gcc aag aag tgc ccc ttc        270
Pro Gly Ala Arg Arg Gly Ser Ala Gly Leu Ala Lys Lys Cys Pro Phe
             25                  30                  35 tcg ctg gag ctg gcg gag ggc ggc ccg gcg ggc ggc gcg ctc tac gcg        318
Ser Leu Glu Leu Ala Glu Gly Gly Pro Ala Gly Gly Ala Leu Tyr Ala
             40                  45                  50 ccc atc gcg ccc ggc gcc cca ggt ccc gcg ccc cct gcg tcc ccg gcc        366
Pro Ile Ala Pro Gly Ala Pro Gly Pro Ala Pro Pro Ala Ser Pro Ala
             55                  60                  65 gcg ccc gcc gcg ccc cca gtt gcc tcc gac ctt ggc ccg cgg ccg ccg        414
Ala Pro Ala Ala Pro Pro Val Ala Ser Asp Leu Gly Pro Arg Pro Pro
             70                  75                  80 gtg agc cta gac ccg cgc gtc tcc atc tac agc acg cgc cgc ccg gtg        462
Val Ser Leu Asp Pro Arg Val Ser Ile Tyr Ser Thr Arg Arg Pro Val
 85                  90                  95                  100 ttg gcg cgc acc cac gtc cag ggc cgc gtc tac aac ttc ctc gag cgt        510
Leu Ala Arg Thr His Val Gln Gly Arg Val Tyr Asn Phe Leu Glu Arg
                 105                 110                 115 ccc acc ggc tgg aaa tgc ttc gtt tac cac ttc gcc gtc ttc ctc atc        558
Pro Thr Gly Trp Lys Cys Phe Val Tyr His Phe Ala Val Phe Leu Ile
                 120                 125                 130 gtc ctg gtc tgc ctc atc ttc agc gtg ctg tcc acc atc gag cag tat        606
Val Leu Val Cys Leu Ile Phe Ser Val Leu Ser Thr Ile Glu Gln Tyr
                 135                 140                 145 gcc gcc ctg gcc acg ggg act ctc ttc tgg atg gag atc gtg ctg gtg        654
Ala Ala Leu Ala Thr Gly Thr Leu Phe Trp Met Glu Ile Val Leu Val
                 150                 155                 160 gtg ttc ttc ggg acg gag tac gtg gtc cgc ctc tgg tcc gcc ggc tgc        702
Val Phe Phe Gly Thr Glu Tyr Val Val Arg Leu Trp Ser Ala Gly Cys
165                 170                 175                 180 cgc agc aag tac gtg ggc ctc tgg ggg cgg ctg cgc ttt gcc cgg aag        750
Arg Ser Lys Tyr Val Gly Leu Trp Gly Arg Leu Arg Phe Ala Arg Lys
                 185                 190                 195 ccc att tcc atc atc gac ctc atc gtg gtc gtg gcc tcc atg gtg gtc        798
Pro Ile Ser Ile Ile Asp Leu Ile Val Val Val Ala Ser Met Val Val
                 200                 205                 210 ctc tgc gtg ggc tcc aag ggg cag gtg ttt gcc acg tcg gcc atc agg        846
Leu Cys Val Gly Ser Lys Gly Gln Val Phe Ala Thr Ser Ala Ile Arg
                 215                 220                 225 ggc atc cgc ttc ctg cag atc ctg agg atg cta cac gtc gac cgc cag        894
Gly Ile Arg Phe Leu Gln Ile Leu Arg Met Leu His Val Asp Arg Gln
                 230                 235                 240 gga ggc acc tgg agg ctc ctg ggc tcc gtg gtc ttc atc cac cgc cag        942
Gly Gly Thr Trp Arg Leu Leu Gly Ser Val Val Phe Ile His Arg Gln
245                 250                 255                 260 gag ctg ata acc acc ctg tac atc ggc ttc ctg ggc ctc atc ttc tcc        990
Glu Leu Ile Thr Thr Leu Tyr Ile Gly Phe Leu Gly Leu Ile Phe Ser
                 265                 270                 275 tcg tac ttt gtg tac ctg gct gag aag gac gcg gtg aac gag tca ggc       1038
Ser Tyr Phe Val Tyr Leu Ala Glu Lys Asp Ala Val Asn Glu Ser Gly
                 280                 285                 290 cgc gtg gag ttc ggc agc tac gca gat gcg ctg tgg tgg ggg gtg gtc       1086
Arg Val Glu Phe Gly Ser Tyr Ala Asp Ala Leu Trp Trp Gly Val Val
                 295                 300                 305 aca gtc acc acc atc ggc tat ggg gac aag gtg ccc cag acg tgg gtc       1134
Thr Val Thr Thr Ile Gly Tyr Gly Asp Lys Val Pro Gln Thr Trp Val
                 310                 315                 320 ggg aag acc atc gcc tcc tgc ttc tct gtc ttt gcc atc tcc ttc ttt       1182
```

```
                                                                          -continued Gly Lys Thr Ile Ala Ser Cys Phe Ser Val Phe Ala Ile Ser Phe Phe
325                 330                 335                 340 gcg ctc cca gcg ggg att ctt ggc tcg ggg ttt gcc ctg aag gtg cag      1230
Ala Leu Pro Ala Gly Ile Leu Gly Ser Gly Phe Ala Leu Lys Val Gln
                345                 350                 355 cag aag cag agg cag aag cac ttc aac cgg cag atc ccg gcg gca gcc      1278
Gln Lys Gln Arg Gln Lys His Phe Asn Arg Gln Ile Pro Ala Ala Ala
        360                 365                 370 tca ctc att cag acc gca tgg agg tgc tat gct gcc gag aac ccc gac      1326
Ser Leu Ile Gln Thr Ala Trp Arg Cys Tyr Ala Ala Glu Asn Pro Asp
    375                 380                 385 tcc tcc acc tgg aag atc tac atc cgg aag gcc ccc cgg agc cac act      1374
Ser Ser Thr Trp Lys Ile Tyr Ile Arg Lys Ala Pro Arg Ser His Thr
390                 395                 400 ctg ctg tca ccc agc ccc aaa ccc aag aag tct gtg gtg gta aag aaa      1422
Leu Leu Ser Pro Ser Pro Lys Pro Lys Lys Ser Val Val Val Lys Lys
405                 410                 415                 420 aaa aag ttc aag ctg gac aaa gac aat ggg gtg act cct gga gag aag      1470
Lys Lys Phe Lys Leu Asp Lys Asp Asn Gly Val Thr Pro Gly Glu Lys
                425                 430                 435 atg ctc aca gtc ccc cat atc acg tgc gac ccc cca gaa gag cgg cgg      1518
Met Leu Thr Val Pro His Ile Thr Cys Asp Pro Pro Glu Glu Arg Arg
        440                 445                 450 ctg gac cac ttc tct gtc gac ggc tat gac agt tct gta agg aag agc      1566
Leu Asp His Phe Ser Val Asp Gly Tyr Asp Ser Ser Val Arg Lys Ser
    455                 460                 465 cca aca ctg ctg gaa gtg agc atg ccc cat ttc atg aga acc aac agc      1614
Pro Thr Leu Leu Glu Val Ser Met Pro His Phe Met Arg Thr Asn Ser
470                 475                 480 ttc gcc gag gac ctg gac ctg gaa ggg gag act ctg ctg aca ccc atc      1662
Phe Ala Glu Asp Leu Asp Leu Glu Gly Glu Thr Leu Leu Thr Pro Ile
485                 490                 495                 500 acc cac atc tca cag ctg cgg gaa cac cat cgg gcc acc att aag gtc      1710
Thr His Ile Ser Gln Leu Arg Glu His His Arg Ala Thr Ile Lys Val
                505                 510                 515 att cga cgc atg cag tac ttt gtg gcc aag aag aaa ttc cag caa gcg      1758
Ile Arg Arg Met Gln Tyr Phe Val Ala Lys Lys Lys Phe Gln Gln Ala
        520                 525                 530 cgg aag cct tac gat gtg cgg gac gtc att gag cag tac tcg cag ggc      1806
Arg Lys Pro Tyr Asp Val Arg Asp Val Ile Glu Gln Tyr Ser Gln Gly
    535                 540                 545 cac ctc aac ctc atg gtg cgc atc aag gag ctg cag agg agg ctg gac      1854
His Leu Asn Leu Met Val Arg Ile Lys Glu Leu Gln Arg Arg Leu Asp
550                 555                 560 cag tcc att ggg aag ccc tca ctg ttc atc tcc gtc tca gaa aag agc      1902
Gln Ser Ile Gly Lys Pro Ser Leu Phe Ile Ser Val Ser Glu Lys Ser
565                 570                 575                 580 aag gat cgc ggc agc aac acg atc ggc gcc cgc ctg aac cga gta gaa      1950
Lys Asp Arg Gly Ser Asn Thr Ile Gly Ala Arg Leu Asn Arg Val Glu
                585                 590                 595 gac aag gtg acg cag ctg gac cag agg ctg gca ctc atc acc gac atg      1998
Asp Lys Val Thr Gln Leu Asp Gln Arg Leu Ala Leu Ile Thr Asp Met
        600                 605                 610 ctt cac cag ctg ctc tcc ttg cac ggt ggc agc acc ccc ggc agc ggc      2046
Leu His Gln Leu Leu Ser Leu His Gly Gly Ser Thr Pro Gly Ser Gly
    615                 620                 625 ggc ccc ccc aga gag ggc ggg gcc cac atc acc cag ccc tgc ggc agt      2094
Gly Pro Pro Arg Glu Gly Gly Ala His Ile Thr Gln Pro Cys Gly Ser
630                 635                 640
```

-continued

```
ggc ggc tcc gtc gac cct gag ctc ttc ctg ccc agc aac acc ctg ccc    2142
Gly Gly Ser Val Asp Pro Glu Leu Phe Leu Pro Ser Asn Thr Leu Pro
645                 650                 655                 660 acc tac gag cag ctg acc gtg ccc agg agg ggc ccc gat gag ggg tcc    2190
Thr Tyr Glu Gln Leu Thr Val Pro Arg Arg Gly Pro Asp Glu Gly Ser
                665                 670                 675 tgaggagggg atgggctgg gggatgggcc tgagtgagag gggaggccaa gagtggcccc    2250
acctggccct ctctgaagga ggccacctcc taaaaggccc agagagaaga gccccactct    2310
cagaggcccc aataccccat ggaccatgct gtctggcaca gcctgcactt ggggctcag    2370 caaggccacc tcttcctggc cggtgtgggg gccccgtctc aggtctgagt tgttacccca    2430
agcgccctgg cccccacatg gtgatgttga catcactggc atggtggttg ggacccagtg    2490
gcagggcaca gggcctggcc catgtatggc caggaagtag cacaggctga gtgcaggccc    2550
accctgcttg gccaggggg cttcctgagg ggagacagag caacccctgg accccagcct    2610
caaatccagg accctgccag gcacaggcag ggcaggacca gcccacgctg actacagggc    2670
caccggcaat aaaagcccag gagcccattt ggagggcctg ggcctggctc cctcactctc    2730
aggaaatgct gacccatggg caggagactg tggagactgc tcctgagccc ccagcttcca    2790
gcaggaggga cagtctcacc atttccccag ggcacgtggt tgagtggggg gaacgcccac    2850
ttccctgggt tagactgcca gctcttccta gctggagagg agccctgcct ctccgcccct    2910
gagcccactg tgcgtggggc tcccgcctcc aaccctcgc ccagtcccag cagccagcca    2970
aacacacaga aggggactgc cacctcccct tgccagctgc tgagccgcag agaagtgacg    3030
gttcctacac aggacagggg ttccttctgg gcattacatc gcatagaaat caataatttg    3090
tggtgatttg gatctgtgtt ttaatgagtt tcacagtgtg attttgatta ttaattgtgc    3150
aagcttttcc taataaacgt ggagaatcac a                                  3181
```

<210> SEQ ID NO 2
<211> LENGTH: 676
<212> TYPE: PRT
<213> ORGANISM: Homo sapiens

<400> SEQUENCE: 2

```
Met Ala Ala Ser Ser Pro Pro Arg Ala Glu Arg Lys Arg Trp Gly
  1               5                  10                  15

Trp Gly Arg Leu Pro Gly Ala Arg Arg Gly Ser Ala Gly Leu Ala Lys
                 20                  25                  30

Lys Cys Pro Phe Ser Leu Glu Leu Ala Glu Gly Gly Pro Ala Gly Gly
             35                  40                  45

Ala Leu Tyr Ala Pro Ile Ala Pro Gly Ala Pro Gly Pro Ala Pro Pro
         50                  55                  60

Ala Ser Pro Ala Ala Pro Ala Ala Pro Pro Val Ala Ser Asp Leu Gly
 65                  70                  75                  80

Pro Arg Pro Pro Val Ser Leu Asp Pro Arg Val Ser Ile Tyr Ser Thr
                 85                  90                  95

Arg Arg Pro Val Leu Ala Arg Thr His Val Gln Gly Arg Val Tyr Asn
            100                 105                 110

Phe Leu Glu Arg Pro Thr Gly Trp Lys Cys Phe Val Tyr His Phe Ala
        115                 120                 125

Val Phe Leu Ile Val Leu Val Cys Leu Ile Phe Ser Val Leu Ser Thr
    130                 135                 140

Ile Glu Gln Tyr Ala Ala Leu Ala Thr Gly Thr Leu Phe Trp Met Glu
145                 150                 155                 160
```

-continued

```
Ile Val Leu Val Val Phe Phe Gly Thr Glu Tyr Val Arg Leu Trp
                165                 170                 175
Ser Ala Gly Cys Arg Ser Lys Tyr Val Gly Leu Trp Gly Arg Leu Arg
            180                 185                 190
Phe Ala Arg Lys Pro Ile Ser Ile Asp Leu Ile Val Val Val Ala
        195                 200                 205
Ser Met Val Val Leu Cys Val Gly Ser Lys Gly Gln Val Phe Ala Thr
    210                 215                 220
Ser Ala Ile Arg Gly Ile Arg Phe Leu Gln Ile Leu Arg Met Leu His
225                 230                 235                 240
Val Asp Arg Gln Gly Gly Thr Trp Arg Leu Leu Gly Ser Val Val Phe
                245                 250                 255
Ile His Arg Gln Glu Leu Ile Thr Thr Leu Tyr Ile Gly Phe Leu Gly
            260                 265                 270
Leu Ile Phe Ser Ser Tyr Phe Val Tyr Leu Ala Glu Lys Asp Ala Val
        275                 280                 285
Asn Glu Ser Gly Arg Val Glu Phe Gly Ser Tyr Ala Asp Ala Leu Trp
    290                 295                 300
Trp Gly Val Val Thr Val Thr Thr Ile Gly Tyr Gly Asp Lys Val Pro
305                 310                 315                 320
Gln Thr Trp Val Gly Lys Thr Ile Ala Ser Cys Phe Ser Val Phe Ala
                325                 330                 335
Ile Ser Phe Phe Ala Leu Pro Ala Gly Ile Leu Gly Ser Gly Phe Ala
            340                 345                 350
Leu Lys Val Gln Gln Lys Gln Arg Gln Lys His Phe Asn Arg Gln Ile
        355                 360                 365
Pro Ala Ala Ala Ser Leu Ile Gln Thr Ala Trp Arg Cys Tyr Ala Ala
    370                 375                 380
Glu Asn Pro Asp Ser Ser Thr Trp Lys Ile Tyr Ile Arg Lys Ala Pro
385                 390                 395                 400
Arg Ser His Thr Leu Leu Ser Pro Ser Pro Lys Pro Lys Lys Ser Val
                405                 410                 415
Val Val Lys Lys Lys Lys Phe Lys Leu Asp Lys Asp Asn Gly Val Thr
            420                 425                 430
Pro Gly Glu Lys Met Leu Thr Val Pro His Ile Thr Cys Asp Pro Pro
        435                 440                 445
Glu Glu Arg Arg Leu Asp His Phe Ser Val Asp Gly Tyr Asp Ser Ser
    450                 455                 460
Val Arg Lys Ser Pro Thr Leu Leu Glu Val Ser Met Pro His Phe Met
465                 470                 475                 480
Arg Thr Asn Ser Phe Ala Glu Asp Leu Asp Leu Glu Gly Glu Thr Leu
                485                 490                 495
Leu Thr Pro Ile Thr His Ile Ser Gln Leu Arg Glu His His Arg Ala
            500                 505                 510
Thr Ile Lys Val Ile Arg Arg Met Gln Tyr Phe Val Ala Lys Lys Lys
        515                 520                 525
Phe Gln Gln Ala Arg Lys Pro Tyr Asp Val Arg Asp Val Ile Glu Gln
    530                 535                 540
Tyr Ser Gln Gly His Leu Asn Leu Met Val Arg Ile Lys Glu Leu Gln
545                 550                 555                 560
Arg Arg Leu Asp Gln Ser Ile Gly Lys Pro Ser Leu Phe Ile Ser Val
                565                 570                 575
```

```
Ser Glu Lys Ser Lys Asp Arg Gly Ser Asn Thr Ile Gly Ala Arg Leu
        580                 585                 590

Asn Arg Val Glu Asp Lys Val Thr Gln Leu Asp Gln Arg Leu Ala Leu
        595                 600                 605

Ile Thr Asp Met Leu His Gln Leu Leu Ser Leu His Gly Gly Ser Thr
610                 615                 620

Pro Gly Ser Gly Gly Pro Pro Arg Glu Gly Gly Ala His Ile Thr Gln
625                 630                 635                 640

Pro Cys Gly Ser Gly Gly Ser Val Asp Pro Glu Leu Phe Leu Pro Ser
                645                 650                 655

Asn Thr Leu Pro Thr Tyr Glu Gln Leu Thr Val Pro Arg Arg Gly Pro
            660                 665                 670

Asp Glu Gly Ser
        675

<210> SEQ ID NO 3
<211> LENGTH: 63
<212> TYPE: DNA
<213> ORGANISM: Artificial Sequence
<220> FEATURE:
<223> OTHER INFORMATION: Description of Artificial Sequence:Hypothetical
      sequence to demonstrate calculation of percent
      homology or identity.

<400> SEQUENCE: 3
accgtagcta cgtacgtata tagaaagggc gcgatcgtcg tcgcgtatga cgacttagca        60
tgc                                                                     63

<210> SEQ ID NO 4
<211> LENGTH: 130
<212> TYPE: DNA
<213> ORGANISM: Artificial Sequence
<220> FEATURE:
<223> OTHER INFORMATION: Description of Artificial Sequence:Hypothetical
      sequence to demonstrate calculation of percent
      homology or identity.

<400> SEQUENCE: 4
accggtagct acgtacgtta tttagaaagg ggtgtgtgtg tgtgtgtaaa ccggggtttt        60
cgggatcgtc cgtcgcgtat gacgacttag ccatgcacgg tatatcgtat taggactagc      120
gattgactag                                                             130

<210> SEQ ID NO 5
<211> LENGTH: 3182
<212> TYPE: DNA
<213> ORGANISM: Homo sapiens
<220> FEATURE:
<221> NAME/KEY: CDS
<222> LOCATION: (163)..(1011)
<220> FEATURE:
<221> NAME/KEY: mutation
<222> LOCATION: (730)
<223> OTHER INFORMATION: This base is an insertion as compared to the
      wild-type.

<400> SEQUENCE: 5 ctgcccctc cggccccgcc ccgagcgccc gggctgggcc ggcagcggcc ccccgcggcg         60
gggctggcag cagtggctgc ccgcactgcg cccgggcgct cgccttcgct gcagctcccg      120
gtgccgccgc tcgggccggc ccccggcag gccctcctcg tt atg gcc gcg gcc         174
                                              Met Ala Ala Ala
                                                1
```

```
tcc tcc ccg ccc agg gcc gag agg aag cgc tgg ggt tgg ggc cgc ctg      222
Ser Ser Pro Pro Arg Ala Glu Arg Lys Arg Trp Gly Trp Gly Arg Leu
  5                  10                  15                  20 cca ggc gcc cgg cgg ggc agc gcg ggc ctg gcc aag aag tgc ccc ttc      270
Pro Gly Ala Arg Arg Gly Ser Ala Gly Leu Ala Lys Lys Cys Pro Phe
                     25                  30                  35 tcg ctg gag ctg gcg gag ggc ggc ccg gcg ggc ggc gcg ctc tac gcg      318
Ser Leu Glu Leu Ala Glu Gly Gly Pro Ala Gly Gly Ala Leu Tyr Ala
                 40                  45                  50 ccc atc gcg ccc ggc gcc cca ggt ccc gcg ccc cct gcg tcc ccg gcc      366
Pro Ile Ala Pro Gly Ala Pro Gly Pro Ala Pro Pro Ala Ser Pro Ala
             55                  60                  65 gcg ccc gcc gcg ccc cca gtt gcc tcc gac ctt ggc ccg cgg ccg ccg      414
Ala Pro Ala Ala Pro Pro Val Ala Ser Asp Leu Gly Pro Arg Pro Pro
         70                  75                  80 gtg agc cta gac ccg cgc gtc tcc atc tac agc acg cgc cgc ccg gtg      462
Val Ser Leu Asp Pro Arg Val Ser Ile Tyr Ser Thr Arg Arg Pro Val
 85                  90                  95                 100 ttg gcg cgc acc cac gtc cag ggc cgc gtc tac aac ttc ctc gag cgt      510
Leu Ala Arg Thr His Val Gln Gly Arg Val Tyr Asn Phe Leu Glu Arg
                    105                 110                 115 ccc acc ggc tgg aaa tgc ttc gtt tac cac ttc gcc gtc ttc ctc atc      558
Pro Thr Gly Trp Lys Cys Phe Val Tyr His Phe Ala Val Phe Leu Ile
                120                 125                 130 gtc ctg gtc tgc ctc atc ttc agc gtg ctg tcc acc atc gag cag tat      606
Val Leu Val Cys Leu Ile Phe Ser Val Leu Ser Thr Ile Glu Gln Tyr
            135                 140                 145 gcc gcc ctg gcc acg ggg act ctc ttc tgg atg gag atc gtg ctg gtg      654
Ala Ala Leu Ala Thr Gly Thr Leu Phe Trp Met Glu Ile Val Leu Val
        150                 155                 160 gtg ttc ttc ggg acg gag tac gtg gtc cgc ctc tgg tcc gcc ggc tgc      702
Val Phe Phe Gly Thr Glu Tyr Val Val Arg Leu Trp Ser Ala Gly Cys
165                 170                 175                 180 cgc agc aag tac gtg ggc ctc tgg ggg gcg gct gcg ctt tgc ccg gaa      750
Arg Ser Lys Tyr Val Gly Leu Trp Gly Ala Ala Ala Leu Cys Pro Glu
                    185                 190                 195 gcc cat ttc cat cat cga cct cat cgt ggt cgt ggc ctc cat ggt ggt      798
Ala His Phe His His Arg Pro His Arg Gly Arg Gly Leu His Gly Gly
                200                 205                 210 cct ctg cgt ggg ctc caa ggg gca ggt gtt tgc cac gtc ggc cat cag      846
Pro Leu Arg Gly Leu Gln Gly Ala Gly Val Cys His Val Gly His Gln
            215                 220                 225 ggg cat ccg ctt cct gca gat cct gag gat gct aca cgt cga ccg cca      894
Gly His Pro Leu Pro Ala Asp Pro Glu Asp Ala Thr Arg Arg Pro Pro
        230                 235                 240 ggg agg cac ctg gag gct cct ggg ctc cgt ggt ctt cat cca ccg cca      942
Gly Arg His Leu Glu Ala Pro Gly Leu Arg Gly Leu His Pro Pro Pro
245                 250                 255                 260 gga gct gat aac cac cct gta cat cgg ctt cct ggg cct cat ctt ctc      990
Gly Ala Asp Asn His Pro Val His Arg Leu Pro Gly Pro His Leu Leu
                    265                 270                 275 ctc gta ctt tgt gta cct ggc tgagaaggac gcggtgaacg agtcaggccg        1041
Leu Val Leu Cys Val Pro Gly
                280 cgtggagttc ggcagctacg cagatgcgct gtggtggggg gtggtcacag tcaccaccat   1101 cggctatggg gacaaggtgc cccagacgtg gtcgggaag accatcgcct cctgcttctc    1161 tgtctttgcc atctccttct ttgcgctccc agcggggatt cttggctcgg ggtttgccct   1221 gaaggtgcag cagaagcaga ggcagaagca cttcaaccgg cagatcccgg cggcagcctc   1281
```

-continued

```
actcattcag accgcatgga ggtgctatgc tgccgagaac cccgactcct ccacctggaa    1341
gatctacatc cggaaggccc cccggagcca cactctgctg tcacccagcc ccaaacccaa    1401
gaagtctgtg gtggtaaaga aaaaaaagtt caagctggac aaagacaatg gggtgactcc    1461
tggagagaag atgctcacag tcccccatat cacgtgcgac cccccagaag agcggcggct    1521
ggaccacttc tctgtcgacg gctatgacag ttctgtaagg aagagcccaa cactgctgga    1581
agtgagcatg ccccatttca tgagaaccaa cagcttcgcc gaggacctgg acctggaagg    1641
ggagactctg ctgacaccca tcacccacat ctcacagctg cgggaacacc atcgggccac    1701
cattaaggtc attcgacgca tgcagtactt tgtggccaag aagaaattcc agcaagcgcg    1761
gaagccttac gatgtgcggg acgtcattga gcagtactcg cagggccacc tcaacctcat    1821
ggtgcgcatc aaggagctgc agaggaggct ggaccagtcc attgggaagc cctcactgtt    1881
catctccgtc tcagaaaaga gcaaggatcg cggcagcaac acgatcggcg cccgcctgaa    1941
ccgagtagaa gacaaggtga cgcagctgga ccagaggctg gcactcatca ccgacatgct    2001
tcaccagctg ctctccttgc acggtggcag cacccccggc agcggcggcc ccccagaga    2061 gggcggggcc cacatcaccc agccctgcgg cagtggcggc tccgtcgacc ctgagctctt    2121
cctgcccagc aacaccctgc ccacctacga gcagctgacc gtgcccagga ggggcccga    2181 tgagggtcc tgaggagggg atgggctgg gggatgggcc tgagtgagag gggaggccaa    2241
gagtggcccc acctggccct ctctgaagga ggccacctcc taaaaggccc agagagaaga    2301
gccccactct cagaggcccc aatacccat ggaccatgct gtctggcaca gcctgcactt    2361
gggggctcag caaggccacc tcttcctggc cggtgtgggg gccccgtctc aggtctgagt    2421
tgttacccca agcgccctgg ccccacatg gtgatgttga catcactggc atggtggttg    2481
ggacccagtg gcagggcaca gggcctggcc catgtatggc caggaagtag cacaggctga    2541
gtgcaggccc accctgcttg gcccagggg cttcctgagg ggagacagag caaccctgg    2601 accccagcct caaatccagg accctgccag gcacaggcag gcaggacca gcccacgctg    2661 actacagggc caccggcaat aaaagcccag gagcccattt ggagggcctg gcctggctc    2721 cctcactctc aggaaatgct gacccatggg caggagactg tggagactgc tcctgagccc    2781
ccagcttcca gcaggaggga cagtctcacc atttccccag ggcacgtggt tgagtggggg    2841
gaacgcccac ttccctgggt tagactgcca gctcttccta gctggagagg agccctgcct    2901
ctccgcccct gagcccactg tgcgtggggc tcccgcctcc aacccctcgc ccagtcccag    2961
cagccagcca aacacacaga aggggactgc cacctcccct tgccagctgc tgagccgcag    3021
agaagtgacg gttcctacac aggacagggg ttccttctgg gcattacatc gcatagaaat    3081
caataatttg tggtgatttg gatctgtgtt ttaatgagtt tcacagtgtg attttgatta    3141
ttaattgtgc aagcttttcc taataaacgt ggagaatcac a    3182
```

<210> SEQ ID NO 6
<211> LENGTH: 283
<212> TYPE: PRT
<213> ORGANISM: Homo sapiens

<400> SEQUENCE: 6

Met Ala Ala Ser Ser Pro Pro Arg Ala Glu Arg Lys Arg Trp Gly
 1               5                  10                  15

Trp Gly Arg Leu Pro Gly Ala Arg Arg Gly Ser Ala Gly Leu Ala Lys
            20                  25                  30

-continued

```
Lys Cys Pro Phe Ser Leu Glu Leu Ala Glu Gly Gly Pro Ala Gly Gly
         35                  40                  45

Ala Leu Tyr Ala Pro Ile Ala Pro Gly Ala Pro Gly Pro Ala Pro Pro
     50                  55                  60

Ala Ser Pro Ala Ala Pro Ala Ala Pro Pro Val Ala Ser Asp Leu Gly
 65                  70                  75                  80

Pro Arg Pro Pro Val Ser Leu Asp Pro Arg Val Ser Ile Tyr Ser Thr
                 85                  90                  95

Arg Arg Pro Val Leu Ala Arg Thr His Val Gln Gly Arg Val Tyr Asn
            100                 105                 110

Phe Leu Glu Arg Pro Thr Gly Trp Lys Cys Phe Val Tyr His Phe Ala
        115                 120                 125

Val Phe Leu Ile Val Leu Val Cys Leu Ile Phe Ser Val Leu Ser Thr
    130                 135                 140

Ile Glu Gln Tyr Ala Ala Leu Ala Thr Gly Thr Leu Phe Trp Met Glu
145                 150                 155                 160

Ile Val Leu Val Val Phe Phe Gly Thr Glu Tyr Val Val Arg Leu Trp
                165                 170                 175

Ser Ala Gly Cys Arg Ser Lys Tyr Val Gly Leu Trp Gly Ala Ala Ala
            180                 185                 190

Leu Cys Pro Glu Ala His Phe His His Arg Pro His Arg Gly Arg Gly
        195                 200                 205

Leu His Gly Gly Pro Leu Arg Gly Leu Gln Gly Ala Gly Val Cys His
    210                 215                 220

Val Gly His Gln Gly His Pro Leu Pro Ala Asp Pro Glu Asp Ala Thr
225                 230                 235                 240

Arg Arg Pro Pro Gly Arg His Leu Glu Ala Pro Gly Leu Arg Gly Leu
                245                 250                 255

His Pro Pro Pro Gly Ala Asp Asn His Pro Val His Arg Leu Pro Gly
            260                 265                 270

Pro His Leu Leu Leu Val Leu Cys Val Pro Gly
        275                 280

<210> SEQ ID NO 7
<211> LENGTH: 10
<212> TYPE: DNA
<213> ORGANISM: Homo sapiens

<400> SEQUENCE: 7
atggccgcgg                                                          10

<210> SEQ ID NO 8
<211> LENGTH: 20
<212> TYPE: DNA
<213> ORGANISM: Homo sapiens

<400> SEQUENCE: 8
acttcgccgt gtgagtatcg                                               20

<210> SEQ ID NO 9
<211> LENGTH: 20
<212> TYPE: DNA
<213> ORGANISM: Homo sapiens

<400> SEQUENCE: 9
tgtcttgcag cttcctcatc                                               20
```

```
<210> SEQ ID NO 10
<211> LENGTH: 20
<212> TYPE: DNA
<213> ORGANISM: Homo sapiens

<400> SEQUENCE: 10
cttctggatg gtacgtagca                                              20

<210> SEQ ID NO 11
<211> LENGTH: 20
<212> TYPE: DNA
<213> ORGANISM: Homo sapiens

<400> SEQUENCE: 11
gtccctgcag gagatcgtgc                                              20

<210> SEQ ID NO 12
<211> LENGTH: 20
<212> TYPE: DNA
<213> ORGANISM: Homo sapiens

<400> SEQUENCE: 12
tccatcatcg gtgagtcatg                                              20

<210> SEQ ID NO 13
<211> LENGTH: 20
<212> TYPE: DNA
<213> ORGANISM: Homo sapiens

<400> SEQUENCE: 13
cactccacag acctcatcgt                                              20

<210> SEQ ID NO 14
<211> LENGTH: 20
<212> TYPE: DNA
<213> ORGANISM: Homo sapiens

<400> SEQUENCE: 14
gggccatcag gtgcgtctgt                                              20

<210> SEQ ID NO 15
<211> LENGTH: 20
<212> TYPE: DNA
<213> ORGANISM: Homo sapiens

<400> SEQUENCE: 15
tccttcgcag gggcatccgc                                              20

<210> SEQ ID NO 16
<211> LENGTH: 20
<212> TYPE: DNA
<213> ORGANISM: Homo sapiens

<400> SEQUENCE: 16
ccaccgccag gtgggtggcc                                              20

<210> SEQ ID NO 17
<211> LENGTH: 20
<212> TYPE: DNA
<213> ORGANISM: Homo sapiens

<400> SEQUENCE: 17
tctggcctag gagctgataa                                              20
```

<210> SEQ ID NO 18
<211> LENGTH: 20
<212> TYPE: DNA
<213> ORGANISM: Homo sapiens

<400> SEQUENCE: 18 gtgggggtg gtaagtcgga                                       20

<210> SEQ ID NO 19
<211> LENGTH: 20
<212> TYPE: DNA
<213> ORGANISM: Homo sapiens

<400> SEQUENCE: 19
ctccctgcag gtcacagtca                                      20

<210> SEQ ID NO 20
<211> LENGTH: 20
<212> TYPE: DNA
<213> ORGANISM: Homo sapiens

<400> SEQUENCE: 20
gctcccagcg gtaggtgccc                                      20

<210> SEQ ID NO 21
<211> LENGTH: 20
<212> TYPE: DNA
<213> ORGANISM: Homo sapiens

<400> SEQUENCE: 21
tccttcccag gggattcttg                                      20

<210> SEQ ID NO 22
<211> LENGTH: 20
<212> TYPE: DNA
<213> ORGANISM: Homo sapiens

<400> SEQUENCE: 22
actcattcag gtgcggtgcc                                      20

<210> SEQ ID NO 23
<211> LENGTH: 20
<212> TYPE: DNA
<213> ORGANISM: Homo sapiens

<400> SEQUENCE: 23
cccacctcag accgcatgga                                      20

<210> SEQ ID NO 24
<211> LENGTH: 20
<212> TYPE: DNA
<213> ORGANISM: Homo sapiens

<400> SEQUENCE: 24
gtctgtggtg gtgagtagcc                                      20

<210> SEQ ID NO 25
<211> LENGTH: 20
<212> TYPE: DNA
<213> ORGANISM: Homo sapiens

<400> SEQUENCE: 25
ttttttttag gtaaagaaaa                                      20

```
<210> SEQ ID NO 26
<211> LENGTH: 20
<212> TYPE: DNA
<213> ORGANISM: Homo sapiens

<400> SEQUENCE: 26
gacagttctg gtgagaaccc                                              20

<210> SEQ ID NO 27
<211> LENGTH: 20
<212> TYPE: DNA
<213> ORGANISM: Homo sapiens

<400> SEQUENCE: 27
ttctcctcag taaggaagag                                              20

<210> SEQ ID NO 28
<211> LENGTH: 20
<212> TYPE: DNA
<213> ORGANISM: Homo sapiens

<400> SEQUENCE: 28
acatctcaca gtgagtgcct                                              20

<210> SEQ ID NO 29
<211> LENGTH: 20
<212> TYPE: DNA
<213> ORGANISM: Homo sapiens

<400> SEQUENCE: 29
tccactgcag gctgcgggaa                                              20

<210> SEQ ID NO 30
<211> LENGTH: 20
<212> TYPE: DNA
<213> ORGANISM: Homo sapiens

<400> SEQUENCE: 30
gaaattccag gtaagccctg                                              20

<210> SEQ ID NO 31
<211> LENGTH: 20
<212> TYPE: DNA
<213> ORGANISM: Homo sapiens

<400> SEQUENCE: 31
tgtcccgcag caagcgcgga                                              20

<210> SEQ ID NO 32
<211> LENGTH: 20
<212> TYPE: DNA
<213> ORGANISM: Homo sapiens

<400> SEQUENCE: 32
tgcagaggag gtgggcacgg                                              20

<210> SEQ ID NO 33
<211> LENGTH: 20
<212> TYPE: DNA
<213> ORGANISM: Homo sapiens

<400> SEQUENCE: 33
```

-continued ttctctccag gctggaccag                                              20

<210> SEQ ID NO 34
<211> LENGTH: 20
<212> TYPE: DNA
<213> ORGANISM: Homo sapiens

<400> SEQUENCE: 34
tccgtctcag gtgggtttct                                              20

<210> SEQ ID NO 35
<211> LENGTH: 20
<212> TYPE: DNA
<213> ORGANISM: Homo sapiens

<400> SEQUENCE: 35
tcccccatag aaaagagcaa                                              20

<210> SEQ ID NO 36
<211> LENGTH: 20
<212> TYPE: DNA
<213> ORGANISM: Homo sapiens

<400> SEQUENCE: 36
agaagacaag gtaggctcac                                              20

<210> SEQ ID NO 37
<211> LENGTH: 20
<212> TYPE: DNA
<213> ORGANISM: Homo sapiens

<400> SEQUENCE: 37
gtccccgcag gtgacgcagc                                              20

<210> SEQ ID NO 38
<211> LENGTH: 10
<212> TYPE: DNA
<213> ORGANISM: Homo sapiens

<400> SEQUENCE: 38
ggggtcctga                                                         10

<210> SEQ ID NO 39
<211> LENGTH: 19
<212> TYPE: DNA
<213> ORGANISM: Homo sapiens

<400> SEQUENCE: 39
ctcgccttcg ctgcagctc                                               19

<210> SEQ ID NO 40
<211> LENGTH: 19
<212> TYPE: DNA
<213> ORGANISM: Homo sapiens

<400> SEQUENCE: 40
gcgcgggtct aggctcacc                                               19

<210> SEQ ID NO 41
<211> LENGTH: 18
<212> TYPE: DNA
<213> ORGANISM: Homo sapiens

<400> SEQUENCE: 41
cgccgcgccc ccagttgc                                              18

<210> SEQ ID NO 42
<211> LENGTH: 19
<212> TYPE: DNA
<213> ORGANISM: Homo sapiens

<400> SEQUENCE: 42
cagagctccc ccacaccag                                             19

<210> SEQ ID NO 43
<211> LENGTH: 24
<212> TYPE: DNA
<213> ORGANISM: Homo sapiens

<400> SEQUENCE: 43
atgggcagag gccgtgatgc tgac                                       24

<210> SEQ ID NO 44
<211> LENGTH: 22
<212> TYPE: DNA
<213> ORGANISM: Homo sapiens

<400> SEQUENCE: 44
atccagccat gccctcagat gc                                         22

<210> SEQ ID NO 45
<211> LENGTH: 24
<212> TYPE: DNA
<213> ORGANISM: Homo sapiens

<400> SEQUENCE: 45
gttcaaacag gttgcagggt ctga                                       24

<210> SEQ ID NO 46
<211> LENGTH: 21
<212> TYPE: DNA
<213> ORGANISM: Homo sapiens

<400> SEQUENCE: 46
cttcctggtc tggaaacctg g                                          21

<210> SEQ ID NO 47
<211> LENGTH: 20
<212> TYPE: DNA
<213> ORGANISM: Homo sapiens

<400> SEQUENCE: 47
ctcttccctg gggccctggc                                            20

<210> SEQ ID NO 48
<211> LENGTH: 22
<212> TYPE: DNA
<213> ORGANISM: Homo sapiens

<400> SEQUENCE: 48
tgcgggggag cttgtggcac ag                                         22

<210> SEQ ID NO 49
<211> LENGTH: 22
<212> TYPE: DNA
<213> ORGANISM: Homo sapiens

```
<400> SEQUENCE: 49
tcagccccac accatctcct tc                                              22

<210> SEQ ID NO 50
<211> LENGTH: 20
<212> TYPE: DNA
<213> ORGANISM: Homo sapiens

<400> SEQUENCE: 50
ctgggcccct accctaaccc                                                 20

<210> SEQ ID NO 51
<211> LENGTH: 23
<212> TYPE: DNA
<213> ORGANISM: Homo sapiens

<400> SEQUENCE: 51
tcctggagcc cgacactgtg tgt                                             23

<210> SEQ ID NO 52
<211> LENGTH: 22
<212> TYPE: DNA
<213> ORGANISM: Homo sapiens

<400> SEQUENCE: 52
tgtcctgccc actcctcagc ct                                              22

<210> SEQ ID NO 53
<211> LENGTH: 20
<212> TYPE: DNA
<213> ORGANISM: Homo sapiens

<400> SEQUENCE: 53
tggctgacca ctgtccctct                                                 20

<210> SEQ ID NO 54
<211> LENGTH: 22
<212> TYPE: DNA
<213> ORGANISM: Homo sapiens

<400> SEQUENCE: 54
ccccaggacc ccagctgtcc aa                                              22

<210> SEQ ID NO 55
<211> LENGTH: 21
<212> TYPE: DNA
<213> ORGANISM: Homo sapiens

<400> SEQUENCE: 55
gctggcagtg gcctgtgtgg a                                               21

<210> SEQ ID NO 56
<211> LENGTH: 24
<212> TYPE: DNA
<213> ORGANISM: Homo sapiens

<400> SEQUENCE: 56
aacagtgacc aaaatgacag tgac                                            24

<210> SEQ ID NO 57
<211> LENGTH: 19
<212> TYPE: DNA
<213> ORGANISM: Homo sapiens
```

```
<400> SEQUENCE: 57
tggctcagca ggtgacagc                                                19

<210> SEQ ID NO 58
<211> LENGTH: 19
<212> TYPE: DNA
<213> ORGANISM: Homo sapiens

<400> SEQUENCE: 58
tggtggcagg tgggctact                                                19

<210> SEQ ID NO 59
<211> LENGTH: 19
<212> TYPE: DNA
<213> ORGANISM: Homo sapiens

<400> SEQUENCE: 59
gcctggcaga cgatgtcca                                                19

<210> SEQ ID NO 60
<211> LENGTH: 19
<212> TYPE: DNA
<213> ORGANISM: Homo sapiens

<400> SEQUENCE: 60
caactgcctg agggttct                                                 19

<210> SEQ ID NO 61
<211> LENGTH: 20
<212> TYPE: DNA
<213> ORGANISM: Homo sapiens

<400> SEQUENCE: 61
ctgtccccac actttctcct                                               20

<210> SEQ ID NO 62
<211> LENGTH: 20
<212> TYPE: DNA
<213> ORGANISM: Homo sapiens

<400> SEQUENCE: 62
tgagctccag tcccctccag                                               20

<210> SEQ ID NO 63
<211> LENGTH: 19
<212> TYPE: DNA
<213> ORGANISM: Homo sapiens

<400> SEQUENCE: 63
tggccactca caatctcct                                                19

<210> SEQ ID NO 64
<211> LENGTH: 19
<212> TYPE: DNA
<213> ORGANISM: Homo sapiens

<400> SEQUENCE: 64
gccttgacac cctccacta                                                19

<210> SEQ ID NO 65
<211> LENGTH: 19
<212> TYPE: DNA
```

<213> ORGANISM: Homo sapiens

<400> SEQUENCE: 65
ggcacaggga ggagaagtg   19

<210> SEQ ID NO 66
<211> LENGTH: 19
<212> TYPE: DNA
<213> ORGANISM: Homo sapiens

<400> SEQUENCE: 66
cggcaccgct gatcatgca   19

<210> SEQ ID NO 67
<211> LENGTH: 19
<212> TYPE: DNA
<213> ORGANISM: Homo sapiens

<400> SEQUENCE: 67
ccagggccag gtgtgactg   19

<210> SEQ ID NO 68
<211> LENGTH: 20
<212> TYPE: DNA
<213> ORGANISM: Homo sapiens

<400> SEQUENCE: 68
tgggcccaga gtaactgaca   20

<210> SEQ ID NO 69
<211> LENGTH: 21
<212> TYPE: DNA
<213> ORGANISM: Homo sapiens

<400> SEQUENCE: 69
ggccctgatt tgggtgtttt a   21

<210> SEQ ID NO 70
<211> LENGTH: 19
<212> TYPE: DNA
<213> ORGANISM: Homo sapiens

<400> SEQUENCE: 70
ggacgctaac cagaaccac   19

<210> SEQ ID NO 71
<211> LENGTH: 20
<212> TYPE: DNA
<213> ORGANISM: Homo sapiens

<400> SEQUENCE: 71
caccactgac tctctcgtct   20

<210> SEQ ID NO 72
<211> LENGTH: 18
<212> TYPE: DNA
<213> ORGANISM: Homo sapiens

<400> SEQUENCE: 72
ccatccccca gccccatc   18

<210> SEQ ID NO 73
<211> LENGTH: 18

-continued

```
<212> TYPE: DNA
<213> ORGANISM: Homo sapiens
<220> FEATURE:
<221> NAME/KEY: CDS
<222> LOCATION: (1)..(18)

<400> SEQUENCE: 73 ctc tgg ggg cgg ctg cgc                                              18
Leu Trp Gly Arg Leu Arg
 1               5

<210> SEQ ID NO 74
<211> LENGTH: 6
<212> TYPE: PRT
<213> ORGANISM: Homo sapiens

<400> SEQUENCE: 74

Leu Trp Gly Arg Leu Arg
 1               5

<210> SEQ ID NO 75
<211> LENGTH: 18
<212> TYPE: DNA
<213> ORGANISM: Homo sapiens
<220> FEATURE:
<221> NAME/KEY: CDS
<222> LOCATION: (1)..(18)

<400> SEQUENCE: 75 ctc tgg ggg gcg gct gcg                                              18
Leu Trp Gly Ala Ala Ala
 1               5

<210> SEQ ID NO 76
<211> LENGTH: 6
<212> TYPE: PRT
<213> ORGANISM: Homo sapiens

<400> SEQUENCE: 76

Leu Trp Gly Ala Ala Ala
 1               5

<210> SEQ ID NO 77
<211> LENGTH: 1703
<212> TYPE: DNA
<213> ORGANISM: Homo sapiens
<220> FEATURE:
<221> NAME/KEY: CDS
<222> LOCATION: (193)..(579)

<400> SEQUENCE: 77
acacccggct ctctcggcat ctcagacccg ggaaaaatcc ctctgctttc tctggccagt     60
ttcacacaat catcaggtga gccgaggatc cattggagga aggcattatc tgtatccaga    120
ggaaatagcc aaggatattc agaggtgtgc ctgggaagtt tgagctgcag cagtggaacc    180
ttaatgccca gg atg atc ctg tct aac acc aca gcg gtg acg ccc ttt ctg    231
             Met Ile Leu Ser Asn Thr Thr Ala Val Thr Pro Phe Leu
              1               5                  10 acc aag ctg tgg cag gag aca gtt cag cag ggt ggc aac atg tcg ggc      279
Thr Lys Leu Trp Gln Glu Thr Val Gln Gln Gly Gly Asn Met Ser Gly
 15              20                  25 ctg gcc cgc agg tcc ccc cgc agc ggt gac ggc aag ctg gag gcc ctc      327
Leu Ala Arg Arg Ser Pro Arg Ser Gly Asp Gly Lys Leu Glu Ala Leu
 30              35                  40                  45 tac gtc ctc atg gta ctg gga ttc ttc ggc ttc ttc acc ctg ggc atc      375
```

-continued

```
                Tyr Val Leu Met Val Leu Gly Phe Phe Gly Phe Phe Thr Leu Gly Ile
                            50                  55                  60 atg ctg agc tac atc cgc tcc aag aag ctg gag cac tcg aac gac cca           423
Met Leu Ser Tyr Ile Arg Ser Lys Lys Leu Glu His Ser Asn Asp Pro
             65                  70                  75 ttc aac gtc tac atc gag tcc gat gcc tgg caa gag aag gac aag gcc           471
Phe Asn Val Tyr Ile Glu Ser Asp Ala Trp Gln Glu Lys Asp Lys Ala
         80                  85                  90 tat gtc cag gcc cgg gtc ctg gag agc tac agg tcg tgc tat gtc gtt           519
Tyr Val Gln Ala Arg Val Leu Glu Ser Tyr Arg Ser Cys Tyr Val Val
     95                 100                 105 gaa aac cat ctg gcc ata gaa caa ccc aac aca cac ctt cct gag acg           567
Glu Asn His Leu Ala Ile Glu Gln Pro Asn Thr His Leu Pro Glu Thr
110                 115                 120                 125 aag cct tcc cca tgaaccccac cactggctaa actggacacc tcctgctggn              619
Lys Pro Ser Pro nnnnagattt tctaatcaca ttcctctcat actctttatt gtgatggata ccactggatt         679 tcttttggc tgttgtaang ggtgaggggt ggattaatga cactgtttca ctgtttctct          739
aaaatcacgt tcttttgtga tagactgtca gtggttcccc catatctgtc cctgccttgc         799
taaatttagc agaatccctg aggacatggc ctctgagaat agcagctgca tttcccagac         859
tcccttgcag ctagcaaggt tgtgtgacta agccctggcc agtaggcatg gaagtgaaga         919
ctgtaatgtc caagtaatcc ttggaaagaa aagaacgtgc ccttaactaa ctttgtcctg         979
cttcccagtg gctggatgtg gaggaggtgg agagcagtta tgagactggg aaagttcggg        1039
gcactcaaag agccacacac atctgggcct gggcgacgtg gatcctcctt accacccacc        1099
aggccagatt tacaggagag agaaatccac tccactcttc cttaagccac tgttattctg        1159
atctctgtta aggtcgcaga atcaatgccc ttactgatac acctaccta taggactgaa         1219 cctaaaggca tgacatttcc atacttgtca caagcacaca ctgattctgc ccttgtcact        1279
tctgtgctca ctcttgtggc tctatcctcc tcctgcccct ccgccttcca ctcctcccctt       1339 gcacccatcc tgcacacatc tccctgaaaa cacacaggca catacactca tatacataga        1399
cacacataca cacctcaatc tagaaagaac ttgctttgta cagggctgag atggaggaga        1459
aaaaaatgcc cccttcagaa tgcataccaa ggggaaggtg ctcggtcact gtgggagcag        1519
ggaaaggtgc ccccactccc cgagagccag gggaaggagt ggctctgggc agagagggac       1579
acatagcact ggggtggcag gtccttttga ggtgatgggc cggttttgtg agatgaattg        1639
tatcccccaa aaagacaggt accttcaatg tgacctaatt gggaaataga gtctttgcag        1699
atga                                                                     1703
```

<210> SEQ ID NO 78
<211> LENGTH: 129
<212> TYPE: PRT
<213> ORGANISM: Homo sapiens

<400> SEQUENCE: 78

```
Met Ile Leu Ser Asn Thr Thr Ala Val Thr Pro Phe Leu Thr Lys Leu
 1               5                  10                  15

Trp Gln Glu Thr Val Gln Gln Gly Gly Asn Met Ser Gly Leu Ala Arg
            20                  25                  30

Arg Ser Pro Arg Ser Gly Asp Gly Lys Leu Glu Ala Leu Tyr Val Leu
        35                  40                  45

Met Val Leu Gly Phe Phe Gly Phe Phe Thr Leu Gly Ile Met Leu Ser
    50                  55                  60
```

```
Tyr Ile Arg Ser Lys Lys Leu Glu His Ser Asn Asp Pro Phe Asn Val
 65                  70                  75                  80

Tyr Ile Glu Ser Asp Ala Trp Gln Glu Lys Asp Lys Ala Tyr Val Gln
                 85                  90                  95

Ala Arg Val Leu Glu Ser Tyr Arg Ser Cys Tyr Val Val Glu Asn His
            100                 105                 110

Leu Ala Ile Glu Gln Pro Asn Thr His Leu Pro Glu Thr Lys Pro Ser
        115                 120                 125

Pro

<210> SEQ ID NO 79
<211> LENGTH: 2734
<212> TYPE: DNA
<213> ORGANISM: Homo sapiens
<220> FEATURE:
<221> NAME/KEY: CDS
<222> LOCATION: (1)..(1743)

<400> SEQUENCE: 79 atg gag acg cgc ggg tct agg ctc acc ggc ggc cag ggc cgc gtc tac      48
Met Glu Thr Arg Gly Ser Arg Leu Thr Gly Gly Gln Gly Arg Val Tyr
  1               5                  10                  15 aac ttc ctc gag cgt ccc acc ggc tgg aaa tgc ttc gtt tac cac ttc      96
Asn Phe Leu Glu Arg Pro Thr Gly Trp Lys Cys Phe Val Tyr His Phe
             20                  25                  30 gcc gtc ttc ctc atc gtc ctg gtc tgc ctc atc ttc agc gtg ctg tcc     144
Ala Val Phe Leu Ile Val Leu Val Cys Leu Ile Phe Ser Val Leu Ser
         35                  40                  45 acc atc gag cag tat gcc gcc ctg gcc acg ggg act ctc ttc tgg atg     192
Thr Ile Glu Gln Tyr Ala Ala Leu Ala Thr Gly Thr Leu Phe Trp Met
     50                  55                  60 gag atc gtg ctg gtg gtg ttc ttc ggg acg gag tac gtg gtc cgc ctc     240
Glu Ile Val Leu Val Val Phe Phe Gly Thr Glu Tyr Val Val Arg Leu
 65                  70                  75                  80 tgg tcc gcc ggc tgc cgc agc aag tac gtg ggc ctc tgg ggg cgg ctg     288
Trp Ser Ala Gly Cys Arg Ser Lys Tyr Val Gly Leu Trp Gly Arg Leu
                 85                  90                  95 cgc ttt gcc cgg aag ccc att tcc atc atc gac ctc atc gtg gtc gtg     336
Arg Phe Ala Arg Lys Pro Ile Ser Ile Ile Asp Leu Ile Val Val Val
            100                 105                 110 gcc tcc atg gtg gtc ctc tgc gtg ggc tcc aag ggg cag gtg ttt gcc     384
Ala Ser Met Val Val Leu Cys Val Gly Ser Lys Gly Gln Val Phe Ala
        115                 120                 125 acg tcg gcc atc agg ggc atc cgc ttc ctg cag atc ctg agg atg cta     432
Thr Ser Ala Ile Arg Gly Ile Arg Phe Leu Gln Ile Leu Arg Met Leu
    130                 135                 140 cac gtc gac cgc cag gga ggc acc tgg agg ctc ctg ggc tcc gtg gtc     480
His Val Asp Arg Gln Gly Gly Thr Trp Arg Leu Leu Gly Ser Val Val
145                 150                 155                 160 ttc atc cac cgc cag gag ctg ata acc acc ctg tac atc ggc ttc ctg     528
Phe Ile His Arg Gln Glu Leu Ile Thr Thr Leu Tyr Ile Gly Phe Leu
                165                 170                 175 ggc ctc atc ttc tcc tcg tac ttt gtg tac ctg gct gag aag gac gcg     576
Gly Leu Ile Phe Ser Ser Tyr Phe Val Tyr Leu Ala Glu Lys Asp Ala
            180                 185                 190 gtg aac gag tca ggc cgc gtg gag ttc ggc agc tac gca gat gcg ctg     624
Val Asn Glu Ser Gly Arg Val Glu Phe Gly Ser Tyr Ala Asp Ala Leu
        195                 200                 205 tgg tgg ggg gtg gtc aca gtc acc acc atc ggc tat ggg gac aag gtg     672
```

-continued

```
Trp Trp Gly Val Val Thr Val Thr Thr Ile Gly Tyr Gly Asp Lys Val
    210                 215                 220 ccc cag acg tgg gtc ggg aag acc atc gcc tcc tgc ttc tct gtc ttt        720
Pro Gln Thr Trp Val Gly Lys Thr Ile Ala Ser Cys Phe Ser Val Phe
225                 230                 235                 240 gcc atc tcc ttc ttt gcg ctc cca gcg ggg att ctt ggc tcg ggg ttt        768
Ala Ile Ser Phe Phe Ala Leu Pro Ala Gly Ile Leu Gly Ser Gly Phe
                245                 250                 255 gcc ctg aag gtg cag cag aag cag agg cag aag cac ttc aac cgg cag        816
Ala Leu Lys Val Gln Gln Lys Gln Arg Gln Lys His Phe Asn Arg Gln
            260                 265                 270 atc ccg gcg gca gcc tca ctc att cag acc gca tgg agg tgc tat gct        864
Ile Pro Ala Ala Ala Ser Leu Ile Gln Thr Ala Trp Arg Cys Tyr Ala
        275                 280                 285 gcc gag aac ccc gac tcc tcc acc tgg aag atc tac atc cgg aag gcc        912
Ala Glu Asn Pro Asp Ser Ser Thr Trp Lys Ile Tyr Ile Arg Lys Ala
    290                 295                 300 ccc cgg agc cac act ctg ctg tca ccc agc ccc aaa ccc aag aag tct        960
Pro Arg Ser His Thr Leu Leu Ser Pro Ser Pro Lys Pro Lys Lys Ser
305                 310                 315                 320 gtg gtg gta aag aaa aaa aag ttc aag ctg gac aaa gac aat ggg gtg       1008
Val Val Val Lys Lys Lys Lys Phe Lys Leu Asp Lys Asp Asn Gly Val
                325                 330                 335 act cct gga gag aag atg ctc aca gtc ccc cat atc acg tgc gac ccc       1056
Thr Pro Gly Glu Lys Met Leu Thr Val Pro His Ile Thr Cys Asp Pro
            340                 345                 350 cca gaa gag cgg cgg ctg gac cac ttc tct gtc gac ggc tat gac agt       1104
Pro Glu Glu Arg Arg Leu Asp His Phe Ser Val Asp Gly Tyr Asp Ser
        355                 360                 365 tct gta agg aag agc cca aca ctg ctg gaa gtg agc atg ccc cat ttc       1152
Ser Val Arg Lys Ser Pro Thr Leu Leu Glu Val Ser Met Pro His Phe
    370                 375                 380 atg aga acc aac agc ttc gcc gag gac ctg gac ctg gaa ggg gag act       1200
Met Arg Thr Asn Ser Phe Ala Glu Asp Leu Asp Leu Glu Gly Glu Thr
385                 390                 395                 400 ctg ctg aca ccc atc acc cac atc tca cag ctg cgg gaa cac cat cgg       1248
Leu Leu Thr Pro Ile Thr His Ile Ser Gln Leu Arg Glu His His Arg
                405                 410                 415 gcc acc att aag gtc att cga cgc atg cag tac ttt gtg gcc aag aag       1296
Ala Thr Ile Lys Val Ile Arg Arg Met Gln Tyr Phe Val Ala Lys Lys
            420                 425                 430 aaa ttc cag caa gcg cgg aag cct tac gat gtg cgg gac gtc att gag       1344
Lys Phe Gln Gln Ala Arg Lys Pro Tyr Asp Val Arg Asp Val Ile Glu
        435                 440                 445 cag tac tcg cag ggc cac ctc aac ctc atg gtg cgc atc aag gag ctg       1392
Gln Tyr Ser Gln Gly His Leu Asn Leu Met Val Arg Ile Lys Glu Leu
    450                 455                 460 cag agg agg ctg gac cag tcc att ggg aag ccc tca ctg ttc atc tcc       1440
Gln Arg Arg Leu Asp Gln Ser Ile Gly Lys Pro Ser Leu Phe Ile Ser
465                 470                 475                 480 gtc tca gaa aag agc aag gat cgc ggc agc aac acg atc ggc gcc cgc       1488
Val Ser Glu Lys Ser Lys Asp Arg Gly Ser Asn Thr Ile Gly Ala Arg
                485                 490                 495 ctg aac cga gta gaa gac aag gtg acg cag ctg gac cag agg ctg gca       1536
Leu Asn Arg Val Glu Asp Lys Val Thr Gln Leu Asp Gln Arg Leu Ala
            500                 505                 510 ctc atc acc gac atg ctt cac cag ctg ctc tcc ttg cac ggt ggc agc       1584
Leu Ile Thr Asp Met Leu His Gln Leu Leu Ser Leu His Gly Gly Ser
        515                 520                 525
```

-continued

```
acc ccc ggc agc ggc ggc ccc ccc aga gag ggc ggg gcc cac atc acc    1632
Thr Pro Gly Ser Gly Gly Pro Pro Arg Glu Gly Gly Ala His Ile Thr
    530                 535                 540 cag ccc tgc ggc agt ggc ggc tcc gtc gac cct gag ctc ttc ctg ccc    1680
Gln Pro Cys Gly Ser Gly Gly Ser Val Asp Pro Glu Leu Phe Leu Pro
545                 550                 555                 560 agc aac acc ctg ccc acc tac gag cag ctg acc gtg ccc agg agg ggc    1728
Ser Asn Thr Leu Pro Thr Tyr Glu Gln Leu Thr Val Pro Arg Arg Gly
                565                 570                 575 ccc gat gag ggg tcc tgaggagggg atggggctgg gggatgggcc tgagtgagag    1783
Pro Asp Glu Gly Ser
                580 gggaggccaa gagtggcccc acctggccct ctctgaagga ggccacctcc taaaaggccc   1843 agagagaaga gccccactct cagaggcccc aatacccat ggaccatgct gtctggcaca   1903 gcctgcactt gggggctcag caaggccacc tcttcctggc cggtgtgggg gccccgtctc   1963 aggtctgagt tgttacccca agcgcctggg cccccacatg gtgatgttga catcactggc   2023 atggtggttg ggacccagtg gcagggcaca gggcctggcc catgtatggc caggaagtag   2083 cacaggctga gtgcaggccc accctgcttg gcccagggg cttcctgagg ggagacagag   2143 caaccctgg accccagcct caaatccagg accctgccag gcacaggcag ggcaggacca   2203 gcccacgctg actacagggc caccggcaat aaaagcccag gagcccattt ggagggcctg   2263 ggcctggctc cctcactctc aggaaatgct gacccatggg caggagactg tggagactgc   2323 tcctgagccc ccagcttcca gcaggaggga cagtctcacc atttccccag ggcacgtggt   2383 tgagtggggg gaacgcccac ttccctgggt tagactgcca gctcttccta gctggagagg   2443 agccctgcct ctccgcccct gagcccactg tgcgtggggc tcccgcctcc aaccctcgc    2503 ccagtcccag cagccagcca aacacacaga aggggactgc cacctcccct tgccagctgc   2563 tgagccgcag agaagtgacg gttcctacac aggacagggg ttccttctgg gcattacatc   2623 gcatagaaat caataatttg tggtgatttg gatctgtgtt ttaatgagtt tcacagtgtg   2683 attttgatta ttaattgtgc aagctttcc taataaacgt ggagaatcac a            2734
```

<210> SEQ ID NO 80
<211> LENGTH: 581
<212> TYPE: PRT
<213> ORGANISM: Homo sapiens

<400> SEQUENCE: 80

```
Met Glu Thr Arg Gly Ser Arg Leu Thr Gly Gly Gln Gly Arg Val Tyr
 1               5                  10                  15

Asn Phe Leu Glu Arg Pro Thr Gly Trp Lys Cys Phe Val Tyr His Phe
                20                  25                  30

Ala Val Phe Leu Ile Val Leu Val Cys Leu Ile Phe Ser Val Leu Ser
            35                  40                  45

Thr Ile Glu Gln Tyr Ala Ala Leu Ala Thr Gly Thr Leu Phe Trp Met
        50                  55                  60

Glu Ile Val Leu Val Val Phe Phe Gly Thr Glu Tyr Val Val Arg Leu
 65                  70                  75                  80

Trp Ser Ala Gly Cys Arg Ser Lys Tyr Val Gly Leu Trp Gly Arg Leu
                85                  90                  95

Arg Phe Ala Arg Lys Pro Ile Ser Ile Ile Asp Leu Ile Val Val Val
                100                 105                 110

Ala Ser Met Val Val Leu Cys Val Gly Ser Lys Gly Gln Val Phe Ala
            115                 120                 125
```

```
Thr Ser Ala Ile Arg Gly Ile Arg Phe Leu Gln Ile Leu Arg Met Leu
    130                 135                 140

His Val Asp Arg Gln Gly Gly Thr Trp Arg Leu Leu Gly Ser Val Val
145                 150                 155                 160

Phe Ile His Arg Gln Glu Leu Ile Thr Thr Leu Tyr Ile Gly Phe Leu
                165                 170                 175

Gly Leu Ile Phe Ser Ser Tyr Phe Val Tyr Leu Ala Glu Lys Asp Ala
                180                 185                 190

Val Asn Glu Ser Gly Arg Val Glu Phe Gly Ser Tyr Ala Asp Ala Leu
                195                 200                 205

Trp Trp Gly Val Val Thr Val Thr Thr Ile Gly Tyr Gly Asp Lys Val
    210                 215                 220

Pro Gln Thr Trp Val Gly Lys Thr Ile Ala Ser Cys Phe Ser Val Phe
225                 230                 235                 240

Ala Ile Ser Phe Phe Ala Leu Pro Ala Gly Ile Leu Gly Ser Gly Phe
                245                 250                 255

Ala Leu Lys Val Gln Gln Lys Gln Arg Gln Lys His Phe Asn Arg Gln
                260                 265                 270

Ile Pro Ala Ala Ala Ser Leu Ile Gln Thr Ala Trp Arg Cys Tyr Ala
                275                 280                 285

Ala Glu Asn Pro Asp Ser Ser Thr Trp Lys Ile Tyr Ile Arg Lys Ala
    290                 295                 300

Pro Arg Ser His Thr Leu Leu Ser Pro Ser Pro Lys Pro Lys Lys Ser
305                 310                 315                 320

Val Val Val Lys Lys Lys Lys Phe Lys Leu Asp Lys Asp Asn Gly Val
                325                 330                 335

Thr Pro Gly Glu Lys Met Leu Thr Val Pro His Ile Thr Cys Asp Pro
                340                 345                 350

Pro Glu Glu Arg Arg Leu Asp His Phe Ser Val Asp Gly Tyr Asp Ser
                355                 360                 365

Ser Val Arg Lys Ser Pro Thr Leu Leu Glu Val Ser Met Pro His Phe
    370                 375                 380

Met Arg Thr Asn Ser Phe Ala Glu Asp Leu Asp Leu Glu Gly Glu Thr
385                 390                 395                 400

Leu Leu Thr Pro Ile Thr His Ile Ser Gln Leu Arg Glu His His Arg
                405                 410                 415

Ala Thr Ile Lys Val Ile Arg Arg Met Gln Tyr Phe Val Ala Lys Lys
                420                 425                 430

Lys Phe Gln Gln Ala Arg Lys Pro Tyr Asp Val Arg Asp Val Ile Glu
                435                 440                 445

Gln Tyr Ser Gln Gly His Leu Asn Leu Met Val Arg Ile Lys Glu Leu
    450                 455                 460

Gln Arg Arg Leu Asp Gln Ser Ile Gly Lys Pro Ser Leu Phe Ile Ser
465                 470                 475                 480

Val Ser Glu Lys Ser Lys Asp Arg Gly Ser Asn Thr Ile Gly Ala Arg
                485                 490                 495

Leu Asn Arg Val Glu Asp Lys Val Thr Gln Leu Asp Gln Arg Leu Ala
                500                 505                 510

Leu Ile Thr Asp Met Leu His Gln Leu Leu Ser Leu His Gly Gly Ser
                515                 520                 525

Thr Pro Gly Ser Gly Gly Pro Pro Arg Glu Gly Gly Ala His Ile Thr
    530                 535                 540
```

```
                                  -continued

Gln Pro Cys Gly Ser Gly Gly Ser Val Asp Pro Glu Leu Phe Leu Pro
545                 550                 555                 560

Ser Asn Thr Leu Pro Thr Tyr Glu Gln Leu Thr Val Pro Arg Arg Gly
                565                 570                 575

Pro Asp Glu Gly Ser
                580
```